US010286532B2

(12) United States Patent
Garcia et al.

(10) Patent No.: US 10,286,532 B2
(45) Date of Patent: May 14, 2019

(54) FASTENER CARTRIDGE

(71) Applicant: Zimmer Biomet CMF and Thoracic, LLC, Jacksonville, FL (US)

(72) Inventors: Saddy Garcia, St. Augustine, FL (US); James Licht, Jacksonville, FL (US); Myles Tonkinson, Warsaw, IN (US); Kerwin Suarez, Jacksonville, FL (US); Lawrence Jene Chadwell, Yoder, IN (US); Ryan Luby, Ponte Vedra Beach, FL (US); Nicolai Ussin, Saint John's, FL (US); Rachel Hale, Jacksonville, FL (US); Brian Lamothe, Wallingford, CT (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 139 days.

(21) Appl. No.: 15/274,221

(22) Filed: Sep. 23, 2016

(65) Prior Publication Data

US 2017/0087697 A1 Mar. 30, 2017

Related U.S. Application Data

(60) Provisional application No. 62/233,193, filed on Sep. 25, 2015.

(51) Int. Cl.
*B23P 23/06* (2006.01)
*B25B 23/06* (2006.01)
(Continued)

(52) U.S. Cl.
CPC .......... *B25B 23/065* (2013.01); *A61B 17/068* (2013.01); *A61B 17/861* (2013.01);
(Continued)

(58) Field of Classification Search
CPC ............................. B60F 3/0007; B63H 11/12
See application file for complete search history.

(56) References Cited

U.S. PATENT DOCUMENTS 8,282,651 B2 10/2012 Ciccone et al.
8,377,074 B2 2/2013 Garcia et al.
(Continued)

FOREIGN PATENT DOCUMENTS

FR 881445 A 4/1943
WO WO-2007056399 A1 5/2007
WO WO-2017053723 A1 3/2017

OTHER PUBLICATIONS

"International Application Serial No. PCT/US2016/053336, International Search Report dated Feb. 1, 2017", 5 pgs.
(Continued)

*Primary Examiner* — John C Hong
(74) *Attorney, Agent, or Firm* — Schwegman Lundberg & Woessner, P.A.

(57) ABSTRACT

A fastener cartridge can be used with a shaft of a tool during an orthopedic procedure. The fastener cartridge can have a main housing that can be attached to fastener housing including a fastener chamber and a backstop component. The fastener chamber includes a plurality of non-flexible tabs and the backstop component includes a plurality of resiliently flexible tabs. The fastener housing is configured to include a plurality of fasteners that are arranged therein such that the longitudinal axes of the fastener chamber and the plurality of fasteners are collinear. The plurality non-flexible tabs prevent one of the fasteners from inadvertently passing entirely out of an outlet of the fastener chamber and the plurality of resiliently flexible tabs allow the fasteners to move axially in the first direction and restrict movement of the fasteners in a second direction opposite the first direction.

17 Claims, 35 Drawing Sheets

(51) Int. Cl.
  *B25B 15/02* (2006.01)
  *A61B 17/86* (2006.01)
  *A61B 17/068* (2006.01)
  *A61B 17/88* (2006.01)
  *A61B 17/064* (2006.01)

(52) U.S. Cl.
  CPC ........ *A61B 17/865* (2013.01); *A61B 17/8891* (2013.01); *B25B 15/02* (2013.01); *A61B 2017/0648* (2013.01)

(56) References Cited

U.S. PATENT DOCUMENTS

| | | |
|---|---|---|
| 8,534,164 B2 | 9/2013 | Watt |
| 2004/0243139 A1 | 12/2004 | Lewis et al. |
| 2007/0119871 A1* | 5/2007 | Garcia ................ A61B 17/865 |
| | | 222/325 |
| 2008/0016989 A1 | 1/2008 | Walker |

OTHER PUBLICATIONS

"International Application Serial No. PCT/US2016/053336, Written Opinion dated Feb. 1, 2017", 6 pgs.

\* cited by examiner

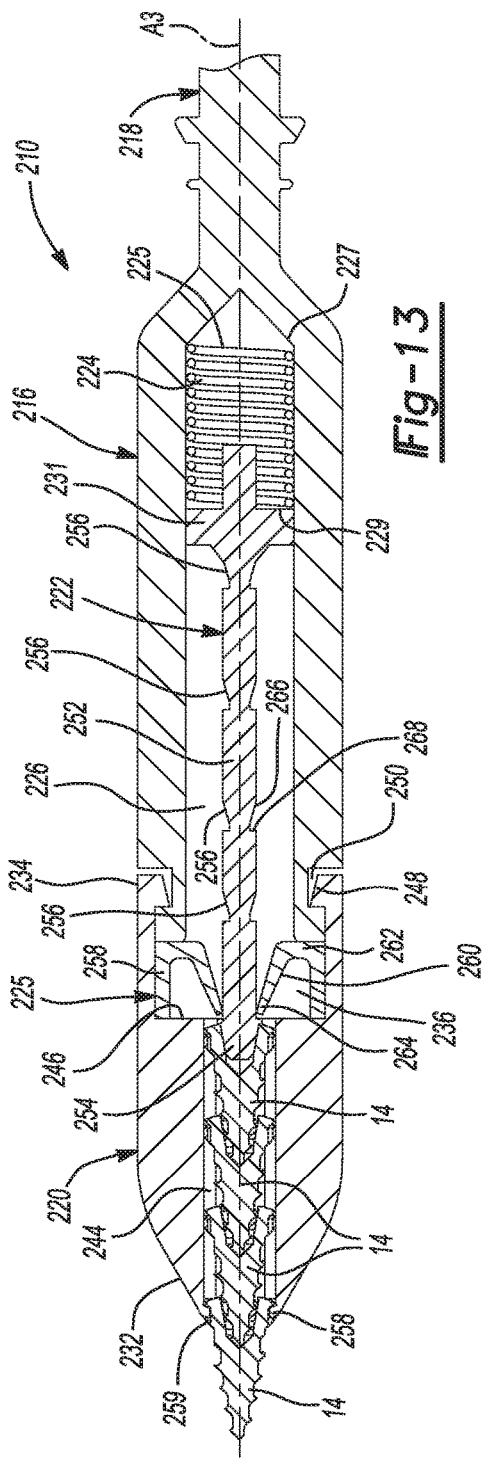
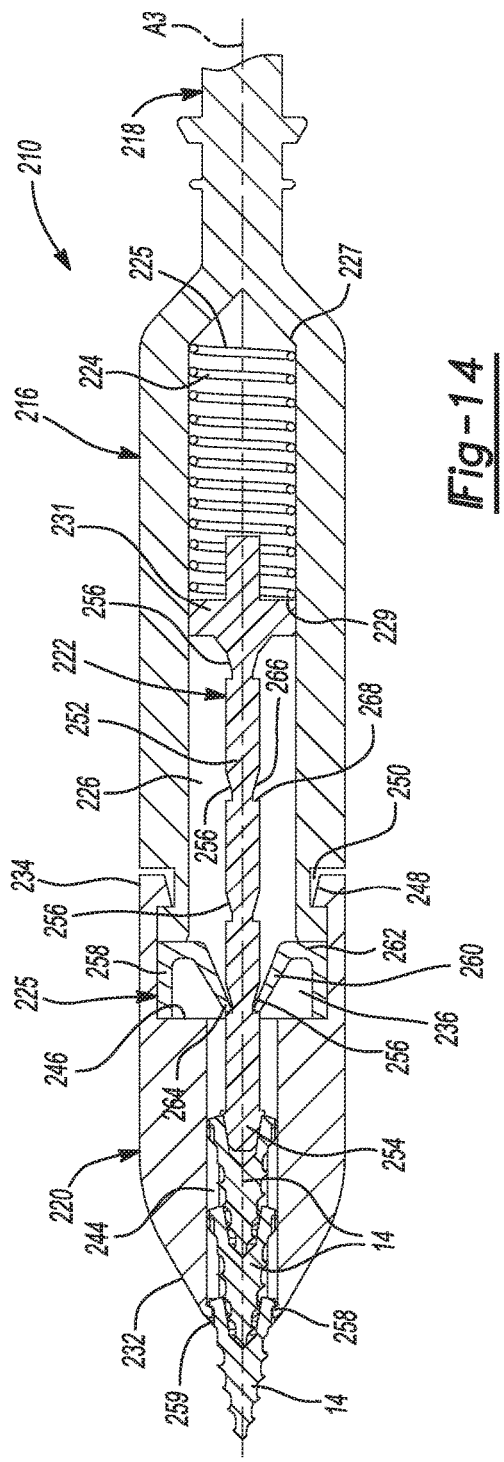

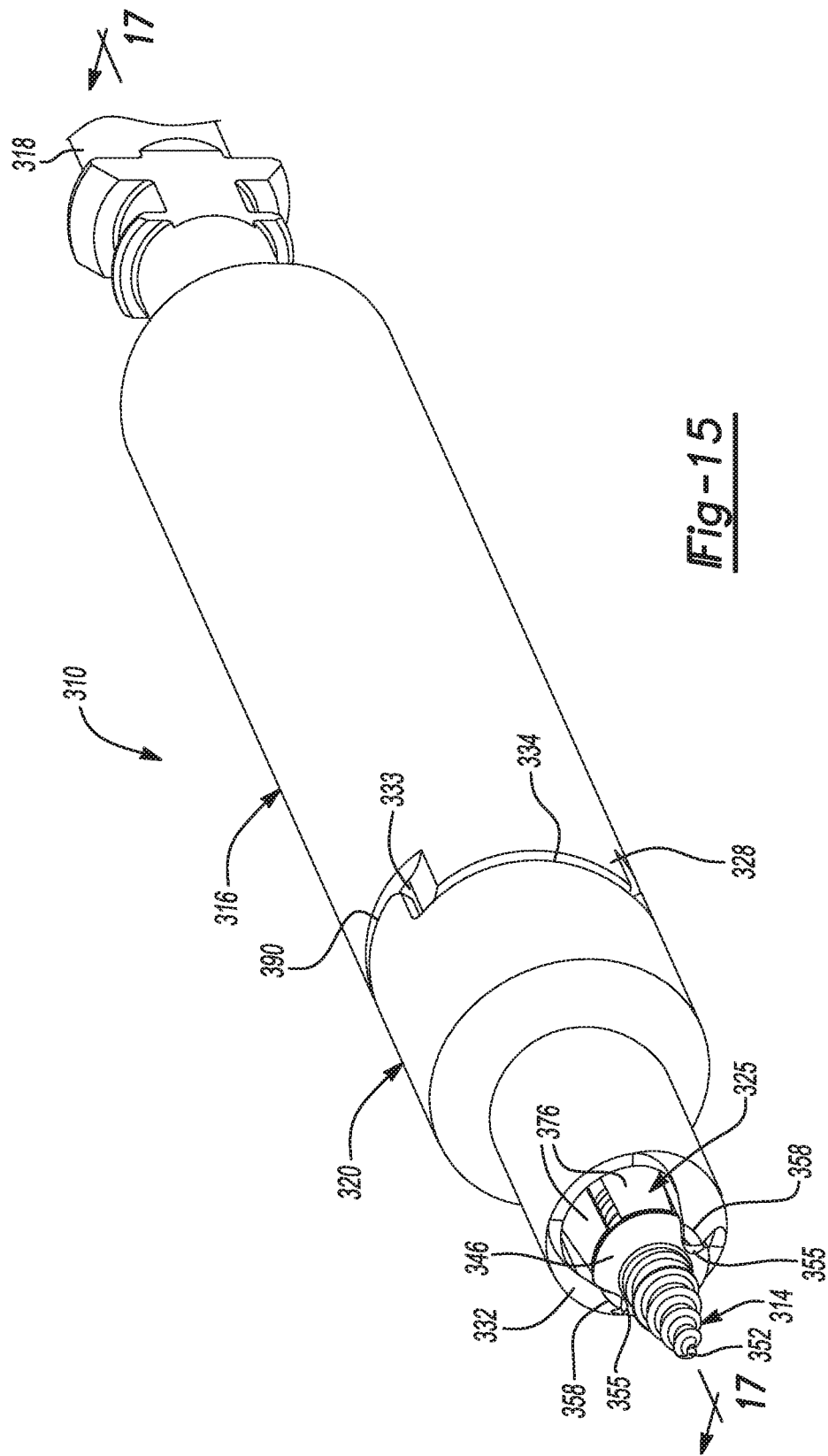

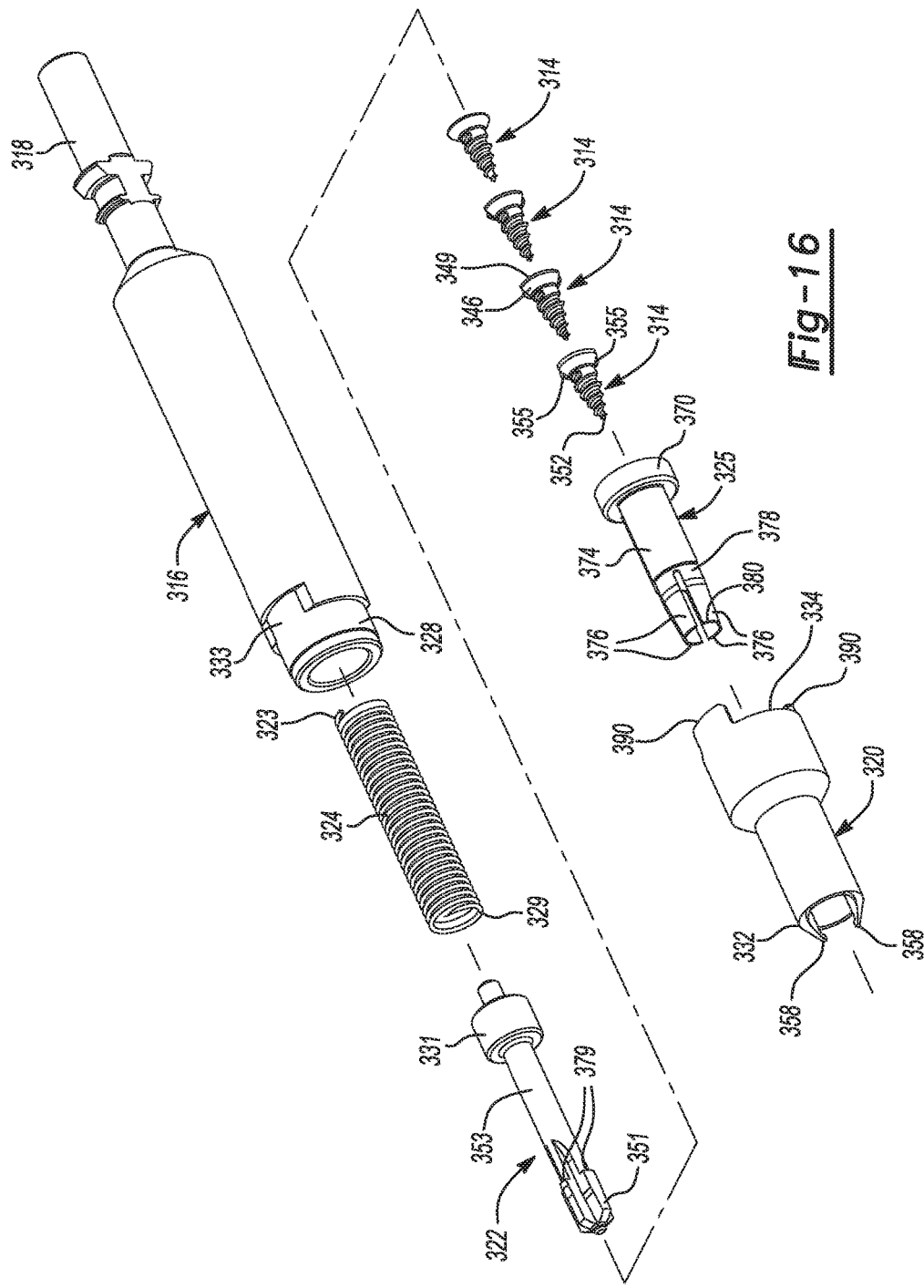

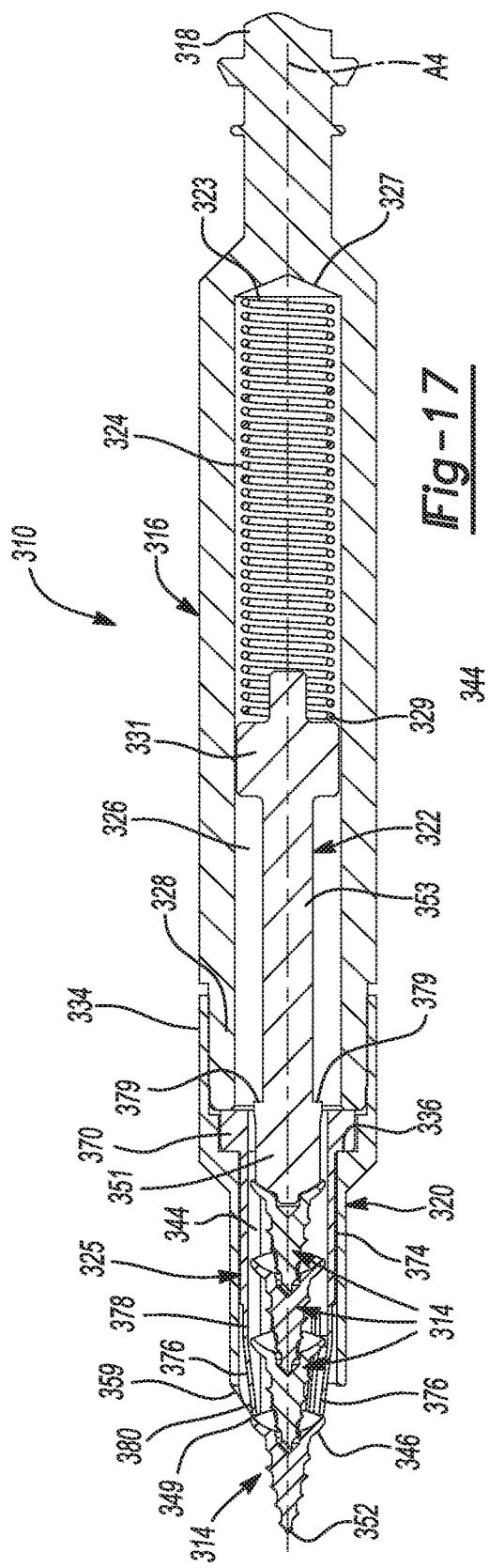
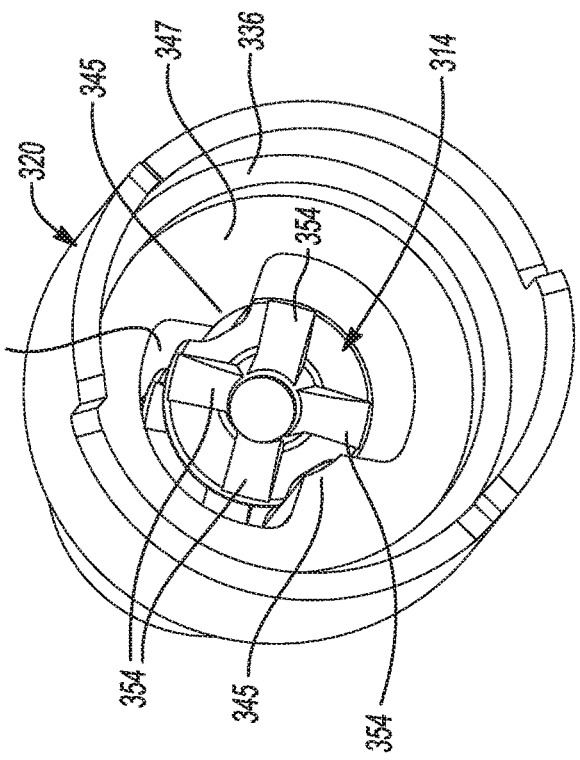
Fig-17
Fig-18

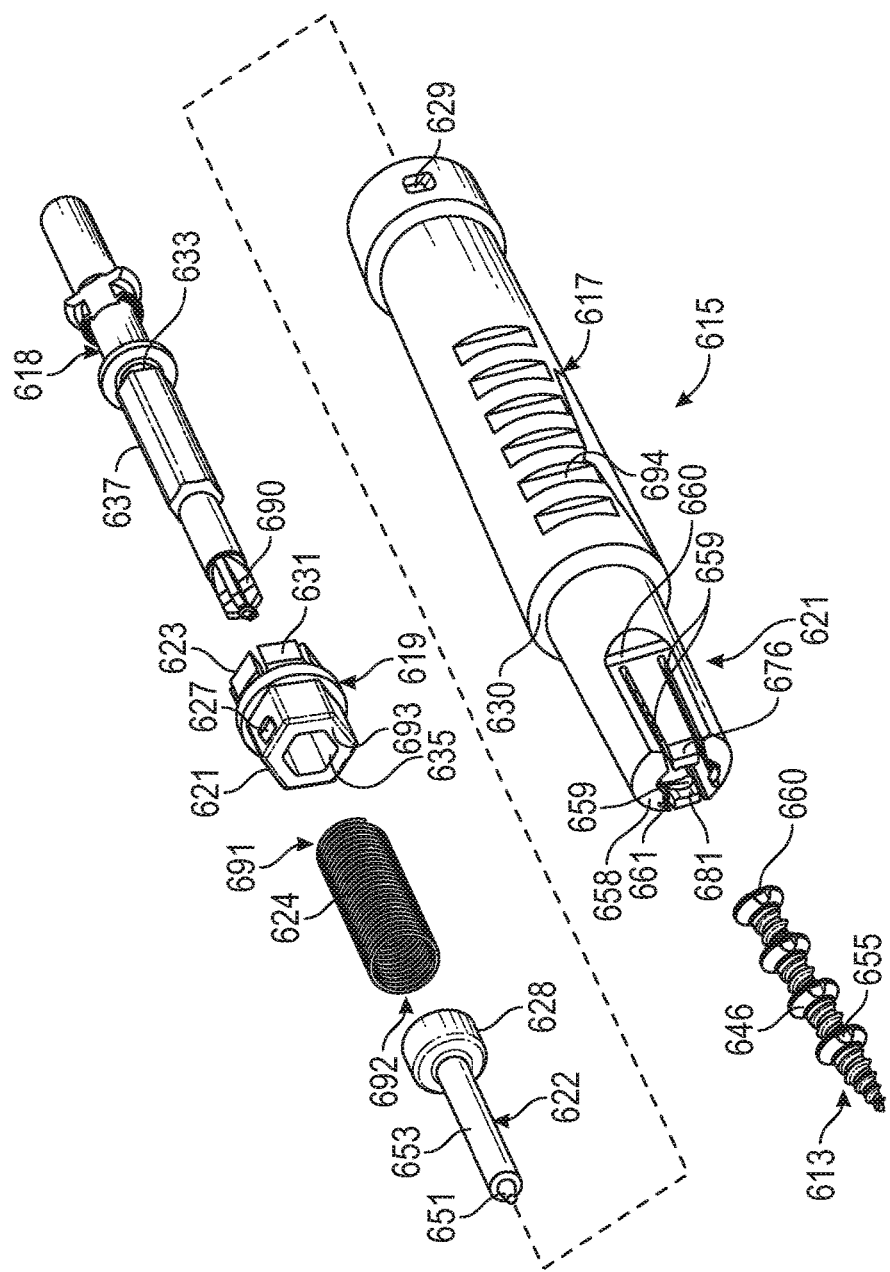

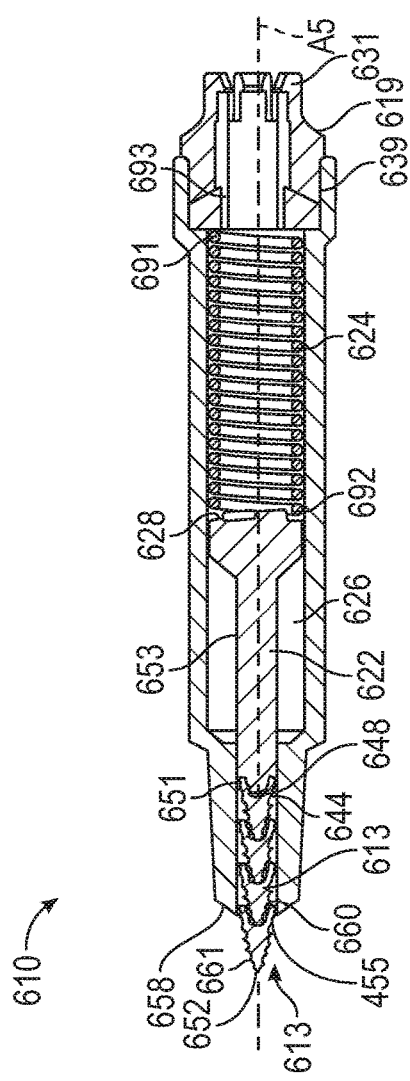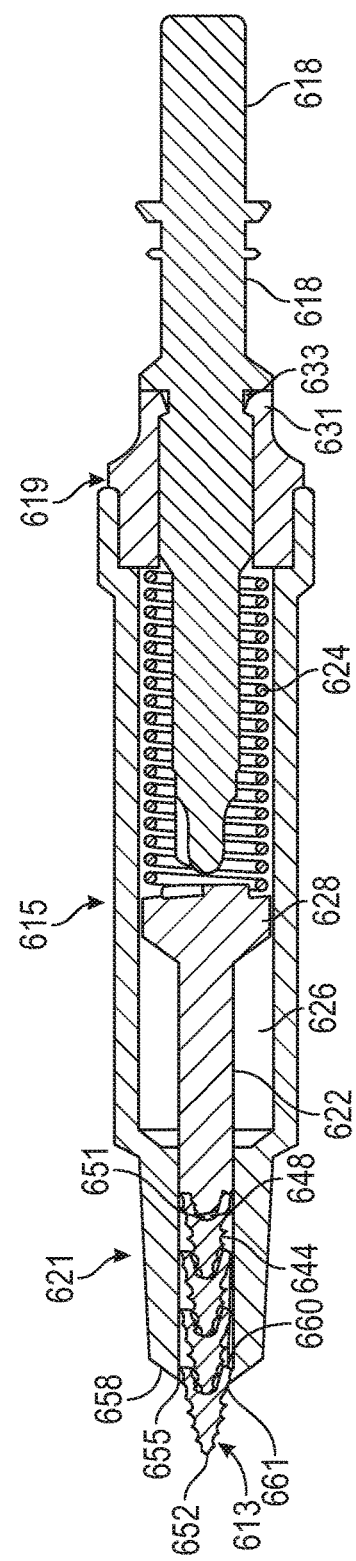

FASTENER CARTRIDGE

CLAIM OF PRIORITY

This application claims the benefit of U.S. Provisional Patent Application Ser. No. 62/233,193, filed on Sep. 25, 2015, the benefit of priority of which is claimed hereby, and which is incorporated by reference herein in its entirety.

FIELD

The present disclosure relates to a fastener cartridge for a fastener driver.

BACKGROUND

This section provides background information related to the present disclosure and is not necessarily prior art.

In order to drive multiple screws and other fasteners into an object, a single screw is typically loaded onto a screwdriver and driven into the object before a subsequent screw is loaded onto the screwdriver and driven into the object. This process can be time consuming and cumbersome and can lead to the operator dropping and/or misplacing one or more of the screws. Furthermore, preventing screws from inadvertently disengaging a typical screwdriver before the screw is driven into the object can be difficult, and often requires the operator to manually hold the screw on the tip of the screwdriver.

SUMMARY

This section provides a general summary of the disclosure, and is not a comprehensive disclosure of its full scope or all of its features.

In one form, the present disclosure provides a fastener cartridge that may include a body, a plunger, a fastener housing, a spring and a resiliently flexible tab. The body may define an inner cavity. The plunger may be disposed within the inner cavity and may be axially movable within the inner cavity. The fastener housing may extend from a first axial end of the body and may include a fastener chamber shaped to receive a plurality of fasteners arranged therein such that longitudinal axes of the fastener chamber and the fasteners are collinear. The fastener chamber may be shaped to prevent relative rotation between the fasteners and the fastener housing and to allow the fasteners to move therein along the longitudinal axes in response to axial movement of the plunger relative to the body. The spring may bias the plunger in a first direction into contact with one of the fasteners and may urge the plunger toward an outlet of the fastener chamber at a distal end of the fastener housing farthest from the spring. The resiliently flexible tab may allow the plunger and fasteners to move axially in the first direction and may restrict movement of the fasteners in a second direction opposite the first direction.

In some configurations, the resiliently flexible tab is attached to a backstop component.

In some configurations, the backstop component is disposed within the fastener housing.

In some configurations, the backstop component receives and extends circumferentially around at least a portion of the fastener housing.

In some configurations, the backstop component includes a plurality of resiliently flexible tabs that flex outward away from the longitudinal axes to allow the fasteners to move axially in the first direction. The resiliently flexible tabs interfere with a head of one of the fasteners to restrict movement of the fasteners in the second direction.

In some configurations, the resiliently flexible tab is attached to the plunger and is engageable with a plurality of detents in the body to restrict movement of the fasteners and the plunger in the second direction.

In some configurations, the resiliently flexible tab is attached to the fastener housing at the distal end of the fastener housing and is engageable with the fasteners to restrict movement of the fasteners in the second direction.

In some configurations, the resiliently flexible tab is disposed radially outward relative to the plunger and is engageable with a plurality of detents formed in the plunger to restrict movement of the plunger in the second direction.

In some configurations, the fastener cartridge includes a shaft extending from a second axial end of the body and configured to engage a driver.

In some configurations, each of the fasteners includes a head having a shape that matches the shape of the fastener chamber to prevent relative rotation between the fasteners and the fastener housing.

In some configurations, the plunger includes a tip having a shape that matches the shape of the fastener chamber to prevent relative rotation between the plunger and the fastener housing while the tip is at least partially received in the fastener chamber. The tip of the plunger can have a flat-head screwdriver configuration or a Phillips-head screwdriver configuration, for example.

In some configurations, the plunger is movable between a fastener-advancing position in which the tip and at least one of the fasteners are at least partially disposed within the fastener chamber and a driver position in which no fasteners are present in the fastener chamber and at least a portion of the tip is protruding out of the outlet of the fastener chamber.

In some configurations, a portion of the plunger is sized to prevent the entire plunger from passing through the fastener chamber.

In some configurations, the fastener housing includes a plurality of non-flexible tabs protruding radially inward into the fastener chamber at the outlet of the fastener chamber. The non-flexible tabs may engage a head of one of the fasteners to prevent the one of the fasteners from inadvertently passing entirely out of the outlet. The non-flexible tabs may deform the head of the one of the fasteners to release the one of the fasteners from the fastener chamber in response to an application of force by a user.

In some configurations, the plunger includes a cavity that receives a portion of the spring.

In some configurations, a tip of at least one of the fasteners is received in a recess in a head of an adjacent one of the fasteners.

In some configurations, the fastener cartridge includes an adaptor connecting the shaft to the body. The adaptor may removably engaging the shaft.

In some configurations, an end of the shaft is received within the inner cavity of the body and includes a tip shaped to engage one or more slots in a head of one of the fasteners. The plunger may be disposed between the end of the shaft and the fastener housing.

In some configurations, the adaptor includes a plurality of flexible tabs that snap into engagement with an annular recess in the shaft.

In another form, the present disclosure provides a tool that may include a shaft, a fastener housing, and a plunger. The shaft may be configured to engage a driver. The fastener housing may be rotationally fixed relative to the shaft and may include a fastener chamber shaped to receive a plurality of fasteners axially aligned therein and disposed along a longitudinal axis of the shaft. The fastener chamber may be shaped to prevent relative rotation between the fasteners and the fastener housing and to allow the fasteners to move therein along the longitudinal axis. The plunger may contact one of the fasteners and urge the one of the fasteners in a first direction along the longitudinal axis toward an outlet of the fastener chamber. The tool may also include means for allowing the plunger and fasteners to move axially in the first direction and restricting movement of the fasteners in a second direction opposite the first direction.

In some configurations, the plunger is movable between a fastener-advancing position in which a tip of the plunger and at least one of the fasteners are at least partially disposed within the fastener chamber and a driver position in which no fasteners are present in the fastener chamber and at least a portion of the tip is protruding out of the outlet of the fastener chamber.

In some configurations, the means includes a resiliently flexible tab attached to the plunger and engageable with a plurality of detents in a body housing the plunger to restrict movement of the fasteners and the plunger in the second direction.

In some configurations, the means includes a resiliently flexible tab attached to the fastener housing at the distal end of the fastener housing and engageable with the fasteners to restrict movement of the fasteners in the second direction.

In some configurations, the means includes a resiliently flexible tab disposed radially outward relative to the plunger and engageable with a plurality of detents formed in the plunger to restrict movement of the plunger in the second direction.

In some configurations, the means includes a resiliently flexible tab attached to a backstop component disposed within the fastener housing.

In some configurations, the backstop component includes a plurality of resiliently flexible tabs that flex outward away from the longitudinal axes to allow the fasteners to move axially in the first direction. The resiliently flexible tabs interfere with a head of one of the fasteners to restrict movement of the fasteners in the second direction.

In some configurations, the means includes a resiliently flexible tab attached to a backstop component that receives and extends circumferentially around at least a portion of the fastener housing.

In some configurations, the backstop component includes a plurality of resiliently flexible tabs that flex outward away from the longitudinal axes to allow the fasteners to move axially in the first direction. The resiliently flexible tabs interfere with a head of one of the fasteners to restrict movement of the fasteners in the second direction.

In some configurations, the tool includes a tubular body extending between the shaft and the fastener housing; and an adaptor connecting the shaft to the body, the adaptor removably engaging the shaft.

In some configurations, an end of the shaft is received within the inner cavity of the body and includes a tip shaped to engage one or more slots in a head of one of the fasteners. The plunger is disposed between the end of the shaft and the fastener housing.

In some configurations, the adaptor includes a plurality of flexible tabs that snap into engagement with an annular recess in the shaft.

In another form, the present disclosure provides a method that may include arranging a plurality of fasteners in a fastener cartridge such that longitudinal axes of the fasteners aligned with a longitudinal axis of the fastener cartridge, the fasteners being rotationally fixed relative to the fastener cartridge, a first one of the fasteners extending out of an outlet of the fastener cartridge; rotating the fastener cartridge about the longitudinal axis of the fastener cartridge to threadably drive the first one of the fasteners into an object; separating the first one of the fasteners from the fastener cartridge; and automatically advancing a second one of the fasteners out of the outlet of the fastener cartridge after the fastener cartridge is separated from the first one of the fasteners. The second one of the fasteners may be automatically advanced out of the outlet without any human interaction.

In some configurations, the method includes separating the second one of the fasteners from the fastener cartridge; and automatically advancing a third one of the fasteners out of the outlet of the fastener cartridge after the fastener cartridge is separated from the second one of the fasteners. The third one of the fasteners may be automatically advanced out of the outlet without any human interaction.

In some configurations, automatically advancing the second one of the fasteners out of the outlet includes pushing the second one of the fasteners out of the outlet with a plunger by moving the plunger in a first direction along the longitudinal axis of the fastener cartridge.

In some configurations, the method includes restricting movement of the plunger and the second one of the fasteners in a second direction opposite the first direction.

In some configurations, the method includes extending a tip of the plunger out of the outlet after all of the fasteners have been separated from the fastener cartridge; engaging another fastener with the tip of the plunger while the tip of the plunger is extending out of the outlet; and driving the other fastener using the tip of the plunger.

In some configurations, the method includes engaging a head of one of the fasteners with the fastener cartridge to prevent the one of the fasteners from inadvertently passing entirely out of the outlet.

In some configurations, the method includes deforming the head of the one of the fasteners to separate the one of the fasteners from the fastener cartridge in response to an application of force by a user.

In some configurations, the method includes separating a shaft of the fastener cartridge from a body of the fastener cartridge, the shaft including a tip shaped to engage one or more slots of another fastener; and driving the other fastener with the tip directly engaging the other fastener and with the shaft directly engaging a driver.

In some configurations, the tip of the shaft is received within a cavity of the body before the shaft is separated from the body.

In another form, the present disclosure provides a fastener that is configured to be used with the fastener cartridge described above. The fastener may include a threaded shaft and a head disposed at an end of the threaded shaft. The head may include a plurality of lobes. The head may also include an end face facing away from the threaded shaft and a tapered surface. The tapered surface extending axially between the end face and the threaded shaft. The end face including socket and a first slot formed therein. The first slot may intersect the socket such that the socket extends through a central portion of the first slot. The first slot may extend radially outward from the socket in two opposite directions. The tapered surface of the head may include a plurality of recesses each disposed between adjacent lobes and each partially defined by a lip extending radially outward.

In some configurations, the lobes may define a generally cross-shaped periphery of the head.

In some configurations, the threaded shaft is tapered so that a tip of the threaded shaft can be received in the socket of another identical fastener.

In some configurations, the head includes a second slot formed in the end face. The second slot may extend perpendicularly to the first slot and may intersect the socket.

In another form, the present disclosure provides a fastener cartridge configured to be coupled to a shaft. The fastener cartridge a main housing defining extending from a first end to a second end, the main housing defining an opening extending from the first end to the second end and a locking aperture extending from an external surface to the opening; a drive clip positioned around the main housing, the drive clip including a base, an elongated leg extending from the base, and a projection extending from the elongated leg; a fastener housing including a fastener chamber including a plurality of non-flexible tabs and a backstop component including a plurality of resiliently flexible tabs, wherein the fastener housing is configured to include a plurality of fasteners that are arranged therein such that the longitudinal axes of the fastener chamber and the plurality of fasteners are collinear; and a locking sleeve configured move along the main housing and couple the fastener cartridge to a shaft of a tool.

In some configurations, the locking sleeve is configured to move between a first position, corresponding to an unlocked position, and a second position, corresponding to a locked position.

In some configurations, in the first position, the locking sleeve is engaged with the fastener chamber at a first location along the fastener chamber and the projection of the drive clip is positioned within the locking aperture but not within the opening defined by the main housing.

In some configurations, transitioning from the first position to the second position, the locking sleeve is disengaged from the fastener chamber and moved along the main housing toward the first end of the main housing until the locking sleeve is engaged with the fastener chamber at a second location along the fastener chamber, the second location closer to the first end of the main housing as compared to the first location.

In some configurations, at the second position, the elongated leg collapses against the main body forcing the projection of the drive clip to extend through the locking aperture and into the opening defined by the main housing.

In some configurations, the fastener cartridge includes a plunger disposed within and axially movable within the main housing and the fastener housing and a spring biasing the plunger in a first direction into contact with one of the fasteners and urging the plunger toward an outlet of the fastener chamber at a distal end of the fastener chamber farthest from the spring.

In some configurations, the plurality of resiliently flexible tabs allow the plunger and fasteners to move axially in the first direction and restrict movement of the fasteners in a second direction opposite the first direction.

In some configurations, a portion of the fastener chamber is shaped to prevent relative rotation between the fasteners and the fastener chamber and to allow the fasteners to move therein along the longitudinal axes in response to axial movement of the plunger relative to the body.

In some configurations, the plurality of resiliently flexible tabs are configured to transition from a first at-rest position to a second flexed position by flexing outward away from the longitudinal axes to allow the fasteners to move axially in the first direction.

In some configurations, at the first at-rest position, the resiliently flexible tabs are configured to interfere with a head of one of the fasteners to restrict movement of the fasteners in the second direction.

In another form, the present disclosure provides a system configured to be coupled to tool. The system includes a fastener cartridge, including: a main housing defining an opening that extends from a first end of the main body to a second end of the main housing; a drive clip positioned around the main housing, the drive clip including a projection configured to engage with a shaft of a tool; a fastener housing, including: a fastener chamber including a plurality of non-flexible tabs; and a backstop component including a plurality of resiliently flexible tabs, wherein the fastener housing is configured to include a plurality of fasteners that are arranged therein such that the longitudinal axes of the fastener chamber and the plurality of fasteners are collinear; and a locking sleeve configured move along the main housing between a first position, corresponding to an unlocked position, and a second position, corresponding to a locked position, wherein, at the locked position, the projection engages with the shaft to couple the fastener cartridge to the tool.

In some configurations, the fastener cartridge wherein the fastener cartridge further includes: a plunger disposed within axially movably within the main housing and the fastener housing; a spring biasing the plunger in a first direction into contact with one of the fasteners and urging the plunger toward an outlet of the fastener chamber at a distal end of the fastener chamber farthest from the spring.

In some configurations, each of the plurality of fasteners includes a threaded shaft; and a head disposed at an end of the threaded shaft and including a plurality of lobes and a plurality of recesses each disposed between adjacent lobes and each partially defined by one of a deformable lip extending radially outward and a ramped surface.

In some configurations, the plurality of non-flexible tabs are each configured to engage one of the deformable lip and ramped surface of one of the fasteners to prevent the one of the fasteners from inadvertently passing entirely out of the outlet, the non-flexible tabs configured to deform one of the deformable lip and the ramped surface of the one of the fasteners to release the one of the fasteners from the fastener chamber in response to an applied force by a user.

In some configurations, the plurality of resiliently flexible tabs are configured to transition from a first at-rest position to a second flexed position by flexing outward away from the longitudinal axes to allow the fasteners to move axially in the first direction, and wherein, at the first at-rest position, the resiliently flexible tabs are configured to interfere with a head of one of the fasteners to restrict movement of the fasteners in the second direction.

In some configurations, the shaft of the tool includes a groove, and wherein, at the locked position, the projection of the drive clip extends into the groove of the shaft.

In some configurations, when the fastener cartridge is coupled to the shaft, the shaft is axially and rotationally fixed with respect to the fastener cartridge.

In another form, the present disclosure provides a method including coupling a fastener cartridge including a plurality of fasteners to a shaft of a tool, wherein longitudinal axes of the plurality of fasteners are aligned with a longitudinal axis of a fastener cartridge, a first one of the fasteners extending out of an outlet of the fastener cartridge, and the fastener cartridge including a plurality of non-flexible tabs that extend radially into the outlet and a plurality of flexible tabs; rotating, via the tool, the fastener cartridge about the longitudinal axis of the fastener cartridge to threadably drive the first one of the plurality of fasteners into an object; separating the first one of the plurality of fasteners from the fastener cartridge; and automatically advancing a second one of the plurality of fasteners out of the outlet of the fastener cartridge after the fastener cartridge is separated from the first one of the plurality of fasteners, wherein the second one of the plurality of fasteners is automatically advanced out of the outlet without any human interaction.

In some configurations, each of the plurality of fasteners includes a threaded shaft; and a head disposed at an end of the threaded shaft and including a plurality of lobes and a plurality of recesses each disposed between adjacent lobes and each partially defined by one of a deformable lip extending radially outward and a ramped surface.

In some configurations, separating the first one of the plurality of fasteners from the fastener cartridge includes retracting the fastener cartridge such that the non-flexible tab at least partially deforms one of the deformable lip and the ramped surface of the first one of the plurality of fasteners such that the first one of the plurality of fasteners is separated from the fastener cartridge.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 13 is a cross-sectional view of another fastener cartridge with a plurality of fasteners according to the principles of the present disclosure;

FIG. 14 is a cross-sectional view of the fastener cartridge of FIG. 13 after one of the fasteners of FIG. 13 has been separated from the fastener cartridge;

FIG. 15 is a perspective view of another fastener cartridge according to the principles of the present disclosure;

FIG. 16 is an exploded perspective view of the fastener cartridge of FIG. 15;

FIG. 17 is a cross-sectional view of the fastener cartridge of FIG. 15;

FIG. 18 is a perspective view of a fastener housing of the fastener cartridge of FIG. 15 with a plurality of fasteners disposed therein;

FIG. 26 is an exploded perspective view of the fastener cartridge of FIG. 25;

FIG. 27 is a cross-sectional view of the fastener cartridge of FIG. 25;

FIG. 28 is a cross-sectional view of the fastener cartridge of FIG. 25;

Corresponding reference numerals indicate corresponding parts throughout the several views of the drawings.

DETAILED DESCRIPTION

Figure 1:
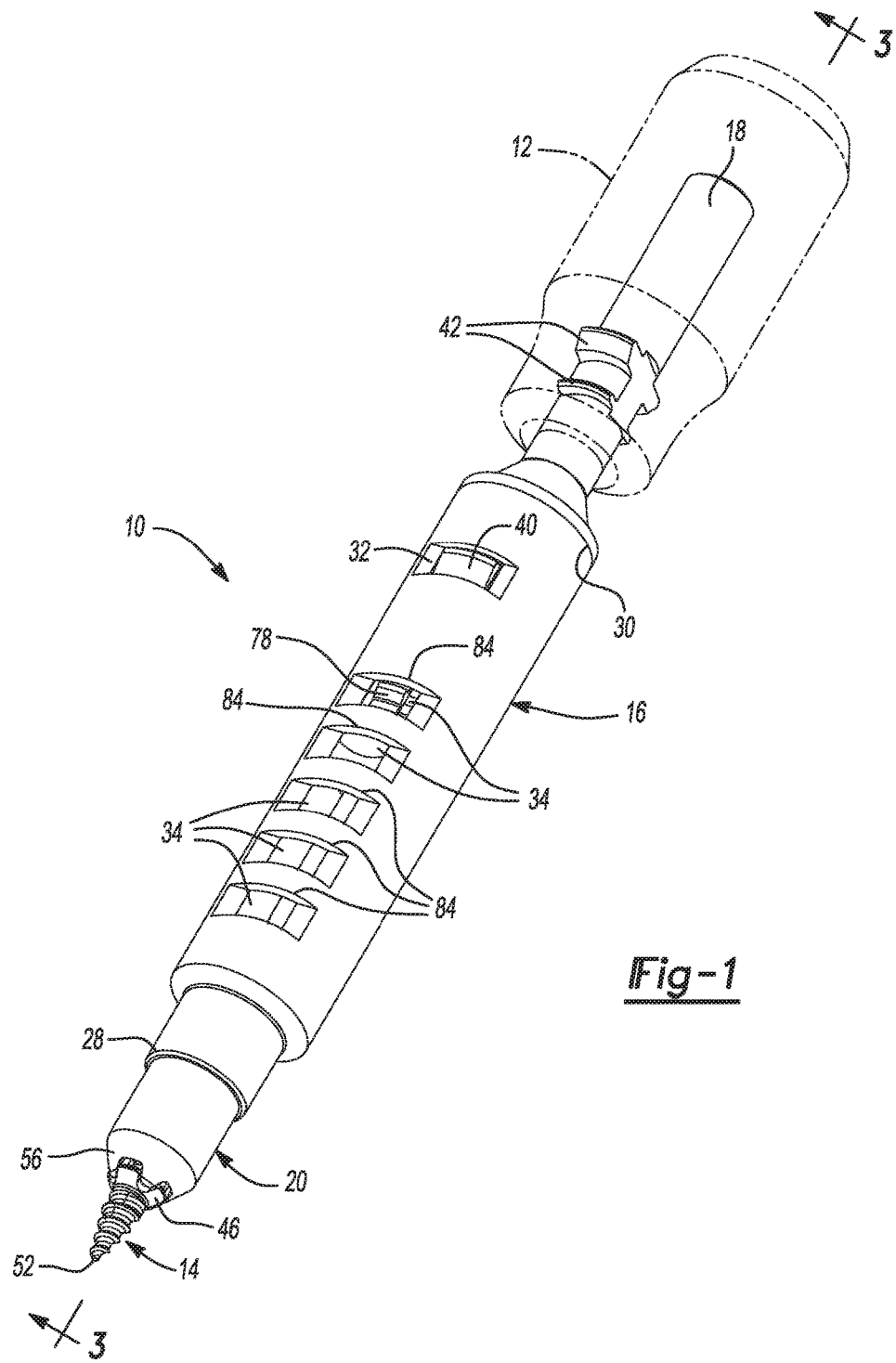
FIG. 1 is a perspective view of a fastener cartridge according to the principles of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference to FIGS. 1-10, a fastener cartridge 10 is provided that can be removably attached to a driver 12 (FIG. 1) for driving a plurality of fasteners 14 into an object (not shown). The object could be a component of a machine or apparatus or a bone or other tissue of a human or animal body, for example. While the driver 12 is shown in FIG. 1 as being a handle of a manual driver, it will be appreciated that the fastener cartridge 10 can be attached to and driven by an electric or pneumatic power driver, such as the iQ™ Intelligent Driver manufactured by Biomet Microfixation, for example. As will be described in more detail below, the fastener cartridge 10 can (1) simultaneously hold one of the plurality of fasteners 14 in a ready-to-be-driven position and one or more fasteners 14 in standby positions, (2) transmit torque from the driver 12 to the fasteners 14 to drive the fastener 14 in the ready-to-be-driven position into the object, and then (3) automatically advance a subsequent one of fasteners 14 to the ready-to-be-driven position.

Figure 2:
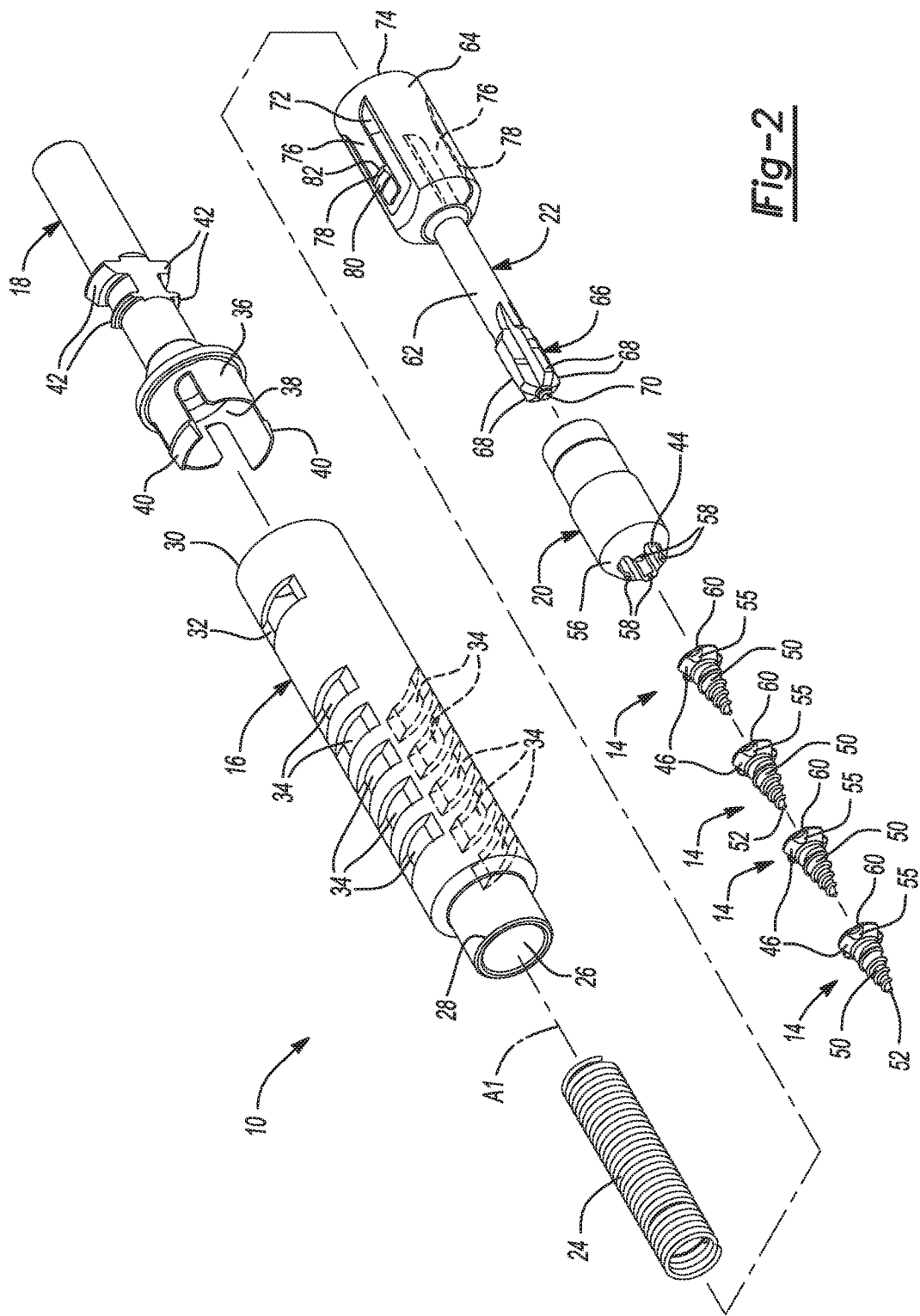
FIG. 2 is an exploded perspective view of the fastener cartridge.
Figure 3:
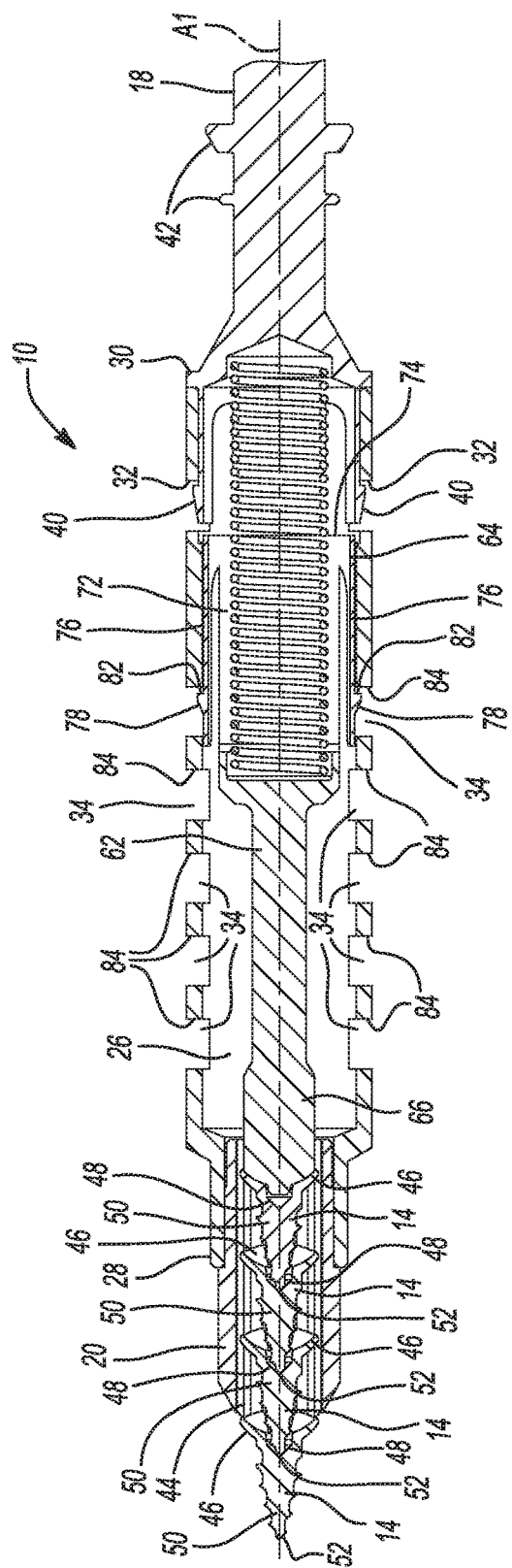
FIG. 3 is a cross-sectional view of the fastener cartridge with a plunger of the fastener cartridge in a first position.

As shown in FIGS. 1-3, the fastener cartridge 10 may include an outer housing or body 16, a shaft 18, a fastener housing 20, a plunger 22 and a spring 24. The housing 16 may be a generally tubular body defining an interior cavity 26. The cavity 26 may extend through first and second axial ends 28, 30 of the housing 16. The housing 16 may include a pair of first slots or detents 32 and a plurality of second slots or detents 34. The first detents 32 may be equidistant from the second axial end 30 and disposed one-hundred-eighty degrees apart from each other. The second detents 34 may be arranged in a pair of linear patterns disposed one-hundred-eighty degrees apart from each other.

The shaft 18 may include a collar 36 disposed at one end thereof. The collar 36 may be received in the cavity 26 at the second end 30 of the housing 16 such that the shaft 18 extends axially from the second end 30. The collar 36 may define a recess 38 in communication with the cavity 26 of the housing 16. The collar 36 may include a pair of barbed tabs 40 that snap into engagement with the first detents 32 to fix the shaft 18 relative to the housing 16. It will be appreciated that other methods of fixing the shaft 18 to the housing 16 may be employed (e.g., press fit and/or welding). In some configurations, the shaft 18 could be integrally formed with the housing 16. In the configuration shown in the figures, the shaft 18 includes protrusions 42 that can be received in the driver 12 to rotationally fix the shaft 18 relative to the driver 12 (thereby rotationally fixing the entire fastener cartridge 10 relative to the driver 12). It will be appreciated that the shaft 18 could include other features in addition to or instead of the protrusions 42 to engage the driver 12.

The fastener housing 20 may be attached to and extend from the first axial end 28 of the housing 16. For example, as shown in FIG. 3, a portion of the fastener housing 20 may be pressed into the cavity 26 at the first axial end 28 to fix the fastener housing 20 to the housing 16. One or more welds may be applied to permanently fix the fastener housing 20 to the housing 16. It will be appreciated that other methods of fixing the fastener housing 20 to the housing 16 may be employed (e.g., snap fit, etc.).

Figure 4:
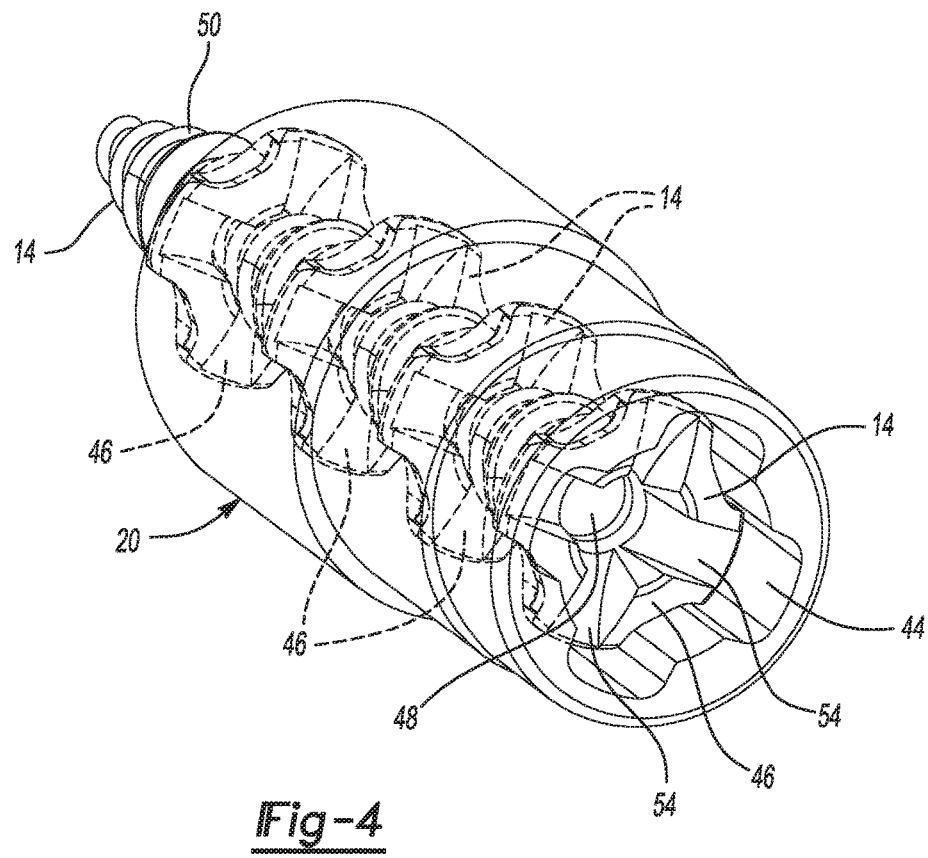
FIG. 4 is a perspective view of a fastener housing of the fastener cartridge with a plurality of fasteners disposed therein.

The fastener housing 20 may be a generally cylindrical body including a fastener chamber 44 that extends therethrough along a longitudinal axis A1 of the fastener housing 20 and housing 16. As shown in FIGS. 3 and 4, the fastener chamber 44 can receive at least a portion of a predetermined number of fasteners 14. The predetermined number of fasteners 14 may be equal to one less than the number of pairs of second detents 34 in the housing 16. In the configurations shown in figures, the predetermined number of fasteners 14 is four.

As shown in FIGS. 2-4, the fastener chamber 44 is shaped to correspond to a shape of heads 46 of the fasteners 14 (i.e., the fastener chamber 44 is shaped to be keyed to the shape of the heads 46), thereby allowing the fasteners 14 to move through the fasteners chamber 44 along the longitudinal axis A1 while preventing relative rotation between the fastener housing 20 and the fasteners 14. In the configuration shown in the figures, the fastener chamber 44 is generally shaped like a cross or a plus sign (+) and slidably receives correspondingly shaped heads 46 of the fasteners 14. That is, each head 46 may include lobes 47 that form a generally cross-shaped periphery of the head 46 (as shown in FIG. 4) It will be appreciated that the fastener chamber 44 and heads 46 could be alternatively shaped to rotationally key the heads 46 of the fasteners 14 to the fastener housing 20.

As shown in FIGS. 3 and 4, the fasteners 14 are arranged in an inline configuration within the fastener chamber 44. That is, longitudinal axes of the fasteners 14 are collinear with the longitudinal axis A1 when the fasteners 14 are disposed within the fastener housing 20. The fastener housing 20 can be assembled onto the housing 16 with the fasteners 14 already disposed within the fastener chamber 44. Therefore, in configurations where the fastener housing 20 is permanently attached to the housing 16 (e.g., via welding), the fastener chamber 44 may not be able to be reloaded with fasteners 14 after all of the fasteners 14 are driven into the object. In configurations where the fastener housing 20 is removably attached to the housing 16 (e.g., via snap fit), the fastener chamber 44 may be reloaded with fasteners 14.

Figure 5:
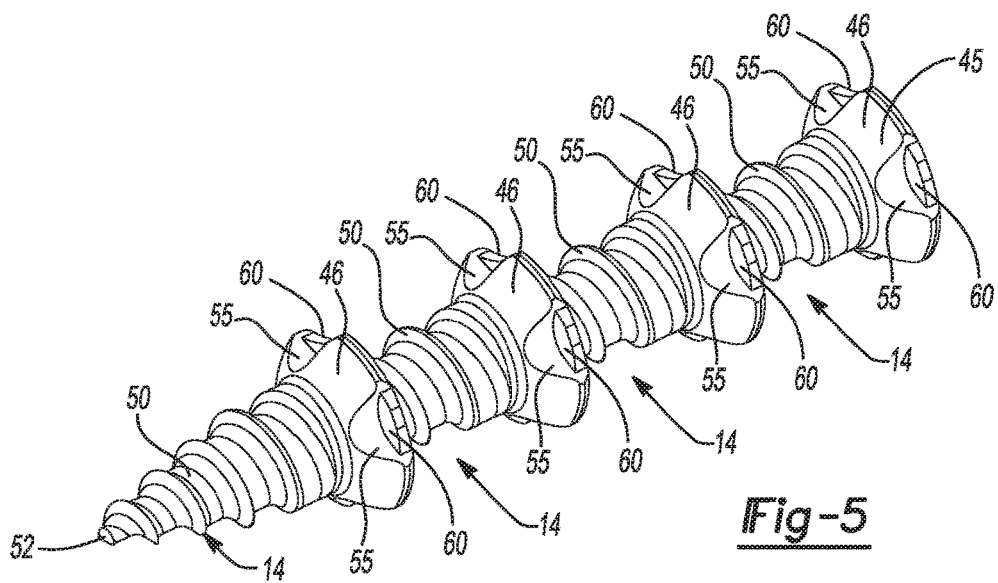
FIG. 5 is a perspective view of the plurality of fasteners.
Figure 8:
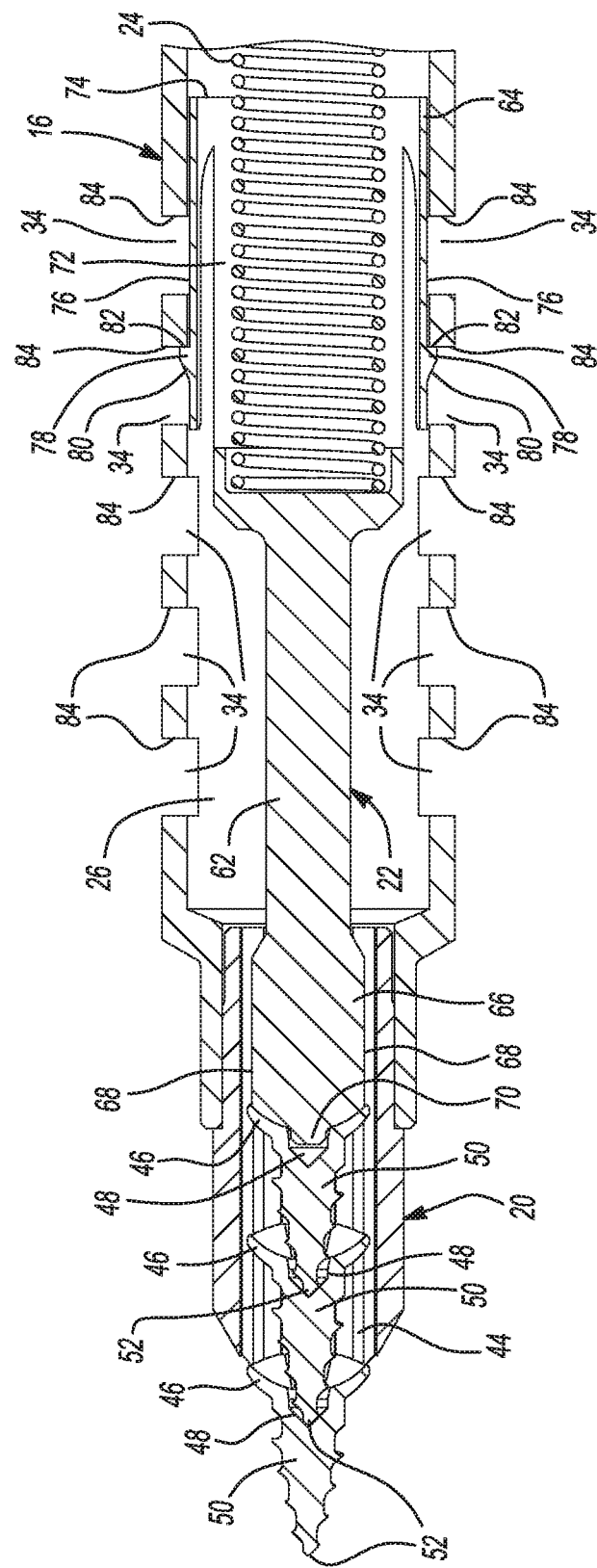
FIG. 8 is a partial cross-sectional view of the fastener cartridge after one of the fasteners of FIG. 3 has been separated from the fastener cartridge.

As shown in FIGS. 3 and 8, each fastener 14 includes a socket or recess 48 that extends along the longitudinal axis of the fastener 14 into the head 46. A threaded shaft 50 of each fastener 14 may have a tapered tip 52 that can be received in the recess 48 of an adjacent fastener 14 so that the fasteners 14 can be nested within each other. As shown in FIG. 4, the heads 46 of the fasteners 14 may also include one or more slots 54 that can be configured to receive a Phillips-head (cross-shaped) or flat-head driver tip, for example. A tapered outer peripheral surface 45 of the heads 46 may include depressions or recesses 55 (FIG. 5).

Figure 6:
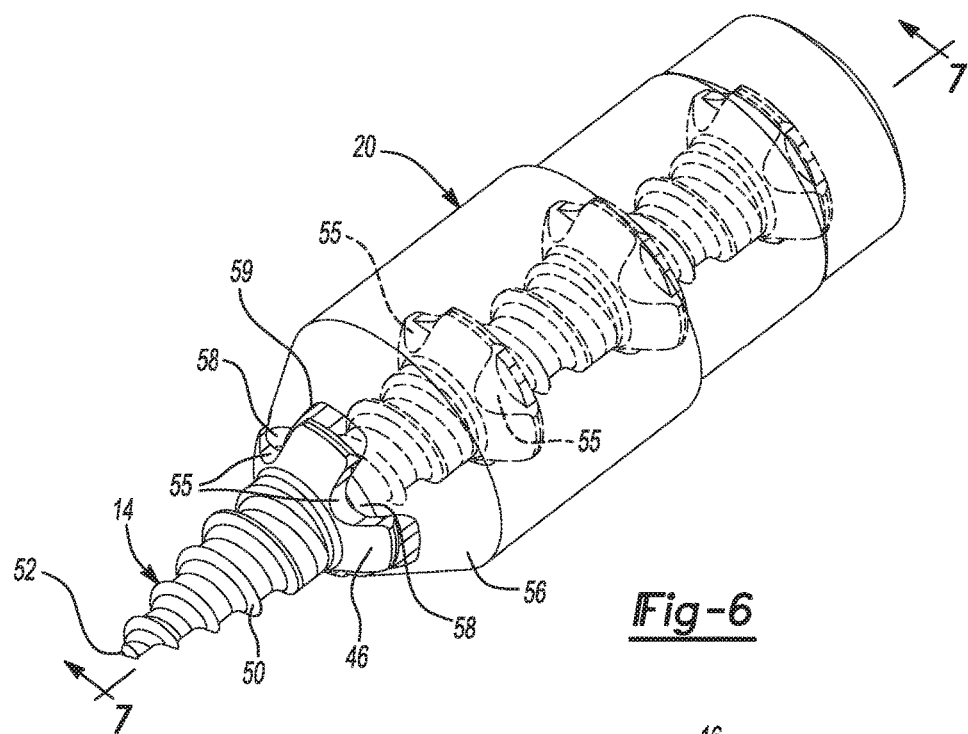
FIG. 6 is another perspective view of the fastener housing with the plurality of fasteners disposed therein.
Figure 7:
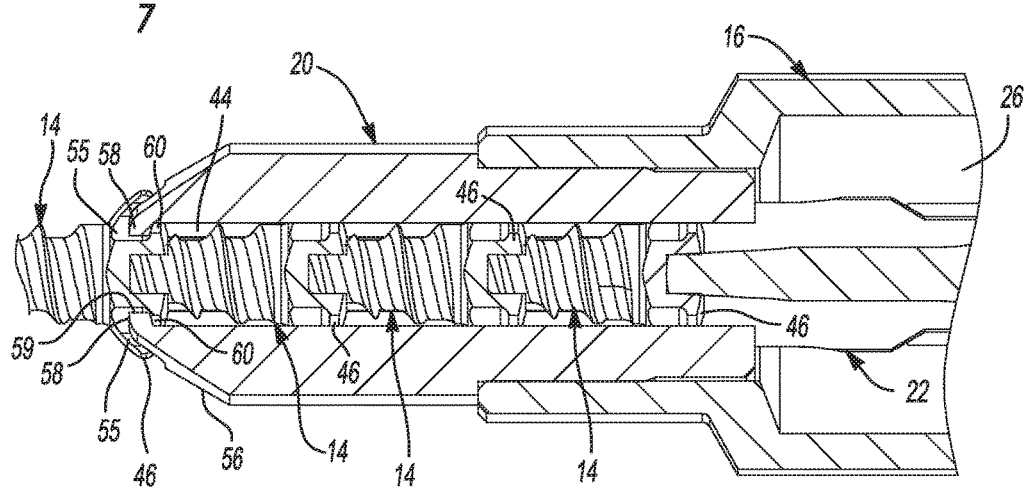
FIG. 7 is a partial cross-sectional view of the fastener cartridge showing tabs of the fastener housing engaging a head of one of the fasteners.

As shown in FIGS. 6 and 7, a distal end 56 of the fastener housing 20 may include a plurality of non-flexible tabs 58 that extend radially into the fastener chamber 44 at an outlet 59 of the fastener chamber 44. Each of the non-flexible tabs 58 may be received in a corresponding one of the recesses 55 in the fastener 14 that is in the ready-to-be-driven position (i.e., the fastener 14 that is extending out of the fastener chamber 44 and whose tip 52 is pointed away from the fastener cartridge 10). Interference between the non-flexible tabs 58 and lips 60 (i.e., lips 60 that partially define the recesses 55) of the ready-to-be-driven fastener 14 prevents inadvertent disengagement between the fastener cartridge 10 and the ready-to-be-driven fastener 14 (see FIG. 7). The non-flexible tabs 58 are rigid and are not resiliently flexible. As will be described in more detail below, the lips 60 can be deformed by the non-flexible tabs 58 in response to an application of force by a user of the fastener cartridge 10 to disengage the fastener 14 after the fastener 14 has been threadably driven into an object. In some configurations, the fasteners 14 may be made from a softer material than the fastener housing 20 to further facilitate deformation of the lips 60.

Figure 9:
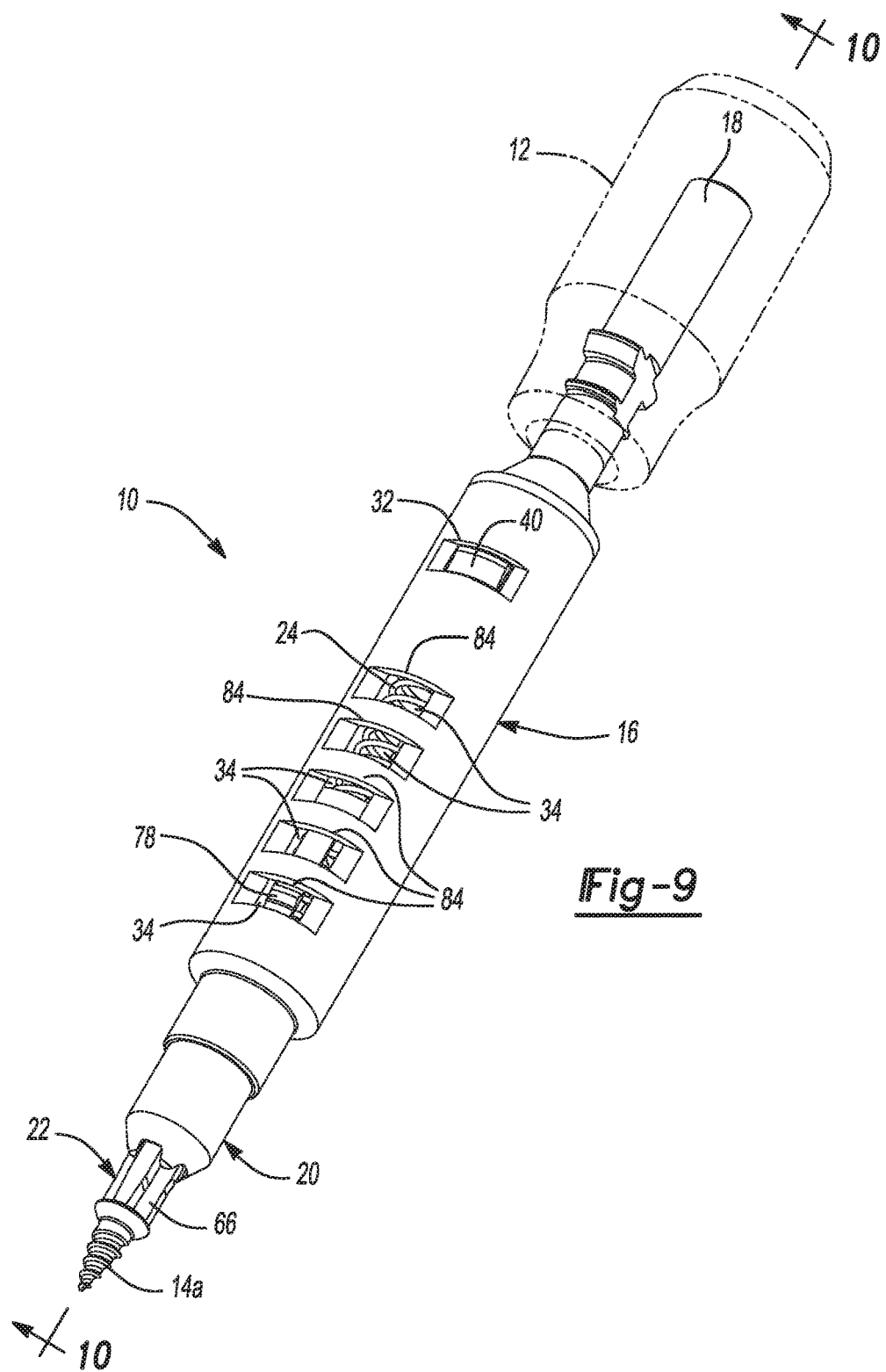
FIG. 9 is a perspective view of the fastener cartridge in a driver position after all of the fasteners have been separated from the fastener housing.
Figure 10:
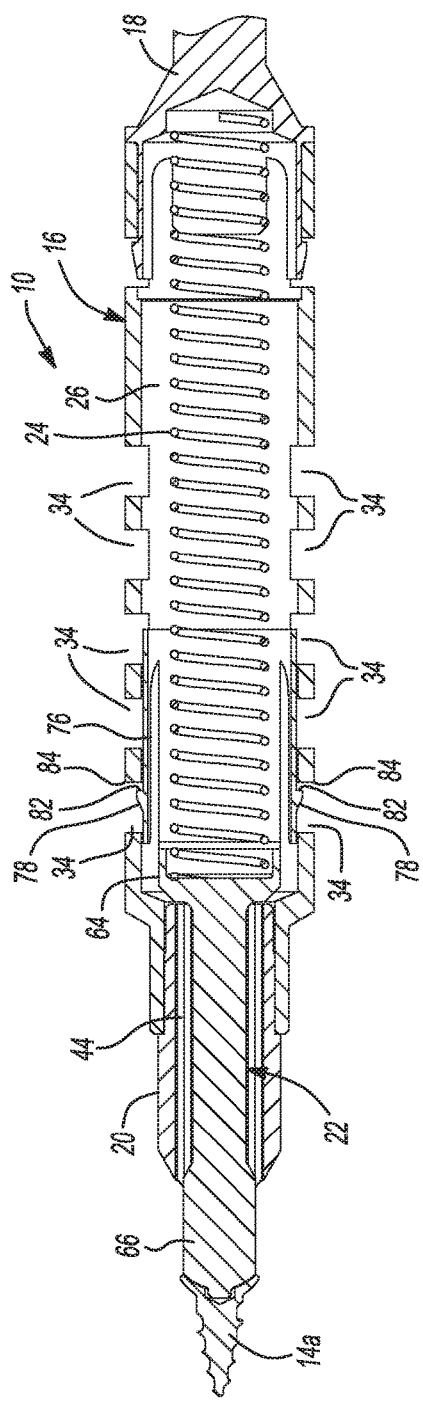
FIG. 10 is a cross-sectional view of the fastener cartridge in the driver position of FIG. 9.

As shown in FIGS. 2 and 3, the plunger 22 may include a shaft 62 extending from a body 64. The plunger 22 may be movable with the cavity 26 of the housing 16 among fastener-advancing positions (FIGS. 1, 3 and 8) and a driver position (FIGS. 9 and 10). The shaft 62 and body 64 may extend axially along the longitudinal axis A1 and may be centered on the longitudinal axis A1. The shaft 62 may include a tip 66 having a plurality of blades 68 that are shaped, sized and arranged to correspond to the shape of the fastener chamber 44 so that the tip 66 can slide through the fastener chamber 44 along the longitudinal axis A1 while rotationally fixing the plunger 22 relative to the fastener housing 20 while the tip 66 is received in the fastener chamber 44. The blades 68 are also shaped, sized and arranged to fit within the slots 54 of the fasteners 14. A distal end of the tip 66 may include a protrusion 70 that can be received in the recess 48 of one of the fasteners 14 (as shown in FIG. 8). While the tip 66 is shown in FIG. 2 as having four blades 68 configured in the shape of a Phillips-head screwdriver, it will be appreciated that the tip 66 could include only two blades 68 configured in the shape of a flat-head screwdriver.

The body 64 of the plunger 22 is disposed at the opposite axial end of the shaft 62 as the tip 66. The body 64 may include a recess 72 (FIGS. 3 and 8) having an opening 74 at the opposite axial end of the body 64 as the shaft 62. As shown in FIG. 3, the spring 24 may be partially received within the recess 72 and may be partially received within the recess 38 of the collar 36 of the shaft 18. In this manner, the spring 24 may bias the plunger 22 away from the shaft 18 along the longitudinal axis A1.

As shown in FIGS. 2, 3 and 8, the body 64 of the plunger 22 may also include a plurality of resiliently flexible tabs 76 each of which includes a barb 78 disposed at or near a distal end of the tab 76. Each of the barbs 78 includes a ramped surface 80 and a stop surface 82 (FIG. 8). As shown in FIGS. 3 and 8, the barbs 78 can be received in any of the second detents 34 so that interference between the stop surface 82 and one of a plurality of backstop surfaces 84 (i.e., backstop surfaces 84 that define the second detents 34) prevents movement of the plunger 22 along the longitudinal axis A1 toward the shaft 18. The ramped surfaces 80 of the barbs 78 allow the tabs 76 to flex inward (i.e., toward the longitudinal axis A1) to allow the plunger 22 to move along the longitudinal axis A1 away from the shaft 18.

With continued reference to FIGS. 1-10, operation of the fastener cartridge 10 will be described in detail. As described above, the fastener cartridge 10 can (1) simultaneously hold one of the plurality of fasteners 14 in a ready-to-be-driven position and one or more fasteners 14 in standby positions, (2) transmit torque from the driver 12 to the fasteners 14 to drive the fastener 14 in the ready-to-be-driven position into the object, and then (3) automatically advance a subsequent one of fasteners 14 to the ready-to-be-driven position.

As described above, the fastener cartridge 10 may be initial assembled with the predetermined number of fasteners 14 disposed within the fastener chamber 44 (e.g., four fasteners 14 in the configurations shown in the figures), where a first one of the fasteners 14 is initially in the ready-to-be-driven position, as shown in FIG. 3. When the first one of the fasteners 14 is in the ready-to-be-driven position, the barbs 78 on the flexible tabs 76 of the plunger 22 are received in the pair of second detents 34 that is furthest away from the outlet 59 of the fastener housing 20.

With the first one of the fasteners 14 in the ready-to-be-driven position and with the shaft 18 attached to the driver 12, the user can rotate the fastener cartridge 10 via the driver 12 to threadably drive the first one of the fasteners 14 into the selected object (e.g., a machine or apparatus component or a bone or other tissue of a human or animal body). Because the shaft 18 is rotationally fixed relative to the housing 16 and the fastener housing 20, rotation of the shaft 18 (via the driver 12) about the longitudinal axis A1 causes torque to be transmitted to the fasteners 14 (the heads 46 of the fasteners 14 are rotationally keyed to the fastener housing 20 due to the mating geometry of the fastener chamber 44 and the heads 46). Interference between the stop surfaces 82 of the flexible tabs 76 and the backstop surfaces 84 of the detents 34 furthest away from the outlet 59 prevent the plunger 22 and the fasteners 14 from moving axially toward the shaft 18 while the fastener 14 is being driven into the object.

After the first one of the fasteners 14 has been driven into the object to a desired depth, the user may disengage the fastener cartridge 10 from the first one of the fasteners 14 by applying a force (or forces) to deform the lips 60 of the first one of the fasteners 14 to allow the head 46 of the first one of the fasteners 14 to pass entirely through the outlet 59 of the fastener housing 20. Deforming the lips 60 can be accomplished by pulling the fastener cartridge 10 away from the first one of the fasteners 14 (or by rocking the fastener cartridge 10 back and forth relative to the fastener 14 and pulling away from the fastener 14) after the fastener 14 is embedded in the object. This pulling and/or rocking action will case the non-flexible tabs 58 of the fastener housing 20 to deform the lips 60 on the first one of the fasteners 14 to allow the fastener cartridge 10 to be separated from the first one of the fasteners 14. Such retention of the fastener 14 in the ready-to-be-driven position and such deliberate steps to separate the fastener 14 from the fastener cartridge 10 reduces or eliminates inadvertent separation of the fastener 14 from the fastener cartridge 10, thereby reducing or eliminating dropped and lost fasteners 14.

As the fastener cartridge 10 is separated from the first one of the fasteners 14, a second one of the fasteners 14 (i.e., the fastener 14 that was disposed immediately behind the first one of the fasteners 14 in FIG. 3) is automatically pushed from the standby position into the ready-to-be-driven position by the plunger 22. That is, as the first one of the fasteners 14 is separating from the fastener cartridge 10, the spring 24 can force the plunger 22 toward the outlet 59 of the fastener housing 20, thereby advancing the second one of the fasteners 14 through the fastener chamber 44 until the lips 60 on the second one of the fasteners 14 abut the non-flexible tabs 58 at the outlet 59 of the fastener housing 20. When the second one of the fasteners 14 is in the ready-to-be-driven position (i.e., when the lips 60 of the second one of the fasteners 14 are contacting the non-flexible tabs 58), the barbs 78 on the flexible tabs 76 of the plunger 22 are received into the pair of second detents 34 that are the second furthest pair from the outlet 59 of the fastener housing 20 (as shown in FIG. 8).

With the second one of the fasteners 14 is in the ready-to-be-driven position, the user can drive the second one of the fasteners 14 into the object and then separate the fastener cartridge 10 from the second one of the fasteners 14 in the manner described above. As the fastener cartridge 10 is being separated from the second one of the fasteners 14, the third one of the fasteners 14 will be automatically advancing from the standby position to the ready-to-be-driven position. The above process can be repeated to drive the third one of the fasteners 14 into the object and advance and drive the fourth one of the fasteners 14, as desired.

As described above, the fasteners 14 are advanced from the standby position to the ready-to-be-driven position automatically. That is, as fastener 14 is separated from the fastener cartridge 10, the next fastener 14 is automatically advanced to the ready-to-be-driven position without any interaction from the user. That is, the user need not take any affirmative steps to cause the next fastener 14 to advance to the ready-to-be-driven position.

Once the last of the predetermined number of fasteners 14 has been driven into the object and separated from the fastener cartridge 10, the plunger 22 may automatically advance (under the force of the spring 24) to the driver position shown in FIGS. 9 and 10. In the driver position, the tip 66 of the plunger 22 protrudes out of the outlet 59 of the fastener housing 20, and the barbs 78 of the flexible tabs 76 of the plunger 22 are received in the pair of second detents 34 that are closest to the outlet 59 of the fastener housing. Interference between the stop surfaces 82 of the barbs 78 and the backstop surfaces 84 prevent movement of the plunger 22 toward the shaft 18. Furthermore, because the diameter of the body 64 of plunger 22 is too large to fit into the fastener chamber 44, the body 64 is retained in the cavity 26 of the housing 16.

When the plunger 22 is in the driver position shown in FIGS. 9 and 10, the fastener cartridge 10 can function as a standard screwdriver and can be used to drive any fastener 14a (not just fasteners configured like the fasteners 14 described above). For example, when the plunger 22 is in the driver position, the tip 66 of the plunger 22 can engage the screw 14a from a screw dial or tray or the screw 14a can be manually loaded onto the tip 66. Because the tip 66 remains rotationally keyed to the fastener chamber 44 in the driver position, the plunger 22 torque applied to the shaft 18 via the driver 12 can be transmitted to the screw 14a via the plunger 22 (rather than the torque from the shaft 18 being transmitted to the fasteners 14 by the fastener housing 20 via the geometry of the fastener chamber 44 when the plunger 22 is in one of the fastener-advancing positions shown in FIGS. 3 and 8, for example).

Figure 11:
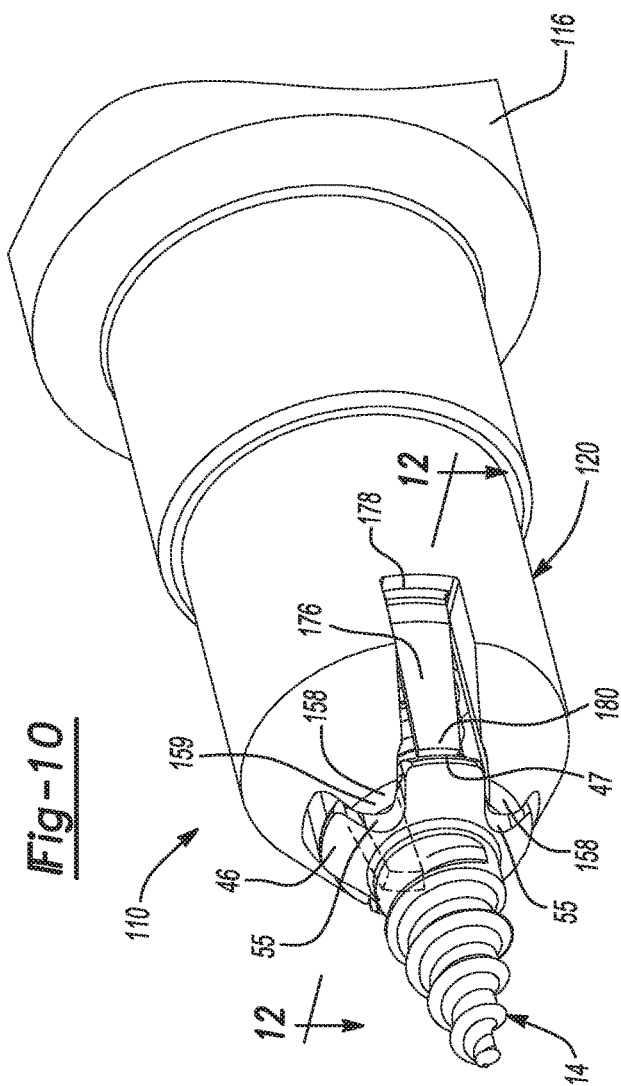
FIG. 11 is a partial perspective view of another fastener cartridge with another fastener housing according to the principles of the present disclosure.
Figure 12:
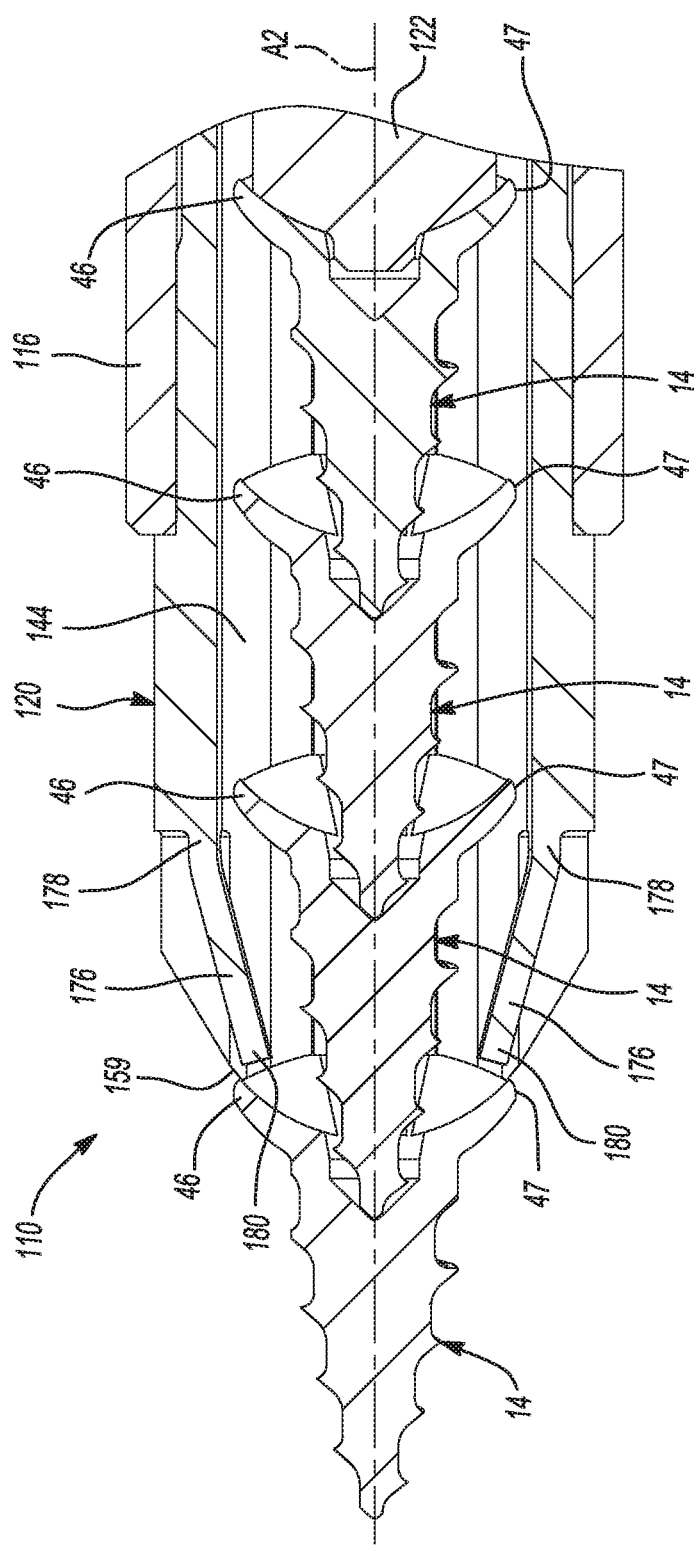
FIG. 12 is a partial cross-sectional view of a plurality of fasteners and the fastener housing of FIG. 11.

Another fastener cartridge 110 is partially depicted in FIGS. 11 and 12 that can be used to hold and drive a predetermined number of the fasteners 14 in a manner similar to the fastener cartridge 10 described above. The structure and function of the fastener cartridge 110 may be similar or identical to that of the fastener cartridge 10, apart from the exceptions described below and/or shown in the figures. Therefore, some similar features will not be described again in detail.

The fastener cartridge 110 may include a main housing 116, a shaft (not shown), a fastener housing 120, a plunger 122 (FIG. 12) and a spring (not shown). The shaft of the fastener cartridge 110 may be similar or identical to the shaft 18 described above and can be operatively coupled to a powered or manual driver. The housing 116 may be similar or identical to the housing 16 described above, except that the housing 116 might not include the second detents 34. The plunger 122 may be similar to the plunger 22 described above, except that the plunger 122 might not include the flexible tabs 76. The spring of the fastener cartridge 110 may be similar or identical to the spring 24 described above.

The fastener housing 120 may be similar or identical to the fastener housing 20 described above, except that the fastener housing 120 may include resiliently flexible tabs 176 that prevent the fastener 14 in the ready-to-be-driven position from being pushed back into a fastener chamber 144 of the fastener housing 120. Because the flexible tabs 176 prevent the fastener 14 in the ready-to-be-driven position from being pushed back into the fastener chamber 144, the fasteners 14 in the standby positions and the plunger 122 are prevented from being pushed toward the shaft of the fastener cartridge 110.

The flexible tabs 176 include a fixed end 178 and a free end 180 and extend from the fixed end 178 in an axial direction (along a longitudinal axis A2 of the fastener housing 120) toward an outlet 159 of the fastener chamber 144 and radially inward toward the longitudinal axis A2. The flexible tabs 176 are in their nominal, at-rest positions when one of the fasteners 14 is in the ready-to-be-driven position (i.e., where non-flexible tabs 158 similar or identical to non-flexible tabs 58 are received in recesses 55 of the fastener 14 in the ready-to-be-driven position), as shown in FIGS. 11 and 12. When the flexible tabs 176 are in their nominal, at-rest positions, the free ends 180 of the flexible tabs 176 are disposed radially inward relative to a radially outermost periphery 49 of the head 46 of the fastener 14 in the ready-to-be-driven position. Therefore, interference between the free ends 180 of the tabs 176 and the head 46 of the fastener 14 in the ready-to-be-driven position prevents the fastener 14 in the ready-to-be-driven position from being pushed back into the fastener chamber 144.

After the fastener 14 in the ready-to-be-driven position is driven in the object and as the fastener cartridge 110 is being separated from that fastener 14, the plunger 122 pushes the next fastener 14 from the standby position to the ready-to-be-driven position, as described above. As the fastener 14 is being advanced from the standby position to the ready-to-be-driven position, the head 46 of the fastener 14 can force the free ends 180 of the tabs 176 to flex radially outward (away from the longitudinal axis A2) as the head 46 of the fastener 14 passes between the free ends 180 to the ready-to-be-driven position.

While not shown in FIGS. 11 and 12, the plunger 122 could include detents that interface with the flexible tabs 176 to retain the plunger in a driver position like the driver position of the plunger 22 shown in FIGS. 9 and 10.

Referring now to FIGS. 13 and 14, another fastener cartridge 210 is provided that may be used in conjunction with the driver 12 to hold and drive a predetermined number of fasteners 14 in a manner similar to the fastener cartridge 10, 110 described above. The structure and function of the fastener cartridge 210 may be similar or identical to that of the fastener cartridge 10, 110, apart from the exceptions described below and/or shown in the figures. Therefore, some similar features will not be described again in detail.

The fastener cartridge 210 may include a main housing 216, a shaft 218, a fastener housing 220, a plunger 222, a spring 224 and a backstop component 225. In the configuration shown in FIGS. 13 and 14, the housing 216 and the shaft 218 are integrally formed as a single unitary body, however, in some configurations, the housing 216 and the shaft 218 may be separate components fixedly attached to each other. The housing 216 includes a cavity 226 in which the spring 224 and the plunger 222 are movably disposed. A first end 223 of the spring 224 abuts a first end 227 of the cavity 226 adjacent the shaft 218. A second end 229 of the spring 224 abuts a flange 231 of the plunger 222, thereby biasing the plunger 222 away from the shaft 218 along a longitudinal axis A3 of the fastener cartridge 210.

The fastener housing 220 may include a tapered first end 232 and a second end 234. A recess 236 may be formed in the second end 234 and a fastener chamber 244 may extend from the recess 236 through the first end 232. The fastener chamber 244 may be shaped similarly or identically to the fastener chamber 44 described above to rotationally key the fasteners 14 relative to the fastener housing 220. A diameter of the recess 236 may be larger than the width of the fastener chamber 244 such that a generally annular ledge 246 is formed at an axial end of the recess 236. The second end 234 of the fastener housing 220 may include one or more barbs 248 that may snap into engagement with one or more grooves or detents 250 in the housing 216 to fix the fastener housing 220 relative to the housing 216. It will be appreciated that the fastener housing 220 could be fixed relative to the housing 216 in any other suitable manner (e.g., press fit, welding, etc.)

The plunger 222 may include a shaft 252 extending along the longitudinal axis A3 from the flange 231 and is axially movable along the longitudinal axis A3 relative to the housing 216 and fastener housing 220. The shaft 252 may include a tip 254 that is shaped to engage one or more of the slots 54 (FIG. 4) of the fasteners 14, like the tip 66 of the plunger 22 described above. Also like the tip 66, the tip 254 is also shaped to be slidably and non-rotatably received in the fastener chamber 244. The shaft 252 may also include a plurality of detents 256 arranged along the length of the shaft 252 between the tip 254 and the flange 231. The detents 256 could be annular detents that extend around the longitudinal axis A3.

The backstop component 225 can be an annular member disposed within the recess 236 of the fastener housing 220 and abutting the ledge 246 and an axial end of the housing 216. The backstop component 225 may include an outer body 258 and one or more resiliently flexible tabs 260. The flexible tab 260 includes include a fixed end 262 and a free end 264 and extends from the fixed end 262 in a radially inward direction toward the longitudinal axis A3 and in an axial direction (along the longitudinal axis A3) toward an outlet 259 of the fastener chamber 244. The flexible tab 260 is biased radially inward so that the free end 264 springs into the detents 256 as the detents 256 are moved into alignment with the free end 264. The detents 256 each include a ramped surface 266 and a stop surface 268 that are shaped to allow the detents 256 to freely move past the free end 264 when the plunger 222 is moving toward the outlet 259 of the fastener housing 220 and prevent the detents 256 from moving past the free end 264 when the plunger 222 is moving in the opposite direction. In this manner, the backstop component 225 and the detents 256 allow the plunger 222 to advance the fasteners 14 from the standby positions toward and into the ready-to-be-driven position, while preventing the fastener 14 in the ready-to-be-driven position from being pushed back into the fastener chamber 244 toward the shaft 218.

Referring now to FIGS. 15-18, another fastener cartridge 310 is provided that may be used in conjunction with the driver 12 to hold and drive a predetermined number of fasteners 314 in a manner similar to the fastener cartridge 10, 110, 210 described above. The structure and function of the fastener cartridge 310 may be similar or identical to that of the fastener cartridge 10, 110, 210, apart from the exceptions described below and/or shown in the figures. Therefore, some similar features will not be described again in detail.

The fastener cartridge 310 may include a main housing 316, a shaft 318, a fastener housing 320, a plunger 322, a spring 324 and a backstop component 325. In the configuration shown in FIGS. 15-18, the housing 316 and the shaft 318 are integrally formed as a single unitary body, however, in some configurations, the housing 316 and the shaft 318 may be separate components that are attachable to each other. The housing 316 includes a cavity 326 in which the spring 324 and the plunger 322 are movably disposed. A first end 323 of the spring 324 abuts a first end 327 of the cavity 326 adjacent the shaft 318. A second end 329 of the spring 324 abuts a flange 331 of the plunger 322, thereby biasing the plunger 322 away from the shaft 318 along a longitudinal axis A4 of the fastener cartridge 310.

The fastener housing 320 may be attached to and extend from a first axial end 328 of the housing 316. In some configurations, the fastener housing 320 may engage the housing 316 by a snap fit (e.g., tabs 390 of the fastener housing 320 may snap into recesses 333 of the housing 316). The fastener housing 320 may include a tapered first end 332 and a second end 334. A recess 336 may be formed in the second end 334 and a fastener chamber 344 may extend from the recess 336 through the first end 332. A diameter of the recess 336 may be larger than the width of the fastener chamber 344 such that a generally annular ledge 347 (FIG. 18) is formed at an axial end of the recess 336. As described above with respect to the fastener chamber 44, the fastener chamber 344 may be shaped to rotationally key the fasteners 314 relative to the fastener housing 320. As shown in FIG. 18, the fastener housing 320 may include a pair of protrusions 345 that extend into the fastener chamber 344 to engage recesses 355 (similar to recesses 55) of the fasteners 314 to prevent relative rotation between the fasteners 314 and the fastener housing 320 while allowing the fasteners 314 to move axially (along axis A4) relative to the fastener housing 320.

As shown in FIGS. 15 and 16, the first end 332 of the fastener housing 320 may include a plurality of non-flexible tabs 358 that extend radially into the fastener chamber 344 at an outlet of the fastener chamber 344. Each of the non-flexible tabs 358 may be received in a corresponding one of the recesses 355 in the fastener 314 that is in the ready-to-be-driven position (i.e., the fastener 314 that is extending out of the fastener chamber 344 and whose tip 352 is pointed away from the fastener cartridge 310). Interference between the non-flexible tabs 358 and lips (e.g., lips similar or identical to lips 60) of the ready-to-be-driven fastener 314 prevents inadvertent disengagement between the fastener cartridge 310 and the ready-to-be-driven fastener 314.

The plunger 322 may include a shaft 353 extending along the longitudinal axis A4 from the flange 331 and is axially movable along the longitudinal axis A4 relative to the housing 316 and fastener housing 320. The shaft 353 may include a tip 351 that is shaped to engage one or more of the slots 354 (FIG. 18) of the fasteners 314, like the tip 66 of the plunger 22 described above.

The backstop component 325 may be a generally tubular member having a collar 370, a cylindrical stem 374 and a plurality of resiliently flexible tabs 376. The collar 370 may be received in the recess 336 of the fastener housing 320 and may be axially fixed therein between the fastener housing 320 and the housing 316. The tabs 376 prevent the fastener 314 in the ready-to-be-driven position from being pushed back into a fastener chamber 344. Because the flexible tabs 376 prevent the fastener 314 in the ready-to-be-driven position from being pushed back into the fastener chamber 344, the fasteners 314 in the standby positions and the plunger 322 are prevented from being pushed toward the shaft 318 of the fastener cartridge 310.

The flexible tabs 376 include a fixed end 378 (attached to the stem 374) and a free end 380 and extend from the fixed end 378 in an axial direction (along a longitudinal axis A4 of the fastener housing 320) toward an outlet 359 of the fastener chamber 344 and radially inward toward the longitudinal axis A4. The flexible tabs 376 are in their nominal, at-rest positions when one of the fasteners 314 is in the ready-to-be-driven position, as shown in FIGS. 15 and 17. When the flexible tabs 376 are in their nominal, at-rest positions, the free ends 380 of the flexible tabs 376 are disposed radially inward relative to a radially outermost periphery 349 of the head 346 of the fastener 314 in the ready-to-be-driven position. Therefore, interference between the free ends 380 of the tabs 376 and the head 346 of the fastener 314 in the ready-to-be-driven position prevents the fastener 314 in the ready-to-be-driven position from being pushed back into the fastener chamber 344.

After the fastener 314 in the ready-to-be-driven position is driven in the object and as the fastener cartridge 310 is being separated from that fastener 314, the plunger 322 pushes the next fastener 314 from the standby position to the ready-to-be-driven position, as described above. As the fastener 314 is being advanced from the standby position to the ready-to-be-driven position, the head 346 of the fastener 314 can force the free ends 380 of the tabs 376 to flex radially outward (away from the longitudinal axis A4) as the head 346 of the fastener 314 passes between the free ends 380 to the ready-to-be-driven position.

After all of the fasteners 314 have been driven into the object (i.e., after all of the fasteners 314 have been separated from the fastener cartridge 310), tip 351 of the plunger 322 may protrude out of the outlet of the fastener housing 320 (i.e., the plunger 322 may be in a driver position similar to the driver position described above and shown in FIG. 9). When the plunger 322 is in the driver position, the tabs 376 of the backstop component 325 may abut ledges 379 on the tip 351 to prevent the plunger 322 from being unintentionally pushed back into the fastener chamber 344 while the fastener cartridge 310 is being used in the driver position to drive fasteners.

In some configurations, after all of the fasteners 314 have been driven into the object (i.e., after all of the fasteners 314 have been separated from the fastener cartridge 310), the fastener housing 320 and backstop component 325 may be removed from the housing 316 to reload more fasteners into the fastener channel 344. Thereafter, the backstop component 325 and fastener housing 320 may be reattached to the housing 316 to drive the reloaded fasteners as described above.

Figure 19:
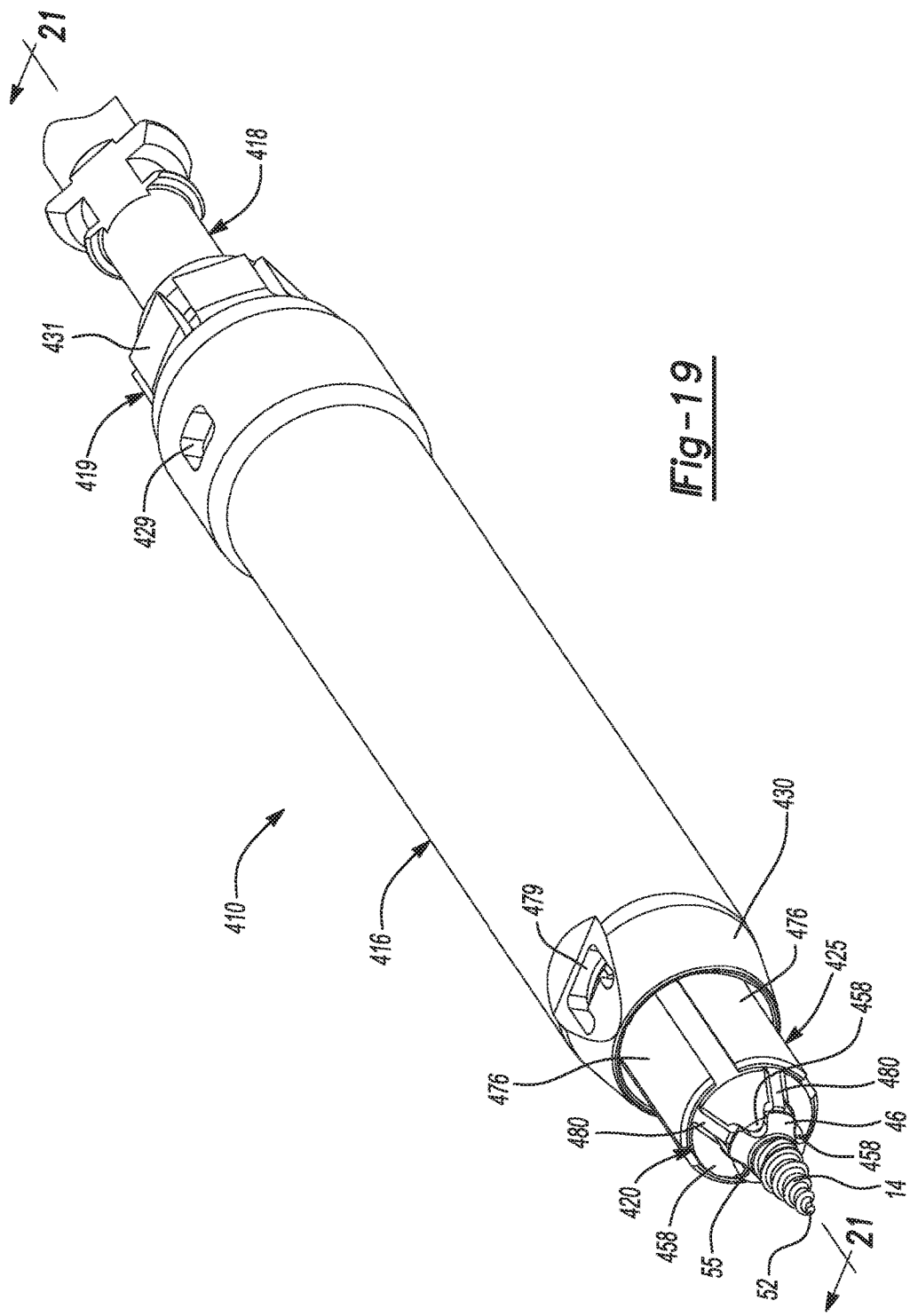
FIG. 19 is a perspective view of another fastener cartridge according to the principles of the present disclosure.
Figure 20:
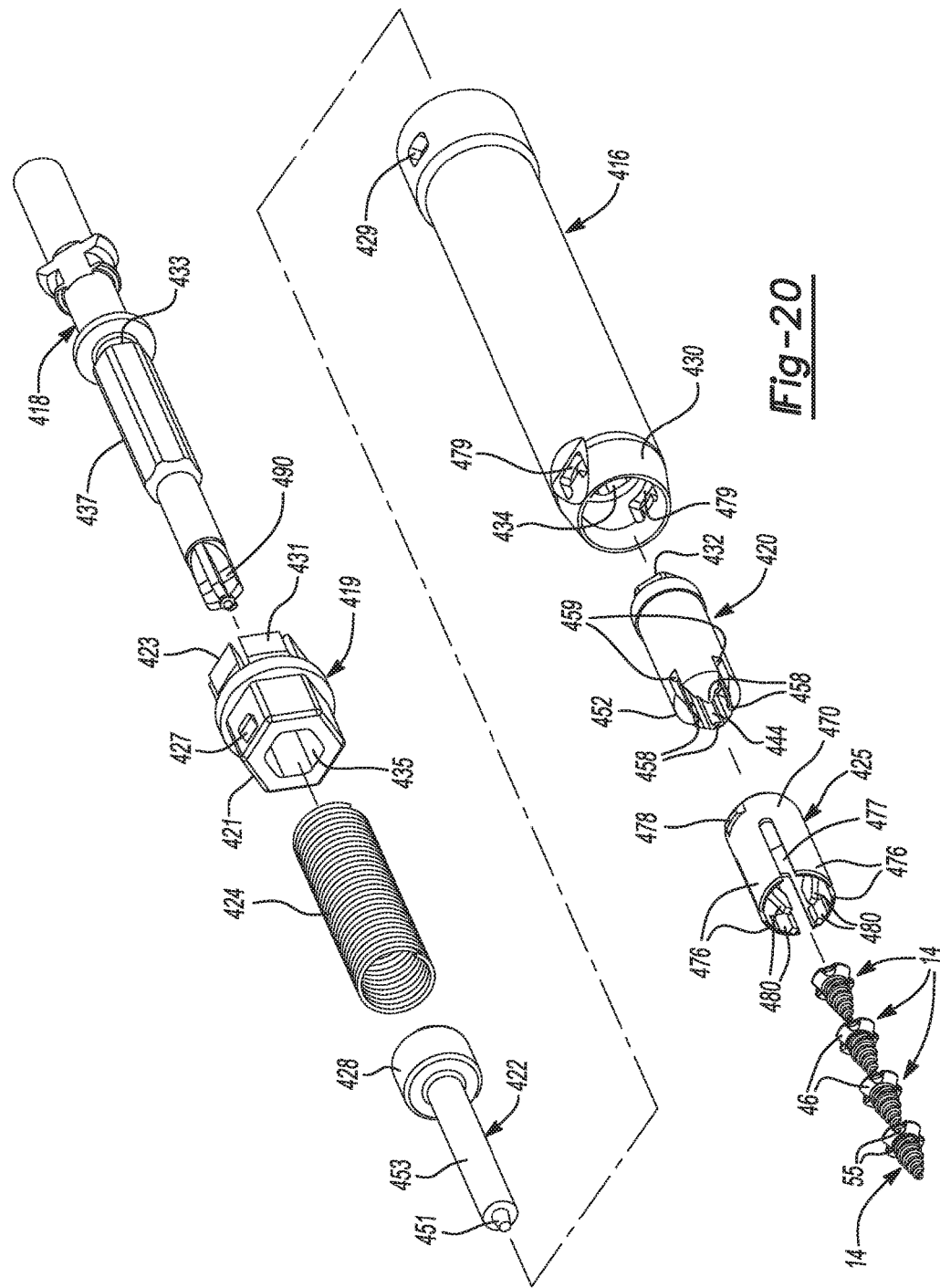
FIG. 20 is an exploded perspective view of the fastener cartridge of FIG. 19.
Figure 21:
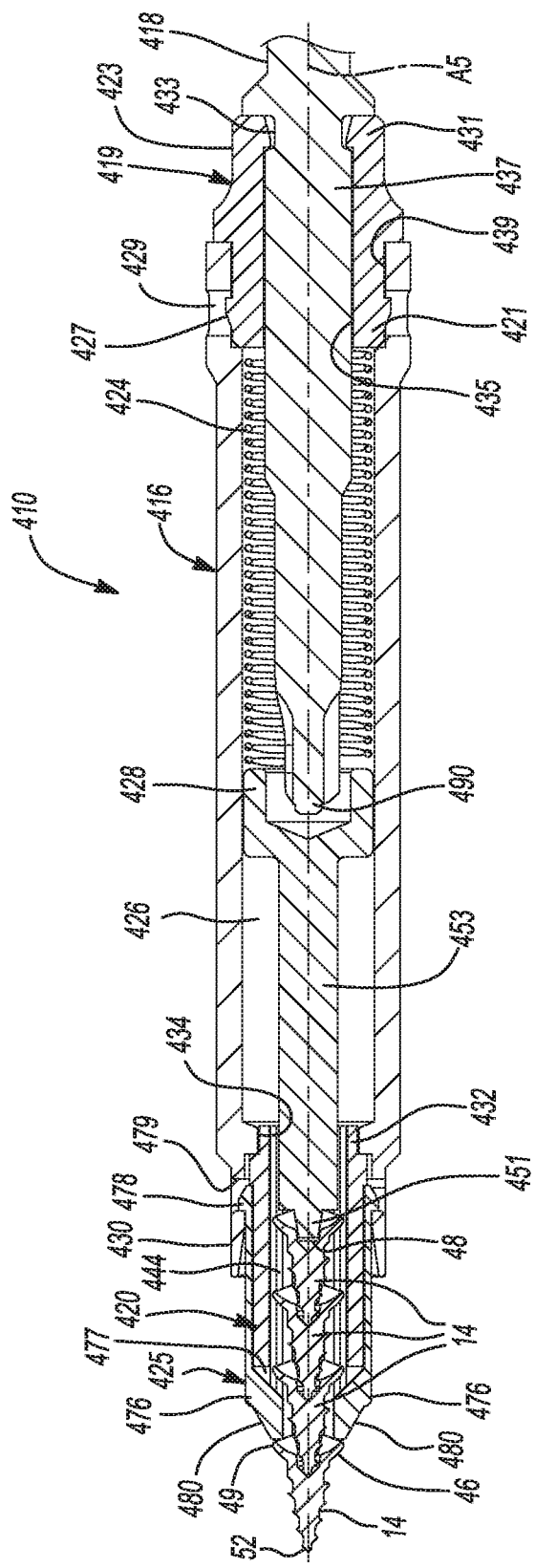
FIG. 21 is a cross-sectional view of the fastener cartridge of FIG. 19.

Referring now to FIGS. 19-21, another fastener cartridge 410 is provided that may be used in conjunction with the driver 12 to hold and drive a predetermined number of fasteners 14 in a manner similar to the fastener cartridge 10, 110, 210, 310 described above. The structure and function of the fastener cartridge 410 may be similar or identical to that of the fastener cartridge 10, 110, 210, 310, apart from the exceptions described below and/or shown in the figures. Therefore, some similar features will not be described again in detail.

The fastener cartridge 410 may include a main housing 416, a shaft 418, an adaptor 419, a fastener housing 420, a plunger 422, a spring 424 and a backstop component 425. The housing 416 and the shaft 418 are separate components that are attachable to each other via the adaptor 419. The adaptor 419 includes a first end 421 that is received into and removably engages the housing 416 and second end 423 that receives and removably engages the shaft 418. The first end 421 may include one or more barbs 427 that snap into recesses 429 in the housing 416. The second end 423 may include a plurality of flexible, barbed tabs 431 that snap into an annular recess 433 in the shaft 418. The adaptor 419 may include an aperture 435 that extend entirely through the first and second ends 421, 423 and has a shape that corresponds to the shape of a mating portion 437 of the shaft 418. Each of the aperture 435 and mating portion 437 include one or more flat surfaces (shown in FIG. 20) that mate with each other to prevent relative rotation between the shaft 418 and the adaptor 419. The first end 421 of the adaptor 419 may also include one or more flat surfaces (shown in FIG. 20) that mate with one or more flat surfaces defining a recess 439 (FIG. 21) in the end of the housing 416. The engagement between the adaptor 419 and the housing 416 and between the adaptor 419 and the shaft 418 is strong enough to keep the shaft 418 and housing 416 fixed to each other during operation of the drill 12 and fastener cartridge 410 while still allowing a user to manually pull the housing 416 and adaptor 419 off of the shaft 418 and/or pull the housing 416 off of the adaptor 419 when desired.

The housing 416 includes a cavity 426 in which the spring 424 and the plunger 422 are movably disposed. One end of the spring 424 abuts the first end 421 of the adaptor 419, and the other end of the spring 424 abuts a flange 428 of the plunger 422, thereby biasing the plunger 422 away from the shaft 418 along a longitudinal axis A5 of the fastener cartridge 410.

The fastener housing 420 may be attached to and extend from a first axial end 430 of the housing 416. In some configurations, the fastener housing 420 may include a key portion 432 (having one or more flat surfaces) that is received in a keyway 434 (having one or more flat surfaces) of the housing 416 to prevent relative rotation between the housing 416 and the fastener housing 420. The fastener housing 420 may include a fastener chamber 444 extending axially therethrough. As described above with respect to the fastener chamber 44, the fastener chamber 444 may be shaped to rotationally key the fasteners 14 relative to the fastener housing 420. That is, the fastener chamber 444 is shaped so that fasteners 14 are rotationally fixed to the fastener housing 420 while allowing the fasteners 14 to move axially (along axis A5) relative to the fastener housing 420.

As shown in FIGS. 19 and 20, the first end 452 of the fastener housing 420 may include a plurality of non-flexible tabs 458 that extend radially into the fastener chamber 444 at an outlet of the fastener chamber 444. A slot 459 (FIG. 20) may be disposed between each pair of adjacent tabs 458.

Each of the non-flexible tabs 458 may be received in a corresponding one of the recesses 55 in the fastener 14 that is in the ready-to-be-driven position (i.e., the fastener 14 that is extending out of the fastener chamber 444 and whose tip 52 is pointed away from the fastener cartridge 410). Interference between the non-flexible tabs 458 and lips 60 of the ready-to-be-driven fastener 14 prevents inadvertent disengagement between the fastener cartridge 410 and the ready-to-be-driven fastener 14.

The plunger 422 may include a cylindrical shaft 453 extending along the longitudinal axis A5 from the flange 428 and is axially movable along the longitudinal axis A5 relative to the housing 416 and fastener housing 420. The shaft 453 may include a tip 451 that is shaped and sized to fit within the recess 48 of one of the fasteners 14 (as shown in FIG. 21).

The backstop component 425 may be a generally tubular member having a base 470, a plurality of resiliently flexible tabs 476 and a cavity 477 extending axially through the backstop component 425. The base 470 may be received in the end 430 of the housing 416 and may include barbs 478 that snap into recesses 479 in the housing 416. Each of the tabs 476 may include a cleat 480 extending radially inwardly from distal ends of the tabs 476. The fastener housing 420 may be received in the cavity 477 of the backstop component 425 and the cleats 480 may be extend into the slots 459 of the fastener housing 420. The tabs 476 prevent the fastener 14 in the ready-to-be-driven position from being pushed back into the fastener chamber 444. Because the flexible tabs 476 prevent the fastener 14 in the ready-to-be-driven position from being pushed back into the fastener chamber 444, the fasteners 14 in the standby positions and the plunger 422 are prevented from being pushed toward the shaft 418 of the fastener cartridge 410.

The flexible tabs 476 are in their nominal, at-rest positions when one of the fasteners 14 is in the ready-to-be-driven position, as shown in FIGS. 19 and 21. When the flexible tabs 476 are in their nominal, at-rest positions, the radially innermost ends of the cleats 480 of the flexible tabs 476 are disposed radially inward relative to a radially outermost periphery 49 of the head 46 of the fastener 14 in the ready-to-be-driven position (as shown in FIG. 21). Therefore, interference between the tabs 476 and the head 46 of the fastener 14 in the ready-to-be-driven position prevents the fastener 14 in the ready-to-be-driven position from being pushed back into the fastener chamber 444.

After the fastener 14 in the ready-to-be-driven position is driven in the object and as the fastener cartridge 410 is being separated from that fastener 14, the plunger 422 pushes the next fastener 14 from the standby position to the ready-to-be-driven position, as described above. As the fastener 14 is being advanced from the standby position to the ready-to-be-driven position, the head 46 of the fastener 14 can force the tabs 476 to flex radially outward (away from the longitudinal axis A5) as the head 46 of the fastener 14 passes between the tabs 476 to the ready-to-be-driven position.

After all of the fasteners 14 have been driven into the object (i.e., after all of the fasteners 14 have been separated from the fastener cartridge 410), the adaptor 419 and housing 416 (along with the fastener housing 420, plunger 422, spring 424, and backstop component 425) may be removed from the shaft 418. Thereafter, a driver tip 490 of the shaft 418 (which is shaped to be received in slots 54 of fasteners 14) can be used to engage drive fasteners one at a time. Further, the housing 416 can be reloaded with additional fasteners or a preloaded housing 416 can be reattached to the shaft 418 via the adaptor 419.

Figure 22:
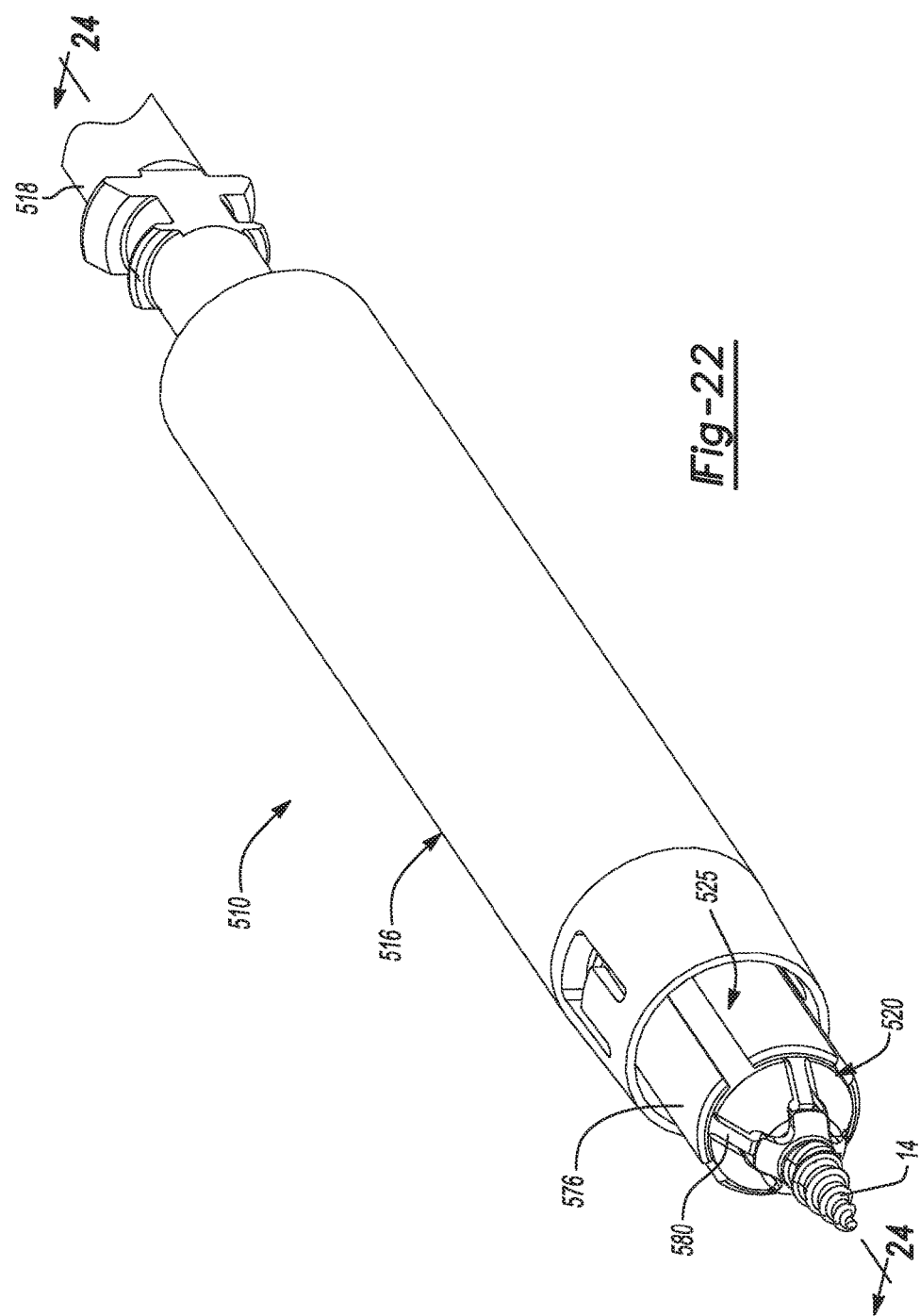
FIG. 22 is a perspective view of another fastener cartridge according to the principles of the present disclosure.
Figure 23:
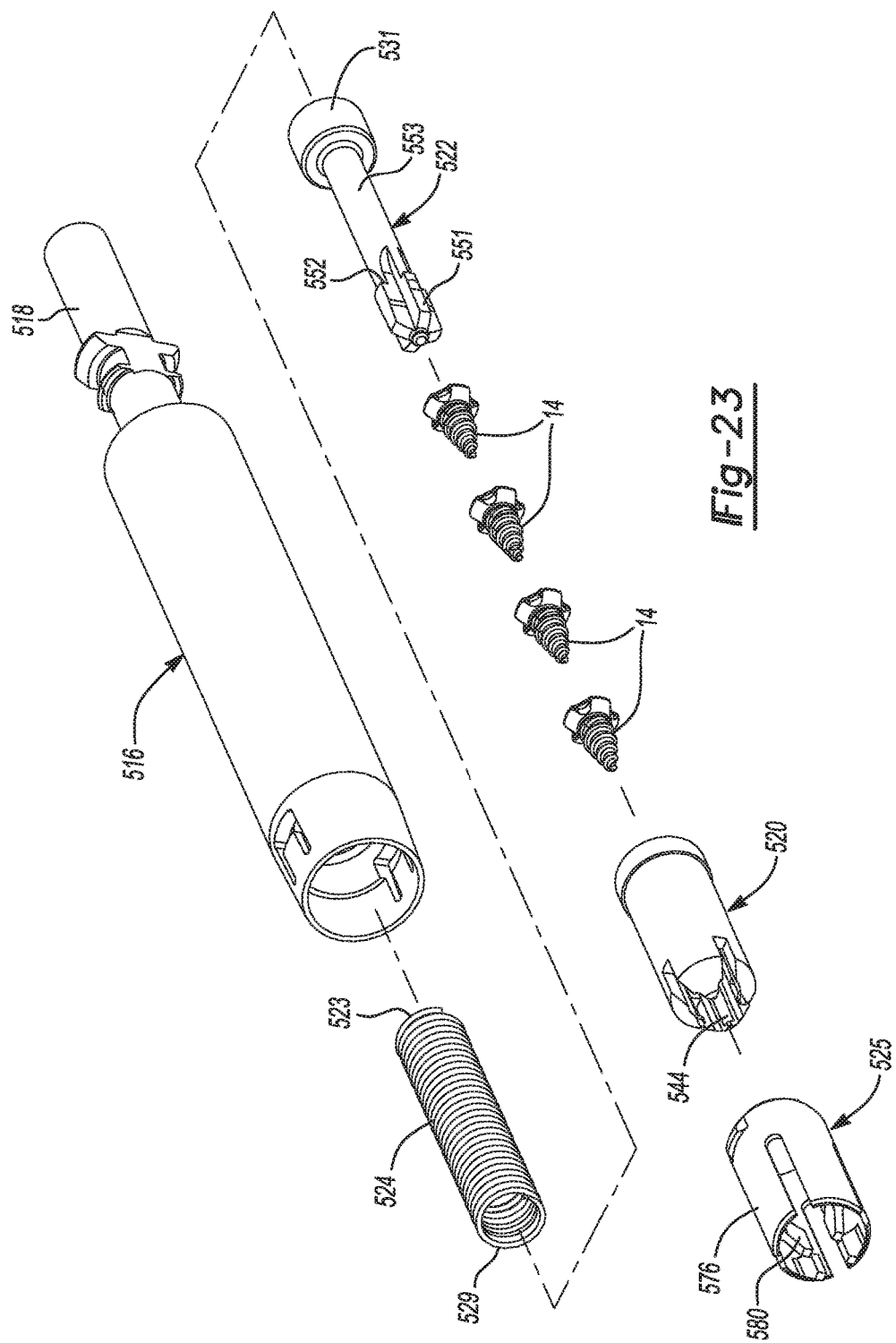
FIG. 23 is an exploded perspective view of the fastener cartridge of FIG. 22.
Figure 24:
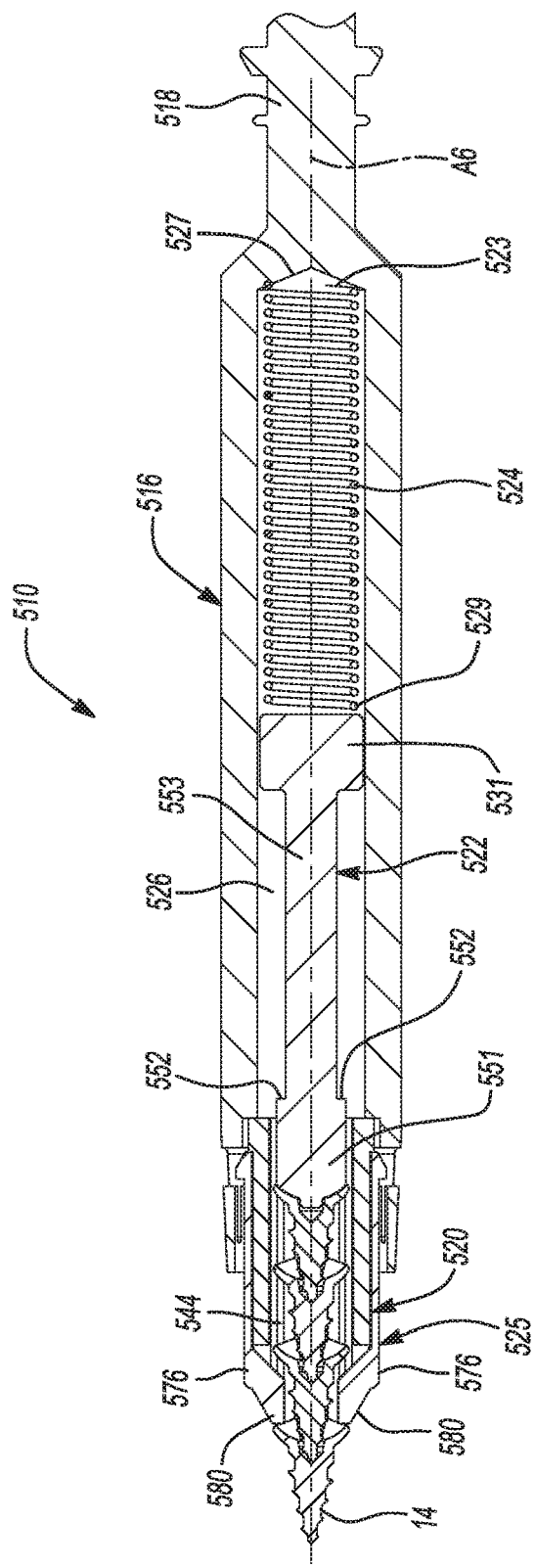
FIG. 24 is a cross-sectional view of the fastener cartridge of FIG. 22.

Referring now to FIGS. 22-24, another fastener cartridge 510 is provided that may be used in conjunction with the driver 12 to hold and drive a predetermined number of fasteners 14 in a manner similar to the fastener cartridge 410 described above. The structure and function of the fastener cartridge 510 may be similar or identical to that of the fastener cartridge 410, apart from the exceptions described below and/or shown in the figures. Therefore, some similar features will not be described again in detail.

The fastener cartridge 510 may include a main housing 516, a shaft 518, a fastener housing 520, a plunger 522, a spring 524 and a backstop component 525. In the configuration shown in FIGS. 22-24, the housing 516 and the shaft 518 are integrally formed as a single unitary body.

The housing 516 includes a cavity 526 in which the spring 524 and the plunger 522 are movably disposed. A first end 523 of the spring 524 abuts a first end 527 of the cavity 526 adjacent the shaft 518. A second end 529 of the spring 524 abuts a flange 531 of the plunger 522, thereby biasing the plunger 522 away from the shaft 518 along a longitudinal axis A6 of the fastener cartridge 510. The plunger 522 may include a shaft 553 extending along the longitudinal axis A6 from the flange 531. The shaft 553 may include a tip 551 that is shaped to engage one or more of the slots of the fasteners 14, like the tip 66 of the plunger 22 described above.

The housing 516 may be otherwise similar or identical to the housing 416 described above. Furthermore, the fastener housing 520 and backstop component 525 may be similar or identical to the fastener housing 420 and backstop component 425 described above.

As described above, tabs 576 and cleats 580 of the backstop component 525 prevent the fastener 14 in the ready-to-be-driven position from being pushed back into a fastener chamber 544 of the fastener housing 520. The flexible tabs 576 are in their nominal, at-rest positions when one of the fasteners 14 is in the ready-to-be-driven position, as shown in FIGS. 22 and 24. When the flexible tabs 576 are in their nominal, at-rest positions, the radially innermost ends of the cleats 580 of the flexible tabs 576 are disposed radially inward relative to a radially outermost periphery 49 of the head 46 of the fastener 14 in the ready-to-be-driven position (as shown in FIG. 24). Therefore, interference between the tabs 576 and the head 46 of the fastener 14 in the ready-to-be-driven position prevents the fastener 14 in the ready-to-be-driven position from being pushed back into the fastener chamber 544.

After the fastener 14 in the ready-to-be-driven position is driven in the object and as the fastener cartridge 510 is being separated from that fastener 14, the plunger 522 pushes the next fastener 14 from the standby position to the ready-to-be-driven position, as described above. As the fastener 14 is being advanced from the standby position to the ready-to-be-driven position, the head 46 of the fastener 14 can force the tabs 576 to flex radially outward (away from the longitudinal axis A6) as the head 46 of the fastener 14 passes between the tabs 576 to the ready-to-be-driven position.

After all of the fasteners 14 have been driven into the object (i.e., after all of the fasteners 14 have been separated from the fastener cartridge 510), tip 551 of the plunger 522 may protrude out of the outlet of the fastener housing 520 (i.e., the plunger 522 may be in a driver position similar to the driver position described above and shown in FIG. 9). When the plunger 522 is in the driver position, the cleats 580 of the backstop component 525 may abut ledges 552 on the tip 551 to prevent the plunger 522 from being unintentionally pushed back into the fastener chamber 544 while the fastener cartridge 510 is being used in the driver position to drive fasteners.

Referring now to FIGS. 25-32B, another fastener cartridge 610 is provided that may be used in conjunction with the driver 12 to hold and drive a predetermined number of fasteners 613 in a manner similar to the fastener cartridge 10, 110, 210, 310, 410 described above. The structure and function of the fastener cartridge 610 may be similar or identical to that of the fastener cartridge 10, 110, 210, 310, 410, apart from the exceptions described below and/or shown in the figures. Therefore, some similar features will not be described again in detail.

The fastener cartridge 610 shown in FIGS. 25-28 can be a one-time use fastener cartridge. The fastener cartridge 610 can receive shaft 618 associated with the driver 12. In the configuration shown in the figures, the shaft 618 includes protrusions 42 that can be received in the driver 12 to rotationally fix the shaft 618 relative to the driver 12 (thereby rotationally fixing the entire fastener cartridge 610 relative to the driver 12). It will be appreciated that the shaft 618 could include other features in addition to or instead of the protrusions 642 to engage the driver 12.

Figure 25:
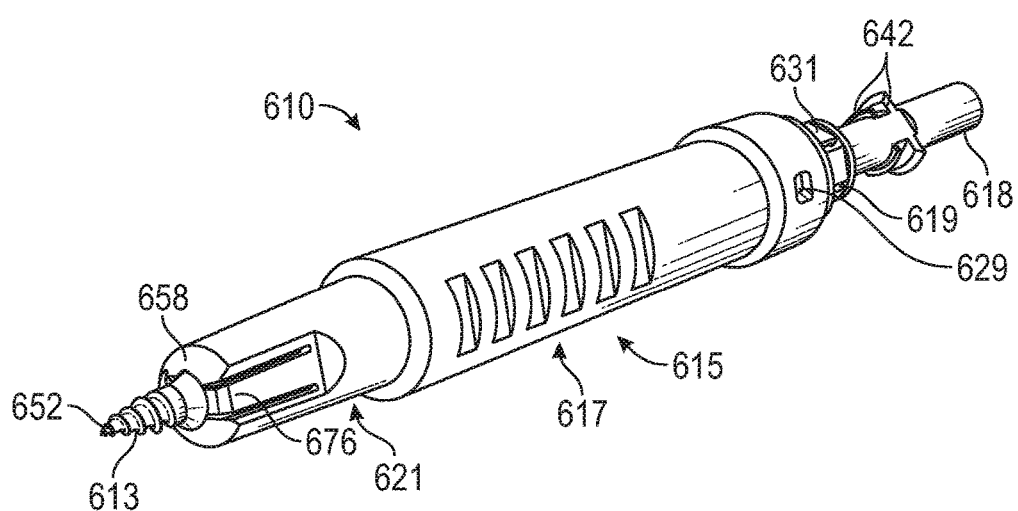
FIG. 25 is a perspective view of another fastener cartridge according to the principles of the present disclosure.

The fastener cartridge 610 may include a body 615, an adaptor 619, a plunger housing 617, a fastener housing 621, a plunger 622, a spring 624, and a plurality of fasteners 613. As shown in FIG. 25, the fastener cartridge 610 is coupled to the shaft 618. The fastener cartridge 610 and the shaft 618 are separate components that are attachable to each other via the adaptor 619 of the fastener cartridge 610. The adaptor 619 includes a first end 621 that is received into and engages the body 615 and a second end 623 that receives and engages the shaft 618. The first end 621 may include one or more barbs 627 that snap into recesses 629 in the body 615. The second end 623 may include a plurality of flexible, barbed tabs 631 that snap into an annular recess 633 in the shaft 618. The adaptor 619 may include an aperture 635 that extends entirely through the first and second ends 621, 623 and has a shape that corresponds to the shape of a mating portion 637 of the shaft 618. Each of the aperture 635 and mating portion 637 include one or more flat surfaces (shown in FIG. 26) that mate with each other to prevent relative rotation between the shaft 618 and the adaptor 619. The first end 621 of the adaptor 619 may also include one or more flat surfaces (shown in FIG. 26) that mate with one or more flat surfaces defining a recess 639 (FIG. 27) in the end of the body 615.

Referring to FIG. 27, the body 615 includes a cavity 626 in which the spring 624 and the plunger 622 are movably disposed. One end 691 of the spring 624 abuts a surface 693 of the first end 621 of the adaptor 619, and the other end 692 of the spring 624 abuts a flange 628 of the plunger 622, thereby biasing the plunger 622 away from the shaft 618 along a longitudinal axis A5 of the fastener cartridge 610.

Referring to FIG. 26, the body 615 can include depressions 694 on an external surface that can assist a user to in gripping the fastening cartridge 610 when attaching and detaching the fastening cartridge 610 to the shaft 618. As shown, the fastener housing 621 may be formed integral with the plunger housing 617. However, the fastener housing 621 and the plunger housing 617 can also be formed separately and the fastener housing 621 can be attached to and extend from a first axial end 630 of the plunger housing 617.

Referring to FIGS. 27 and 28, the fastener housing 621 includes a fastener chamber 644 extending axially therethrough. As described above with respect to the fastener chamber 44, the fastener chamber 644 can be shaped to rotationally key the fasteners 613 relative to the fastener housing 621. That is, the fastener chamber 644 is shaped so that fasteners 613 are rotationally fixed to the fastener housing 621 while allowing the fasteners 613 to move axially (along axis A5) relative to the fastener housing 621.

A first end of the fastener housing 621 includes a plurality of non-flexible tabs 658 (referred to collectively as "non-flexible table 658) and a plurality of resiliently flexible tabs 676 (referred to collectively as "flexible tabs 676"). In one configuration, the fastener housing 621 can include two non-flexible tabs 658 and two flexible tabs 676. As seen in FIG. 26, a slot 659 can be disposed between each adjacent non-flexible tab 658 and flexible tab 676. That is, adjacent non-flexible tabs 658 and flexible tabs 676 can be separated by the slots 659.

The fastener housing 621 can include a stepped portion 660 along the resiliently flexible tabs 676 such that the thickness of the resiliently flexible tabs 676 is less than the thickness of the non-flexible tabs 658. For example, a diameter of the fastener housing 621 across the two flexible tabs 676 can be less than a diameter of the fastener housing 621 across the two non-flexible tabs 658. The providing the flexible tabs 676 with a smaller thickness can allow the flexible tab 676 to be flexible.

In one configuration, the flexible tabs 676 can be formed separately from the rest of the body 615 and subsequently attached and can be flexible based on a the connection joint where the flexible tab 676 couples to the body 615. Further, the flexible tabs 676 can be formed of a different material from the body 615 and subsequently be attached to the body 615. While the fastening cartridge 610 includes two non-flexible tabs 658 and two flexible tabs 676, the number of non-flexible tabs 658 and flexible tabs 676 do not have to be equal or be equal between each other.

The flexible tabs 676 prevent the fastener 613 in the ready-to-be-driven position from being pushed back into the fastener chamber 644. Because the flexible tabs 676 prevent the fastener 613 in the ready-to-be-driven position from being pushed back into the fastener chamber 644, the fasteners 613 in the standby positions and the plunger 622 are prevented from being pushed toward the shaft 618 of the fastener cartridge 610.

Figure 29:
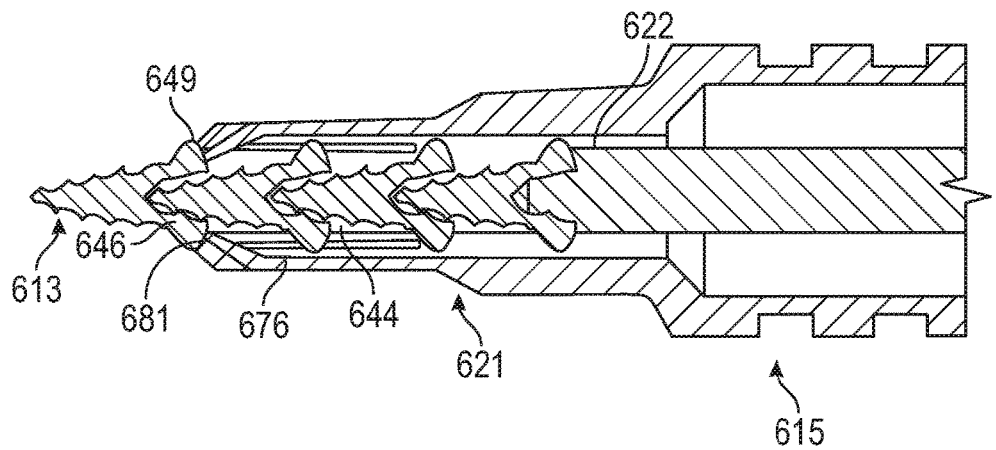
FIG. 29 is a cross-sectional view of a portion of the fastener cartridge of FIG. 25.

The flexible tabs 676 are in their nominal, at-rest positions when one of the fasteners 613 is in the ready-to-be-driven position, as shown in FIGS. 25 and 29. FIG. 29 illustrates a cross-sectional view of a portion of the fastener cartridge 610 in FIG. 25 along the flexible tabs 676. When the flexible tabs 676 are in their nominal, at-rest positions, the radially innermost ends of a protrusion 681 (shown in FIGS. 26 and 30) of the flexible tabs 676 are disposed radially inward relative to a radially outermost periphery 649 of the head 646 of the fastener 613 in the ready-to-be-driven position (as shown in FIG. 29). Therefore, interference between the tabs 676 and the head 646 of the fastener 613 in the ready-to-be-driven position prevents the fastener 613 in the ready-to-be-driven position from being pushed back into the fastener chamber 644.

FIGS. 27, 28 illustrate cross-sectional views of portions of the fastener cartridge 610 in FIG. 25 along the non-flexible tabs 658. Referring to FIGS. 27 and 28, the non-flexible tabs 658 include a projection 661 that extends radially into the fastener chamber 644 at an outlet of the fastener chamber 644. Each of the non-flexible tabs 658 can be received in a corresponding one of the recesses 655 in the fastener 613 that is in the ready-to-be-driven position (i.e., the fastener 613 that is extending out of the fastener chamber 644 and whose tip 652 is pointed away from the fastener cartridge 610. Interference between the non-flexible tabs 658 and lips 660 of the ready-to-be-driven fastener 613 prevents inadvertent disengagement between the fastener cartridge 610 and the ready-to-be-driven fastener 613. In FIG. 27, the shaft 618 is not shown. As seen in FIGS. 27 and 28 the non-flexible tabs 658 are engaging with the lips 660 of the fastener 613 that is in the ready-to-be-driven position to prevent inadvertent disengagement between the fastener cartridge 610 and the ready-to-be-driven fastener 613.

After the first one of the fasteners 613 has been driven into the object to a desired depth, the user may disengage the fastener cartridge 610 from the first one of the fasteners 613 by applying a force (or forces) to deform the lips 660 of the first one of the fasteners 613 to allow the head 646 of the first one of the fasteners 613 to pass entirely through the outlet 659 (shown in FIG. 26) of the fastener housing 621. Deforming the lips 660 can be accomplished by pulling the fastener cartridge 610 away from the first one of the fasteners 613 (or by rocking the fastener cartridge 610 back and forth relative to the fastener 613 and pulling away from the fastener 613 after the fastener 613 is embedded in the object. This pulling and/or rocking action will cause the non-flexible tabs 658 of the fastener housing 621 to deform the lips 660 on the first one of the fasteners 613 to allow the fastener cartridge 610 to be separated from the first one of the fasteners 613. Such retention of the fastener 613 in the ready-to-be-driven position and such deliberate steps to separate the fastener 613 from the fastener cartridge 610 reduces or eliminates inadvertent separation of the fastener 613 from the fastener cartridge 610, thereby reducing or eliminating dropped and lost fasteners 613. In some configurations, the fasteners 613 may be made from a softer material than the fastener housing 621 to further facilitate deformation of the lips 660.

Figure 30A:
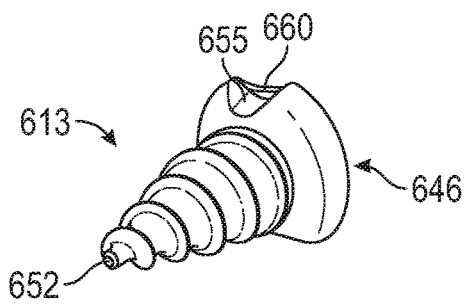
FIG. 30A is a perspective view of another fastener according to the principles of the present disclosure.
Figure 30B:
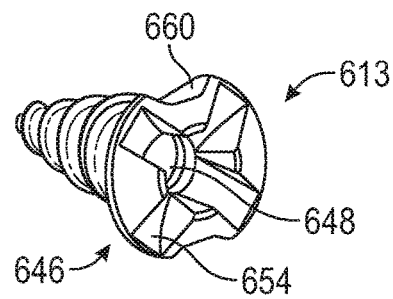
FIG. 30B is another perspective view of the fastener in FIG. 30A.

FIGS. 30A and 30B illustrate perspective views of the fasteners 613. The fasteners 613 include two recesses 655 and two lips 660. The number of non-flexible tabs 658 should equal at least the number of lips 660.

Figure 31:
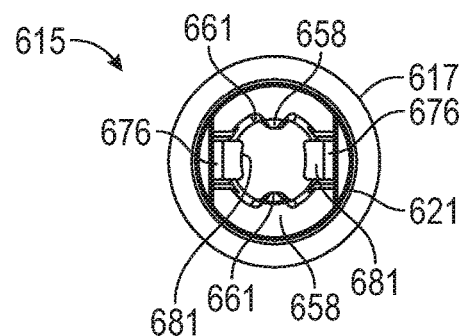
FIG. 31 is a head-on view of the body of the fastener cartridge of FIG. 25.

Referring to FIG. 31, FIG. 31 illustrates a head-on view of the body 615 including the plumber housing 617 and the fastener housing 621. As seen in FIG. 31, the fastener housing 621 includes two non-flexible tabs 658 that are diametrically opposed to one another. The two non-flexible tables 658 will align with the two recesses 655 and the projection 61 can align and interfere with the lips 660 of the fastener 613 (shown in FIGS. 30A and 30B). Further, the fastener housing 621 includes two flexible tabs 676 that include the projections 681 that extend radially inward form the distal ends of the flexible tabs 676. As discussed herein, when the flexible tabs 676 are in their nominal, at-rest positions, the radially innermost ends of the projections 481 of the flexible tabs 676 are disposed radially inward relative to a radially outermost periphery 649 of the head 646 of the fastener 613 in the ready-to-be-driven position, as shown in FIG. 29.

The plunger 622 may include a cylindrical shaft 653 extending along the longitudinal axis A5 from the flange 628 and is axially movable along the longitudinal axis A5 relative to the body 615 including the plumber housing 617 and the fastener housing 621. The shaft 653 may include a tip 651 that is shaped and sized to fit within the recess 648 of one of the fasteners 614 (as shown in FIGS. 31A and 31B). In one configuration, the plunger 622 can be formed of a material that deforms when subjected to autoclave temperatures. For example, an autoclave is a pressure chamber used to sterilize equipment by subjecting the equipment to high pressure and high temperature (e.g., 121° C.). To encourage one-time use of the fastener cartridge 610, if a user attempts to sterilize an already used fastener cartridge 610, the plumber can be formed of a material such as a plastic that will deform when under the temperatures for sterilization. The plumber 622 is configured to deform such that the functions of the plunger 622 are disabled and the fastener cartridge 610 cannot be used after sterilization.

As discussed herein, the fastener cartridge 610 can be coupled to the shaft 618 by inserting the shaft through the adaptor 619 such that the barbed tabs 631 engage with the annular recess on the shaft 618, as shown in FIG. 28. After the fastener 613 in the ready-to-be-driven position is driven in the object and as the fastener cartridge 610 is being separated from that fastener 613, the plunger 622, via the spring 624, pushes the next fastener 613 from the standby position to the ready-to-be-driven position, as described above. As the fastener 613 is being advanced from the standby position to the ready-to-be-driven position, the head 646 of the fastener 613 can force the tabs 676 to flex radially outward (away from the longitudinal axis A5) as the head 646 of the fastener 613 passes between the tabs 676 to the ready-to-be-driven position.

Figure 32A:
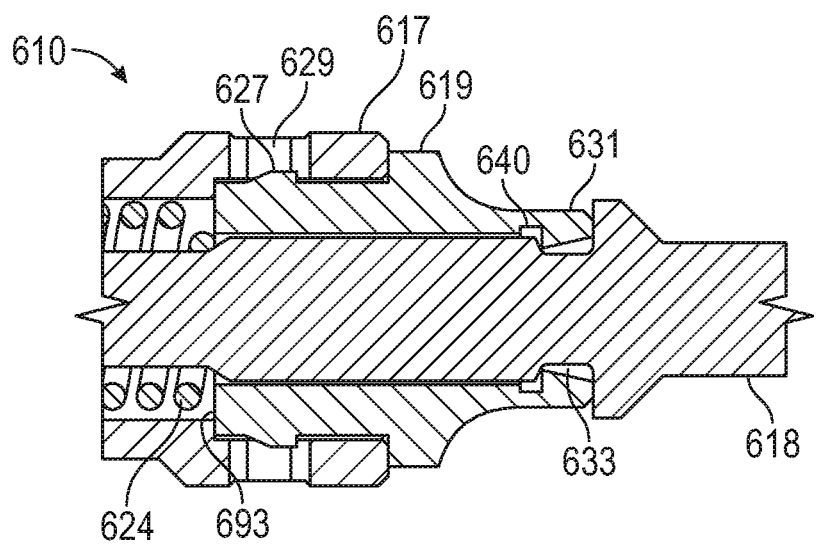
FIG. 32A is a close-up of the cross-sectional view of a portion of the fastener cartridge in FIG. 28.
Figure 32B:
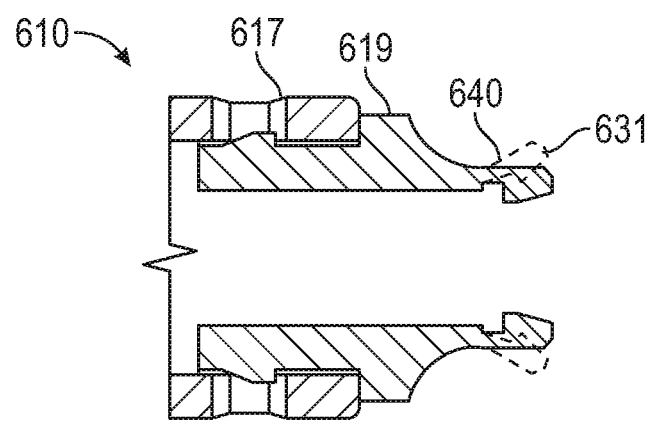
FIG. 32B is a close-up of the cross-sectional view of a portion of the fastener cartridge in FIG. 28.
Figure 33:
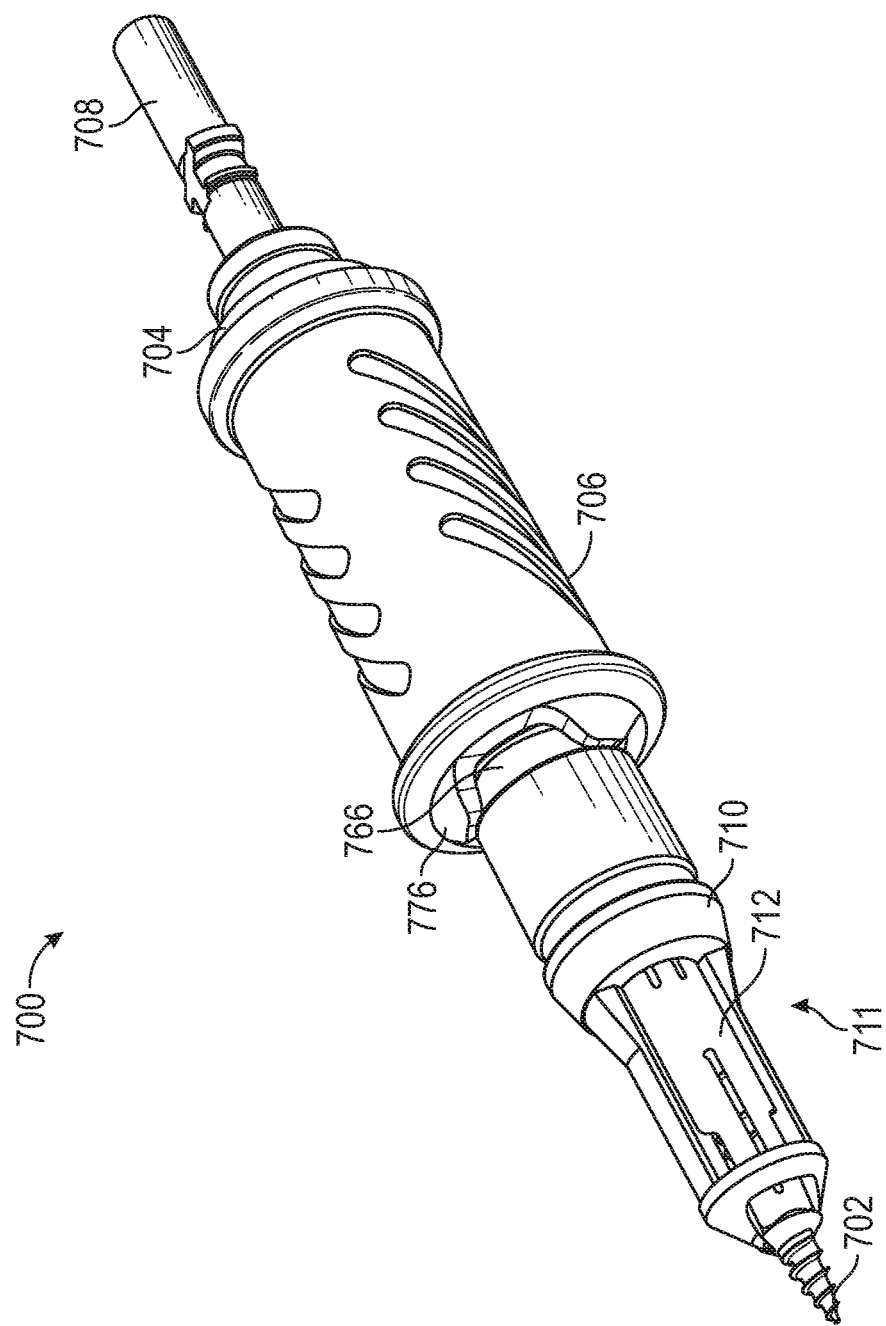
FIG. 33 is a perspective view of another fastener according to the principles of the present disclosure.
Figure 34:
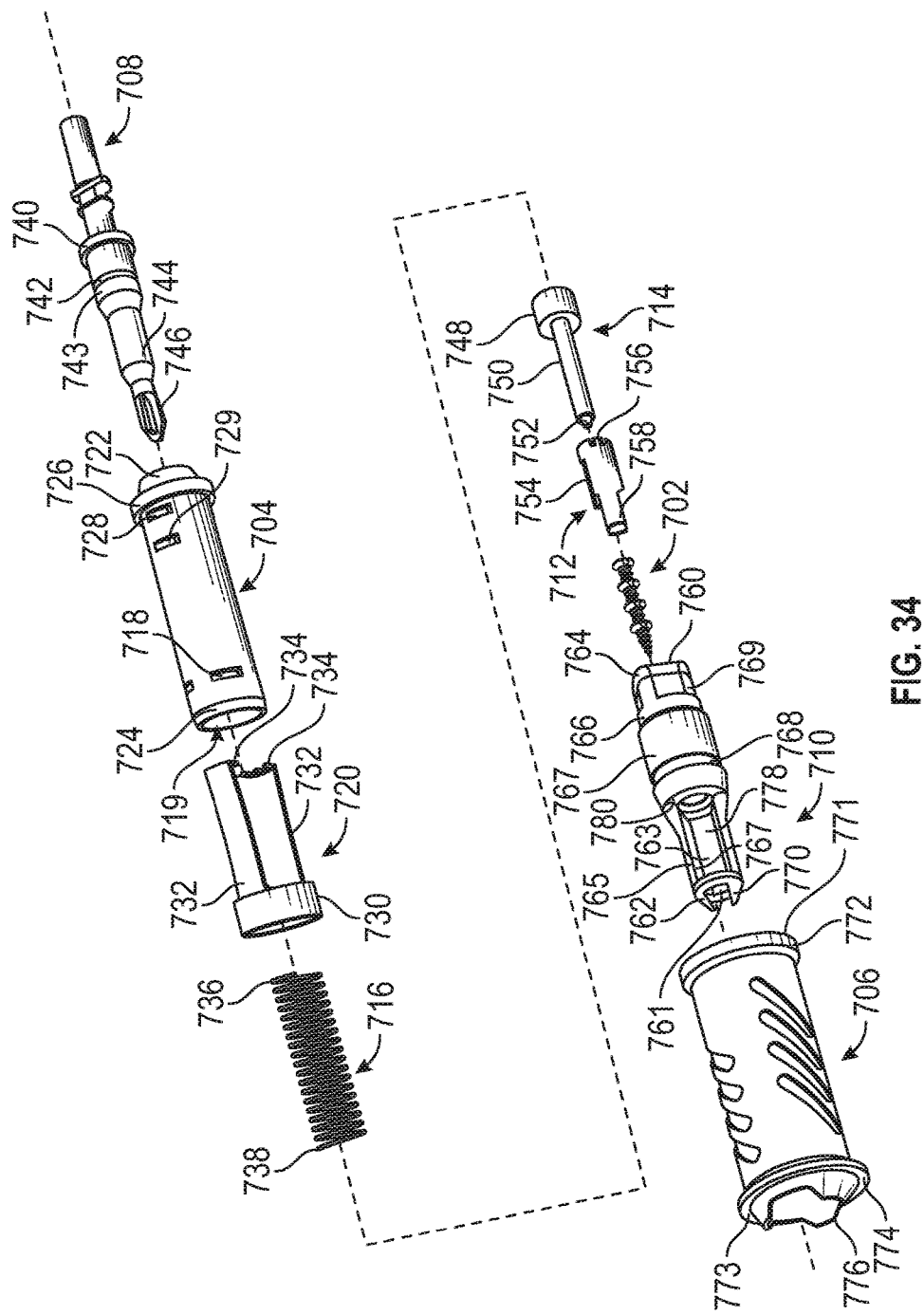
FIG. 34 is an exploded perspective view of the fastener cartridge.

After all of the fasteners 613 have been driven into the object (i.e., after all of the fasteners 613 have been separated from the fastener cartridge 610), the fastening cartridge 610 (including the body 615, plunger 622, spring 624, and adaptor 619) may be removed from the shaft 618. FIG. 32A illustrates a portion of the fastener cartridge 610 coupled to the shaft 618. As seen in FIG. 32A, the barbed tabs 631 are received within the annular recess 633 of the shaft 618. As discussed herein, the barbed tabs 631 can be formed such that once the shaft 618 is removed from the fastener cartridge 610, the barbed tabs 631 will no longer engage with the shaft 618. In one configuration, the barbed tabs 631 have a groove 640 along an inner surface to reduce the cross-sectional area of each barbed tab 631. Having the reduced cross-sectional allows deformation to occur when detaching from the shaft 618. For example, the force required to detach the fastener cartridge 610 from the shaft 618 makes the thinner cross-sectional area along the groove 640 exceed the yielding point of the material. Therefore, once the shaft 618 is removed, as seen in FIG. 32B, the barbed tabs 631 stay open and will not engage with the shaft 618 if a user tries to reconnect the fastener cartridge 610.

Attaching the shaft 618 to the fastening cartridge 610 requires a mounting force, which can be minimized to increase the ease of attachment for the user. A dismounting force (i.e., the force required to detach the shaft 618 from the fastener cartridge 610) can be greater than the disengagement force (i.e, the force required to disengage screws from the fastener cartridge 610) such that a user can separate the fastener cartridge 610 from a fastener 613 without disengaging the fastening cartridge 610 from the shaft 618. The spring force acting on the fasteners 613 via the spring 624 can be less than the disengagement force to prevent the fasteners 613 from ejecting before insertion into an object. Further, the spring force can be greater than the flexing force of the flexible tabs 676 such that the spring 624 can que up the next screw in line for insertion. Finally, the disengagement force can be less than the force required to pull a fastener 613 out of, for example, bone such that the fastener cartridge 610 can be disengaged from an inserted fastener 613 without removing the inserted fastener 613.

Once the fastener cartridge 610 is removed from the shaft 618, a driver tip 690 of the shaft 618 (which is shaped to be received in slots 654 of fasteners 613) can be used to engage drive fasteners one at a time. As discussed herein, the adaptor 619 can be formed such that once the fastening cartridge 610 is removed from the shaft 618, the barbed tabs 631 of the adaptor can exceed the yielding point of the material forming the adaptor 627 such that the barbed tabs 631 stay open and are not be able to engage with the shaft 618 more than once. Therefore, the fastening cartridge 610 can be a one-time use device.

Referring now to FIGS. 33-42, another fastener cartridge 700 is provided that may be used in conjunction with the driver 12 (FIG. 1) to hold and drive a predetermined number of fasteners 702 in a manner similar to the fastener cartridges 10, 110, 210, 310, 410, 510, and 610 described above. The structure and function of portions of the fastener cartridge 700 may be similar or identical to that of the fastener cartridge 110, 210, 310, 410, 510, and 610, apart from the exceptions described below and/or shown in the figures. Therefore, some similar features will not be described again in detail.

The fastener cartridge 700 may include a main housing 704, a drive clip 720, a spring 716, a plunger 714, a fastener housing 711 including a backstop component 712 and a fastener chamber 710, and a locking sleeve 706. The embodiment shown in FIGS. 33-42, provides a keyless, self-alignment and locking mechanism for attaching and detaching the fastener cartridge 700 to a shaft 708. For example, the shaft 708 can be a driver blade used to attach/detach to a driver 12 (FIG. 1). As discussed herein, the fastener cartridge 700 allows for the shaft 708 to be inserted into and couple with the fastener cartridge 700 without prior alignment. That is, during use, a user can insert the shaft 708 into the main housing 704 without regard to the positioning of the shaft 708 with respect to the main housing 704. Alignment is not needed because a round portion of the shaft 708 is inserted into a corresponding round hole in the main housing 704 and thus alignment of the shaft 708 relative to the main housing 704 is irrelevant and increasing the ease and use of the fastener cartridge 700. Subsequently, the locking sleeve 706 can be advanced over the drive clip 720 and main housing 704 to couple the fastener cartridge 700 to the shaft 708. As discussed herein, the fastener cartridge 700 can couple to the shaft 708 regardless of the positioning of the shaft 708 within the housing 704.

The shaft 708 can include a flange 740, a first body portion 743, a groove 742 formed in the first body portion 743, a second body portion 744, and a tip 746. The first and second body portions 743 and 744 can have a circular circumference such that the shaft 708 can be coupled to the fastener cartridge 700 without alignment. Further, the first body portion 743 can have a diameter larger than a diameter of the second body portion 744. As discussed herein, the groove 742 can be a square groove 742 that allows the fastener cartridge 700 to be axially and rotationally fixed when the fastener cartridge 700 is coupled to the shaft 708.

The main housing 704 includes an opening 719 extending from a first end 722 to a second end 724. The main housing 704 can include a flange 726, first apertures 728 (e.g., also referred to as locking apertures) and a spring retention opening 729 positioned toward the first end 722 and second apertures 718 positioned toward the second end 724. In an example, the main housing 704 can include two first apertures 728 and four second apertures 718. However, any number of first and second apertures 728 can be used. The fastening cartridge 700 can include a drive clip 720 that includes a base 730 and elongated legs 732 extending from the base 730. At the end of the elongated legs 732, the drive clip 720 can include projections 734 extending from the elongated legs 732. In an example, the projections 734 are substantially perpendicular to the elongated legs 732. Further, the projections 734 project from the elongated legs 732 such that a first projection and a second projection are diametrically opposed and extend towards each other. However, other configurations of the number, positioning, and spacing between the elongated legs 732 and corresponding projections 734 can be used.

The drive clip 720 is mounted onto the main housing 704 such that the main housing 704 extends through the base 730 and the projections 734 extend into the first apertures 728. In an unlocked configuration, the projections 734 extend partially into the first apertures 728 to maintain the position of the drive clip 720 along the housing, but do not extend into the opening 719 defined by the main housing 704. In the unlocked configuration, the shaft 708 can be inserted into the main housing 704 such that the first and second body portions 743, 744, which have a circular circumference can freely move axially and rotationally within with the circular opening 719 of the housing.

Once the shaft 708 is fully inserted into the fastening cartridge 700, which is when the flange 740 abuts the first end 722 of the main housing 704, the fastening cartridge 700 can be locked. When the shaft 708 is fully inserted into the fastening cartridge 700, the groove 742 on the shaft 708 is aligned with the first apertures 728 of the main housing 704. To lock the fastening cartridge 700 to the shaft 708, the locking sleeve 706 is moved up toward the first end 722 of the main housing 704 and over the driving clip 720. As the locking sleeve 706 moves along the driver clip 720 and the main housing 704, the locking sleeve 706 forces the elongated legs 732 to collapse against the main housing 702 thereby forcing the projections 734 further into the first apertures 728 such that a portion of the projections 734 extend through the first apertures 728, into the opening 719 of the main housing 704, and into the groove 742 of the shaft 742. When the projections 734 extend into the groove 742 on the shaft 708, the fastening cartridge 700 is axially and rotationally fixed onto the shaft 708.

Figure 37:
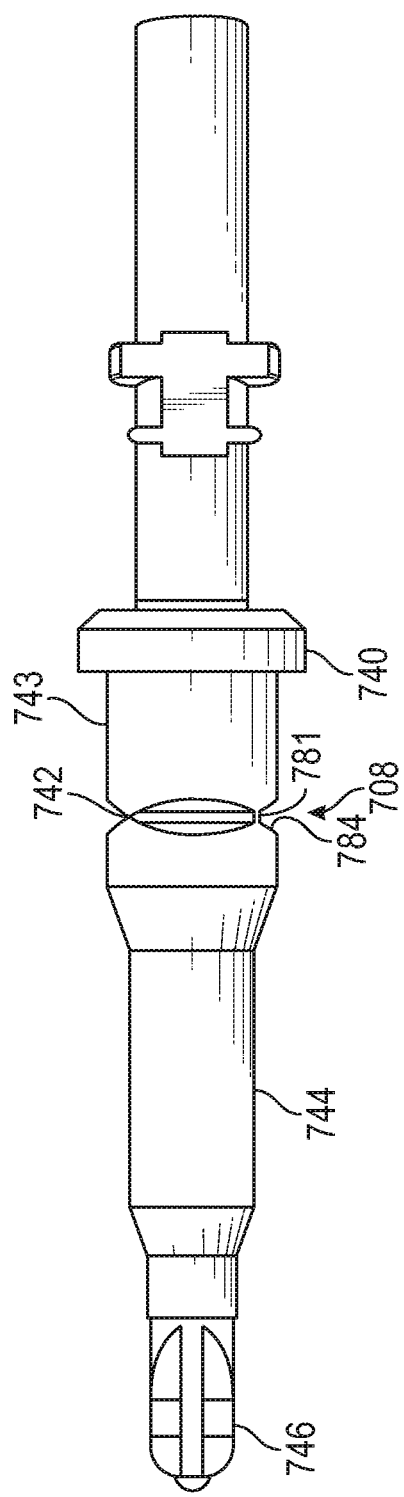
FIG. 37 is a side-view of a shaft configured to be coupled to the fastener cartridge.
Figure 38A:
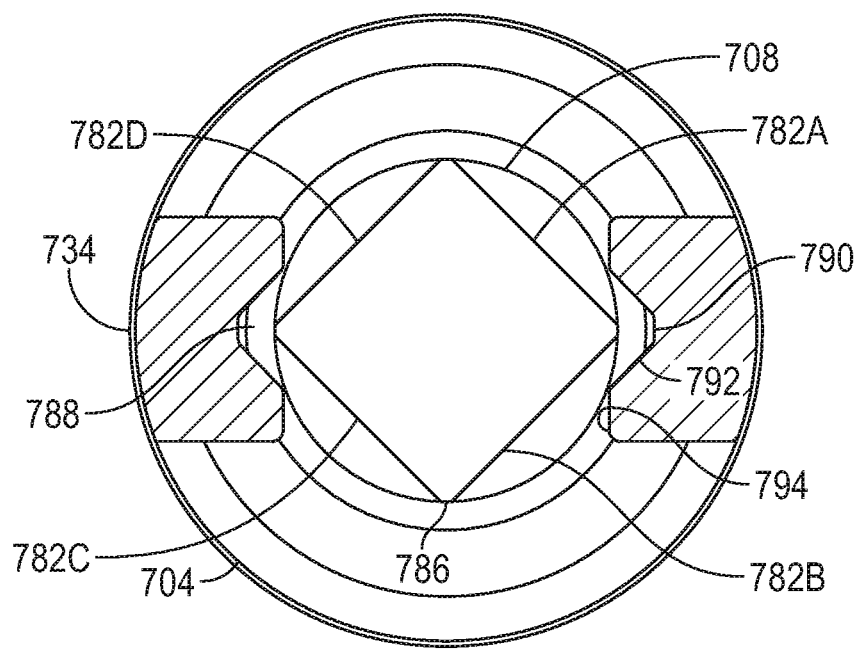
FIG. 38A is a cross-sectional view along a groove of the shaft when the fastener cartridge coupled to the shaft.
Figure 38B:
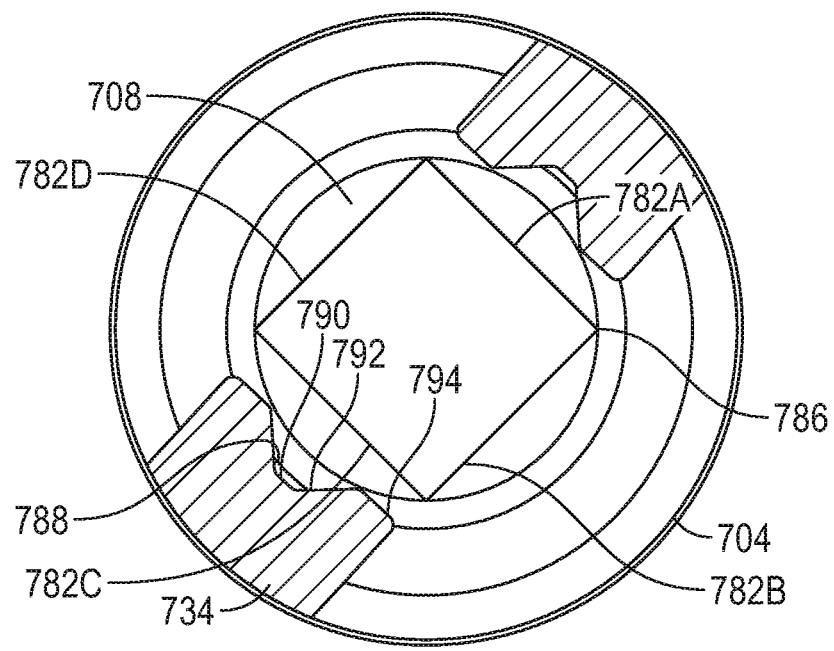
FIG. 38B is another cross-sectional view along a groove of the shaft when the fastener cartridge coupled to the shaft.

Referring to FIGS. 37-38, the groove 742 includes four separate grooves 782A-D to form a "square groove," as shown in FIGS. 38A and 38B, around the shaft 708. The groove 742 is formed into the circular cross-section of the first body portion 743 of the shaft 708. Each groove 782A-D includes a flat portion 781 and includes angled sides 784. Further, each groove 782A-D is distinct from each other. As illustrated, the groove 742 is cut such that each groove 782A-D is separated by a peak portion 786. The peak portion 786 can be non-cut portion that is a non-interrupted surface of the first body portion 743 of the shaft 708. In additional embodiments, the peak portion 786 can have a slightly reduced diameter compared to the diameter of the first body portion 743, but is substantial enough to separate each grove 782A-D.

As seen in FIGS. 38A-B, the projections 734 include a "V" shaped groove 788 including a valley portion 790 and an angled sides 792. Further, the projections 734 also include a ridge 794. The square groove 742 and the "V" shaped grove 788 in the projections 734 cooperate such that the position of the shaft 708 within the main housing 704 doesn't matter and no matter the position, the projections 734 are able to engage with the groove 742 while being axially and rotationally secure. For example, in one alignment of the shaft 708 relative to the main housing 704, the "V" shaped groove 788 of the projections 734 straddles the peak portion 786 of the shaft 708 and each ridge 794 portion of the projection 734 can extend into one of the grooves 782A-D, as shown in FIG. 38A. In another alignment of the shaft 708 relative to the main housing 704, the projection 734 is aligned with one of the grooves 782A-D, such that an entire projection 734 extends into one of the grooves 782A-D of the groove 742. In an example, the width of a projection 734 equals the width of one of the grooves 782A-D. In other alignments, a portion of the angled sides 794 of the "V" shaped groove 788 or the ridges 794 can engage with the peak portion 786 of the shaft 708. The shape of the projections 734 is such that regardless of where the peak portion 786 hits the projection 734, the main housing 704 and drive clip 720 can self-align to one of the configurations shown in FIGS. 38A and 38B. For example, if the alignment of the shaft 708 and the projections 734 is in-between one of the illustrated alignments the interaction between surfaces of the peak portion 784 and the "V" shaped groove 788 and ridges 794 will self-align the projections 734 to one of the configurations shown in FIGS. 38A and 38B.

Figure 35:
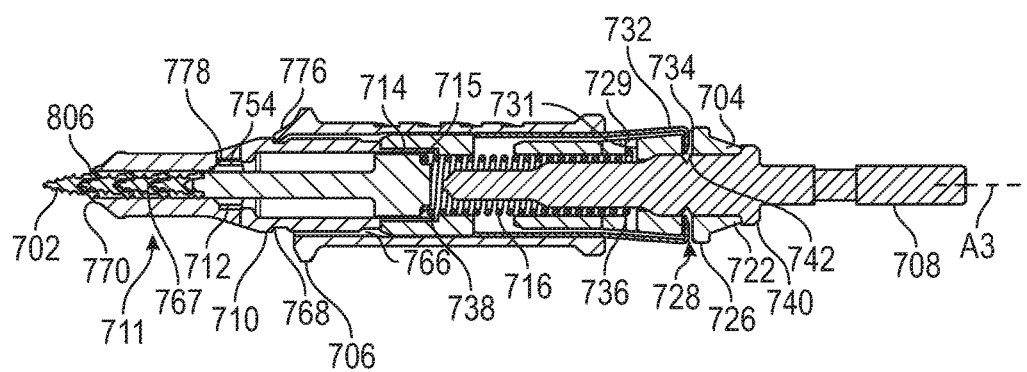
FIG. 35 is a cross-sectional view of the fastener cartridge showing the non-flexible tabs engaged with a fastener.
Figure 36:
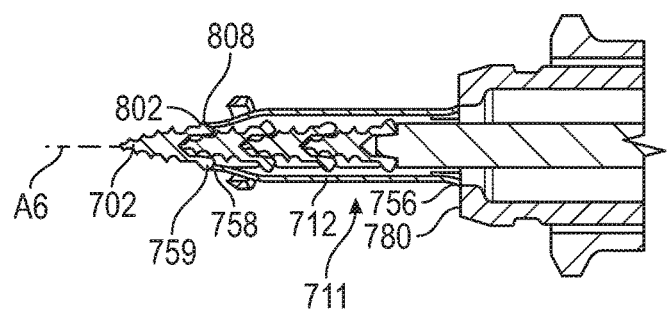
FIG. 36 is a partial cross-sectional view of the fastener cartridge showing the resilient flexible tabs engaged with the fastener.

The fastener cartridge 700 includes the spring 716 and the plunger 714. The spring 716 is movably disposed within the main housing 704 and extends from a first end 736 to a second end 738. The plunger 714 include a shaft 750 extending along the longitudinal axis A6 from a flange 748 and is axially movable along the longitudinal axis A6 relative to the main housing 704, the locking sleeve 706, and the fastener housing 711. The tip 752 is shaped to engage one or more of the recess 800 (FIG. 39A) of the fasteners 702. In an example, the first end 736 of the spring 716 is positioned within the spring retention opening 729. In another example, the first end 736 can be positioned against a backstop 731 within the main housing 731. Further, the first end 736 can be positioned within the spring retention opening 729 and abut the backstop 731. The second end 738 of the spring 716 is positioned around a projection 715 extending from the flange 748 of the plunger 714 and can bias the plunger 714 away from the shaft 708 along a longitudinal axis A6 of the fastener cartridge 700. As seen in FIG. 35, the spring 716 receives a portion of the shaft 708. As discussed herein, the shaft 708 can move axially and rotationally within the spring 716 until the fastener cartridge 700 is in the locked configuration.

The fastener housing 711 can include the fastener chamber 710 and the backstop component 712. The fastener chamber 710 can be attached to and extend from the second end 724 of the main housing 704. The fastener chamber 710 can extend from a first end 760 to a second end 762. The fastener chamber 710 can include a main body 767 and a chamber portion 765 that defines a chamber 763. The main body 767 can have a groove 768 and a ledge 766, the ledge 766 being positioned closer to the first end 760 as compared to the groove 768. In an example, the main body 767 includes a keyed surface 769 that extends from the first end 760 toward the ledge 766. The keyed surface 769 includes projections 764 that may engage the main housing 704 by a snap fit (e.g., projections 764 of the fastener chamber 710 snap into the second apertures 718 of the main housing 704).

The fastener chamber 710 may be shaped to rotationally key the fasteners 702 relative to the fastener housing 711. The fastener chamber 710 may include a pair of protrusions 770 that extend into the chamber 763 to engage recesses 806 (shown in FIGS. 39A-B and 40) of the fasteners 702 to prevent relative rotation between the fasteners 702 and the fastener housing 711 while allowing the fasteners 702 to move axially relative to the fastener chamber 710.

The first end 762 of the fastener chamber 710 may include a plurality of non-flexible tabs 770 that extend radially into the chamber 763 at an outlet 761 of the chamber 763. Each of the non-flexible tabs 770 may be received in a corresponding one of the recesses 806 in the fastener 702 that is in the ready-to-be-driven position (i.e., the fastener 702 that is extending out of the fastener chamber 710 and whose tip 807 is pointed away from the fastener cartridge 700). Interference between the non-flexible tabs 770 and the recesses 806 of the ready-to-be-driven fastener 702 prevents inadvertent disengagement between the fastener cartridge 700 and the ready-to-be-driven fastener 702.

The chamber portion 765 of the fastener chamber 710 includes ridges 767 extending along the chamber 765. The ridges 767 are configured to be positioned within the recesses 804 of the heads 802 of the fasteners 702 to prevent rotation of the fasteners 702 within the fastener chamber 710. The ridges 767 define a first ledge 778 and the main body 767 defines a second ledge 780. The first and second ledges 778, 767 can interact with the backstop component 712 to maintain the position of the backstop component 712 within the fastener chamber 710, as discussed herein.

Figure 39A:
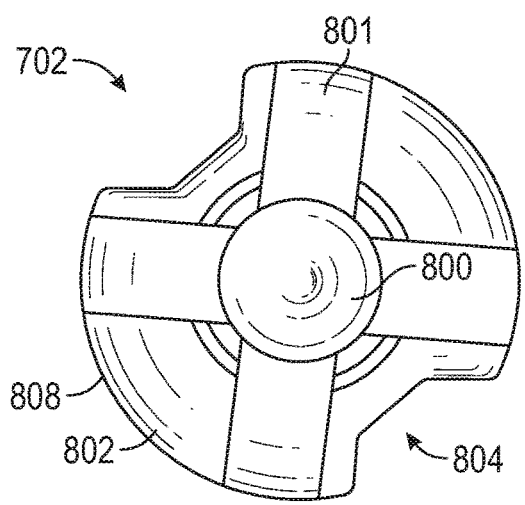
FIG. 39A is a top-down view of a fastener.
Figure 39B:
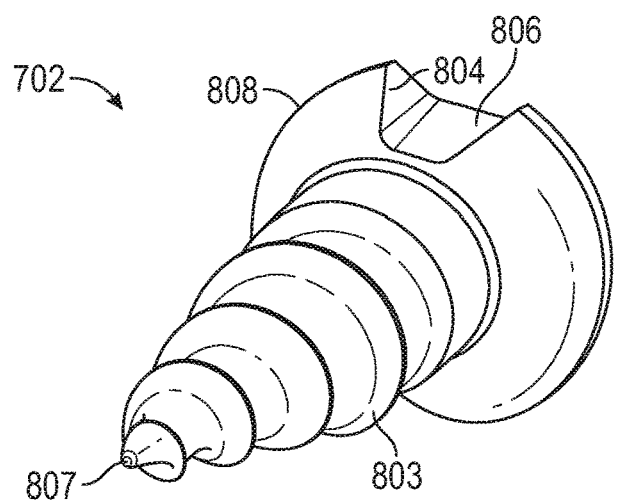
FIG. 39B is a perspective view of the fastener.
Figure 40:
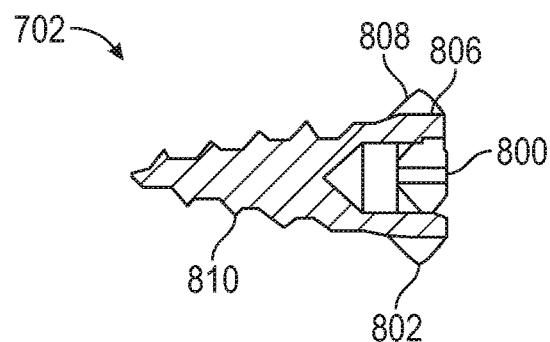
FIG. 40 is a cross-sectional view of the fastener.
Figure 41:
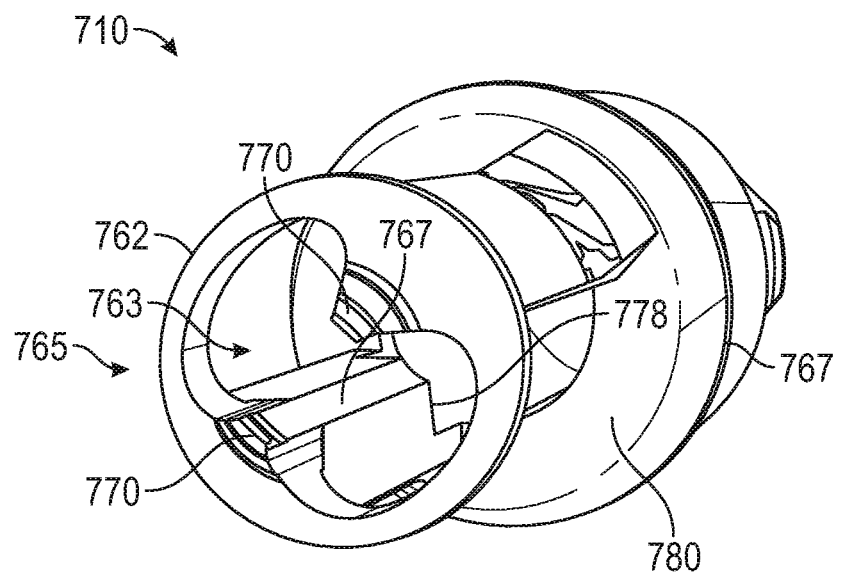
FIG. 41 is a perspective view of a fastener chamber.
Figure 42:
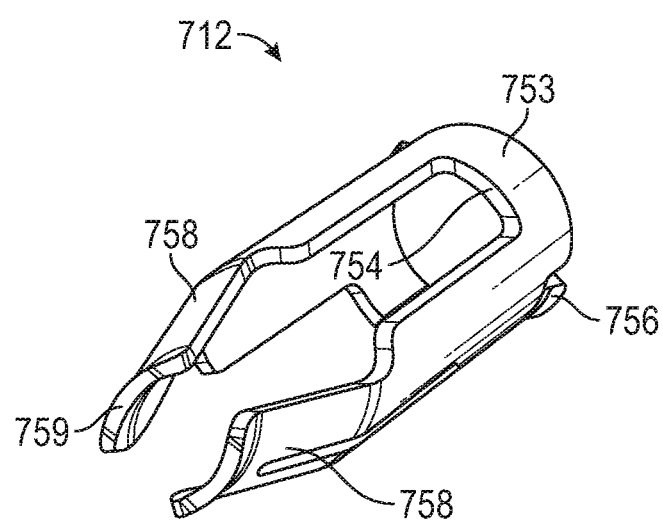
FIG. 42 is a perspective view of a backstop component.
Figure 43:
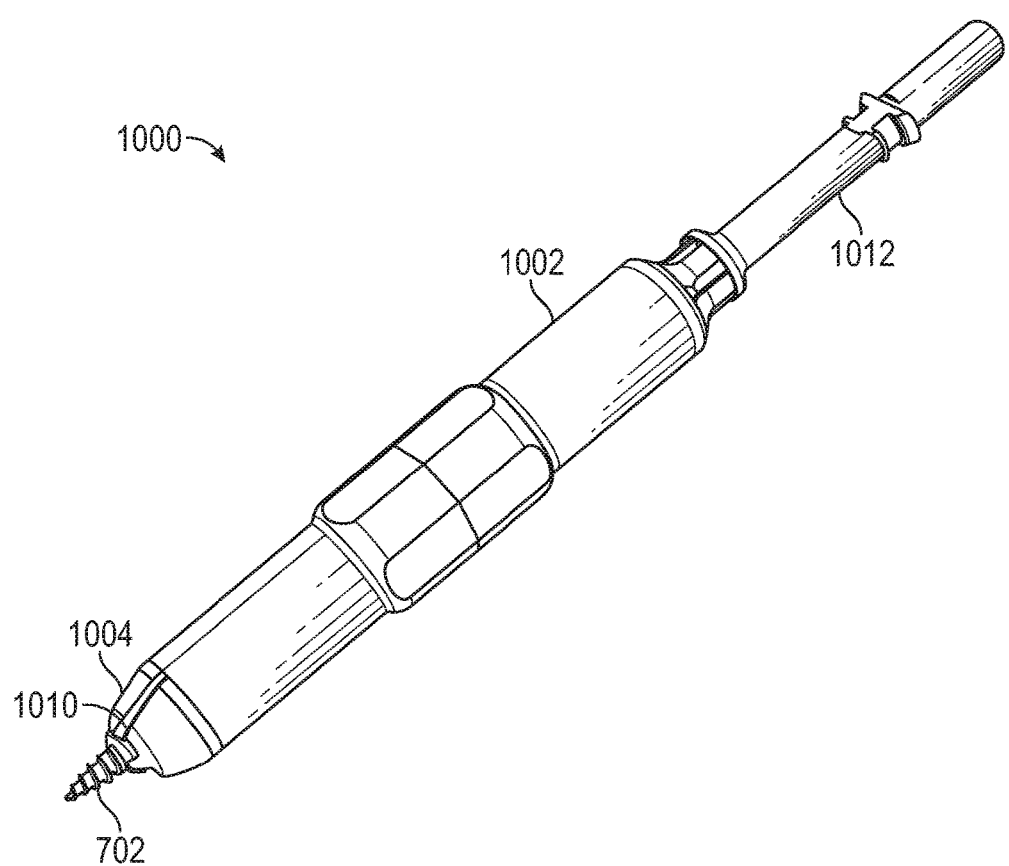
FIG. 43 is a perspective view of another fastener according to the principles of the present disclosure.

As shown in FIGS. 39A-B and 40, the fasteners 702 include recesses 804, which are defined partially by a ramped surface 806. The ramped surface 806 of the recess 804 is such that it prevents inadvertent disengagement between the fastener cartridge 700 and the ready-to-be-driven fastener 702. While the recesses 804 are shown as having a ramped surface 806, the recesses 804 can also be formed as lips that partially define the recess as shown herein for fastener 14 (see FIG. 7). Between each recess 804 the head 802 can include lobes 808 that form a generally cross-shaped periphery of the head 802. It will be appreciated that the fastener chamber 710 and heads 802 could be alternatively shaped to rotationally key the heads 802 of the fasteners 702 to the fastener housing 711.

Each fastener 702 includes a socket 800 that extends along the longitudinal axis of the fastener 702 into the head 802. A threaded shaft 803 of each fastener 702 may have a tapered tip 807 that can be received in the socket 800 of an adjacent fastener 702 so that the fasteners 702 can be nested within each other. The heads 802 of the fasteners 702 may also include one or more slots 801 that can be configured to receive a Phillips-head (cross-shaped) or flat-head driver tip, for example.

The backstop component 712 may be a generally tubular member having a base 753 and a plurality of resiliently flexible tabs 758 extending from the base 753. The base 753 can include an edge 754 and flared tabs 756. The backstop component 712 can be received within the fastener chamber 710 and is axially and rotationally fixed within the fastener chamber 710. For example, during insertion, the backstop component 712 can be inserted into the fastener chamber 710 until the edge 754 abuts the first ledge 778 formed by the ridges 767 of the fastener chamber 710. Further, the flared tabs 756 can collapse during insertion and subsequently expand once they clear the main body 767 of the fastener chamber 710 and abut the second ledge 780 of the fastener chamber 710, thereby preventing movement of the backstop component 712 within the fastener chamber 710.

As discussed herein, the resiliently flexible tabs 758 prevent the fastener 702 in the ready-to-be-driven position from being pushed back into a fastener chamber 710. Because the flexible tabs 758 prevent the fastener 702 in the ready-to-be-driven position from being pushed back into the fastener chamber 710, the fasteners 702 in the standby positions and the plunger 714 are prevented from being pushed toward the shaft 708 of the fastener cartridge 700.

The flexible tabs 758 extend from the base 753 in an axial direction (along a longitudinal axis A3 of the fastener housing 711) toward an outlet 761 of the fastener chamber 710 and radially inward toward the longitudinal axis A3. The flexible tabs 758 are in their nominal, at-rest positions when one of the fasteners 702 is in the ready-to-be-driven position, as shown FIG. 36. When the flexible tabs 758 are in their nominal, at-rest positions, the free ends 759 of the flexible tabs 758 are disposed radially inward relative to a radially outermost periphery of lobes 808 of the head 802 of the fastener 702 in the ready-to-be-driven position. Therefore, interference between the free ends 759 of the flexible tabs 758 and the head 802 of the fastener 702 in the ready-to-be-driven position prevents the fastener 702 in the ready-to-be-driven position from being pushed back into the fastener chamber 710. While the fastener chamber 710 and the backstop component 712 are illustrated as being separate components, it is contemplated that they can be formed integral with one another.

The fastener cartridge 700 also includes the locking sleeve 706. As discussed herein, the locking sleeve 706 can have two positions, an unlocked position and a locked position. In the unlocked position, the shaft 708 is free to move axially and rotationally within the main housing 704. Once the locking sleeve 706 is at the locked position, the shaft 708 is axially and rotationally fixed within the main housing 704 and the fastener housing 711. The locking sleeve 706 extends from a first end 771 to a second end 773. The first end 771 includes a first flange 772 and the second end 773 includes a second flange 774 with projections 776 extending from the second flange 774. As seen in FIG. 35, the locking sleeve 706 is in the unlocked position. At the unlocked position, the projections 776 extend into the groove 768 of the fastener chamber 710 to maintain the position of the locking sleeve 706 along the main housing 704. Further, at the unlocked position, the projections 734 extend partially into the first aperture 728 of the main housing 704 but do not extend into the opening 719 defined by the main housing 704 thereby allowing the shaft 708 to move freely within the main housing 704. To move the locking sleeve 706 from the locked position, a user pushes the locking sleeve 706 toward the first end 722 of the main housing 704, which will disengage the projections 776 from the groove 768 such that the locking sleeve 706 can move along the main housing 704. As discussed herein, as the locking sleeve 706 moves toward the first end 722 of the main housing 704, the elongated legs 732 of the drive clip 720 collapse against the main housing 704 such that the projections 734 extend through the first apertures 726 and into the groove 742 on the shaft 708 thereby axially and rotationally fixing the shaft 708 to the main housing 704.

After the first one of the fasteners 702 has been driven into the object to a desired depth, the user may disengage the fastener cartridge 700 from the first one of the fasteners 702 by applying a force (or forces) to slightly deform the ramped surface 806 of the first one of the fasteners 702 to allow the head 802 of the first one of the fasteners 702 to pass entirely through the outlet 761 of the fastener chamber 710. Deforming the ramped surface 806 can be accomplished by pulling the fastener cartridge 700 away from the first one of the fasteners 702 (or by rocking the fastener cartridge 700 back and forth relative to the fastener 702 and pulling away from the fastener 702) after the fastener 702 is embedded in the object. This pulling and/or rocking action will case the non-flexible tabs 770 of the fastener chamber 710 to deform the ramped surface 806 on the first one of the fasteners 702 to allow the fastener cartridge 700 to be separated from the first one of the fasteners 702. Such retention of the fastener 702 in the ready-to-be-driven position and such deliberate steps to separate the fastener 702 from the fastener cartridge 700 reduces or eliminates inadvertent separation of the fastener 702 from the fastener cartridge 700, thereby reducing or eliminating dropped and lost fasteners 14.

After the fastener 702 in the ready-to-be-driven position is driven in the object and as the fastener cartridge 700 is being separated from that fastener 702, the plunger 7014 pushes the next fastener 702 from the standby position to the ready-to-be-driven position, as described above. As the fastener 702 is being advanced from the standby position to the ready-to-be-driven position, the head 802 of the fastener 702 can force the flexible tabs 758 to flex radially outward (away from the longitudinal axis A3) as the head 802 of the fastener 802 passes between the flexible tabs 758 to the ready-to-be-driven position.

In some configurations, after all of the fasteners 702 have been driven into the object (i.e., after all of the fasteners 702 have been separated from the fastener cartridge 700), the fastener cartridge 700 may be removed from the main housing 704. Thereafter, another fastener cartridge 700 may be reattached to the housing 316.

Referring now to FIGS. 43-49, another fastener cartridge 1000 is provided that may be used in conjunction with the driver 12 to hold and drive a predetermined number of fasteners into an object, in a manner similar to the fastener cartridges described above. The structure and function of the fastener cartridge 1000 may be similar or identical to that of the fastener cartridges 110, 210, 310, 410, 510, 610, and 700 described above, apart from the exceptions described below and/or shown in the figures. Therefore, some similar features will not be described again in detail.

The fastener cartridge 1000 may include a main housing 1002, a fastener housing 1004, a plunger 1006, a spring 1008 and a backstop component 1010. The fastener cartridge 1000 can be coupled to a shaft 1012 that engage with a tool, as described herein. The housing 1004 and the shaft 1012 are separate components that are attachable to each other. The housing 1004 includes a first end 1014 that receives and removably engages with the shaft 418. The first end 1014 may include a plurality of flexible, barbed tabs 1016 that snap into an annular recess 1018 in the shaft 1012. The housing 1002 can define an opening 1020 that extends from the first end 1014 to a second end 1022 of the housing 1002. A portion 1026 of the housing 1002 defining the opening 1020 is configured to mate with a mating portion 1024 of the shaft 1012. The portion 1026 has a shape that corresponds to the shape of the mating portion 1024. For example, the portion 1026 defining the opening and the mating portion 1024 include one or more flat surfaces that mate with each other to prevent relative rotation between the shaft 1024 and the housing 1002. The engagement between the housing 1002 and the shaft 1012 is strong enough to keep the shaft 1012 and housing 1002 fixed to each other during operation of the drill with the fastener cartridge 100

The spring 1008 and the plunger 422 are movably disposed within the housing 1002. In the embodiment shown, the spring 1008 is an expansion spring. A first end 1027 of the spring 1028 includes a loop 1028 that can hook onto the plunger 1006. For example, the plunger 1006 includes a recess 1030 at a first end 1032 of the plunger 1006. Other configurations for coupling a first end of a spring to the plunger are possible. A second end 1030 of the spring 1008 abuts a first end 1038 of the fastener housing 1004. When disposed with the housing 1002, the second end 1030 of the spring 1008 abuts a projection 1042 extending into the opening 1020 of the housing 1002. In an example, the second end 1030 of the spring 1006 has a larger diameter compared to the remaining portion of the spring 1006. Thus, when the spring 1006 is inserted into the housing 1002 via the second end 1022, the spring 1006 will extend into the housing 1002 until the second end 1030 abuts the projection 1042. When assembled, the spring 1008 should be in expansion such that as fasteners 702 driven from the fastener cartridge 100, the spring 1008 contracts thereby biasing the plunger 1006 plunger 422 away from the shaft 1012 along a longitudinal axis A6 of the fastener cartridge 1000.

The fastener housing 1004 can extend from a first end 1038 to a second end 1040. The fastener housing 1004 may be attached to and extend from the first end 1022 of the housing 1002. In some configurations, the fastener housing 1002 may include a key portion 1044 (having one or more flat surfaces) that is received in a keyway 1046 (having one or more flat surfaces) of the housing 1002 to prevent relative rotation between the housing 1002 and the fastener housing 1004. The fastener housing 1004 may include a fastener chamber 1048 extending axially therethrough. The fastener chamber 1048 may be shaped to rotationally key the fasteners 702 relative to the fastener housing 1004. That is, the fastener chamber 1048 is shaped so that fasteners 702 are rotationally fixed to the fastener housing 1004 while allowing the fasteners 702 to move axially (along axis A5) relative to the fastener housing 1004.

Figure 44:
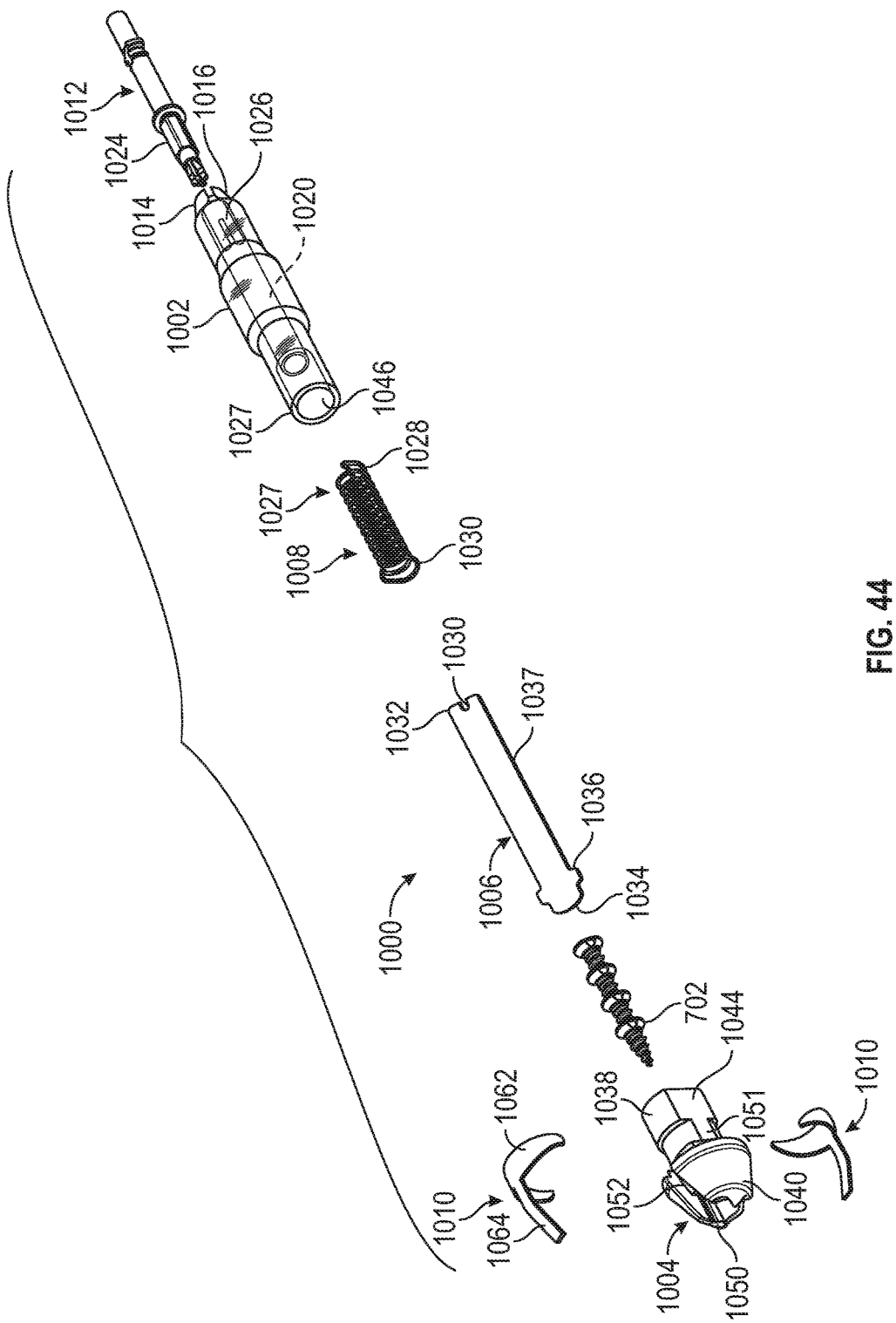
FIG. 44 is an exploded perspective view of the fastener cartridge.
Figure 46:
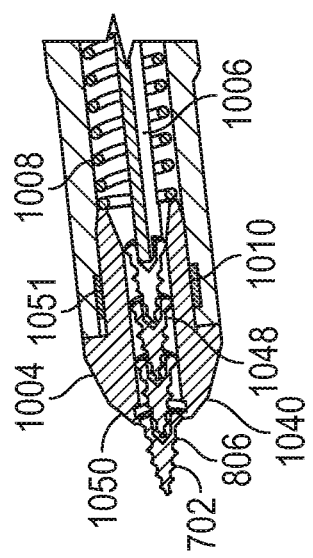
FIG. 46 is a partial cross-sectional view of the fastener cartridge showing the non-flexible tabs engaged with a fastener.
Figure 49:
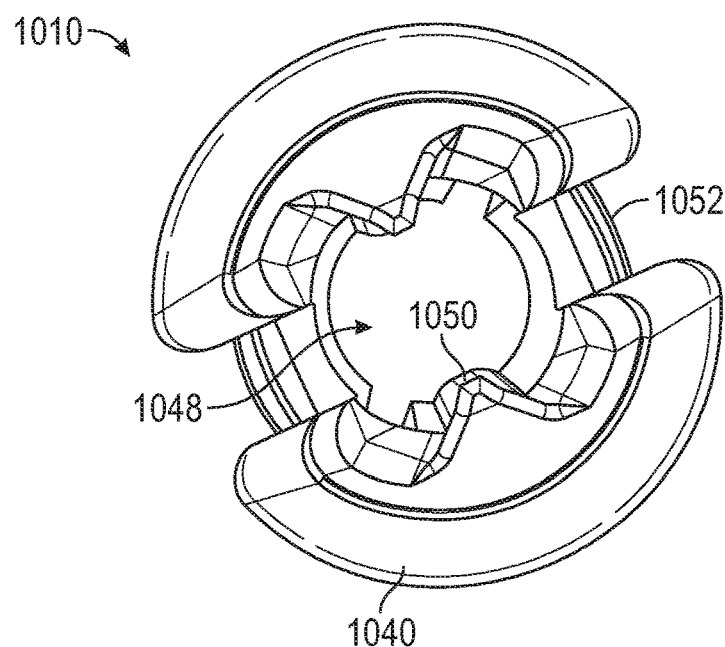
FIG. 49 is a view of the fastener housing form the second end of the fastener housing.

As shown in FIGS. 44, 46, and 49, the second end 1040 of the fastener housing 1004 may include a plurality of non-flexible tabs 1050 that extend radially into the fastener chamber 1048 at an outlet of the fastener housing 1004. A slot 1052 may be disposed between each pair of adjacent non-flexible tabs 1050. Each of the non-flexible tabs 1050 may be received in a corresponding one of the recesses 800 in the fastener 702 that is in the ready-to-be-driven position (i.e., the fastener 702 that is extending out of the fastener housing 1004 and whose tip 807 is pointed away from the fastener cartridge 100). Interference between the non-flexible tabs 1050 and the ramped surface 806 of the ready-to-be-driven fastener 702 prevents inadvertent disengagement between the fastener cartridge 1000 and the ready-to-be-driven fastener 702. While shown with fasteners 702, the fastener cartridge 100 can be used with fasteners 14, described herein.

Figure 45:
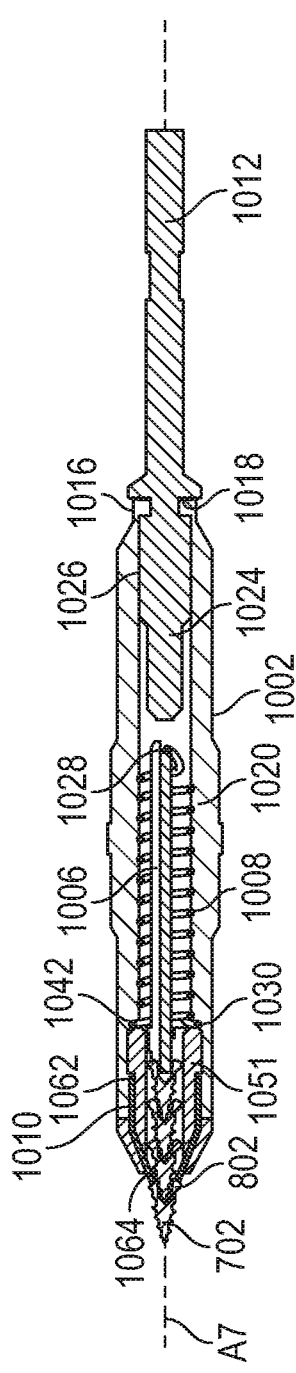
FIG. 45 is a cross-sectional view of the fastener cartridge coupled to a shaft showing the resilient flexible tabs engaged with a fastener.
Figure 48:
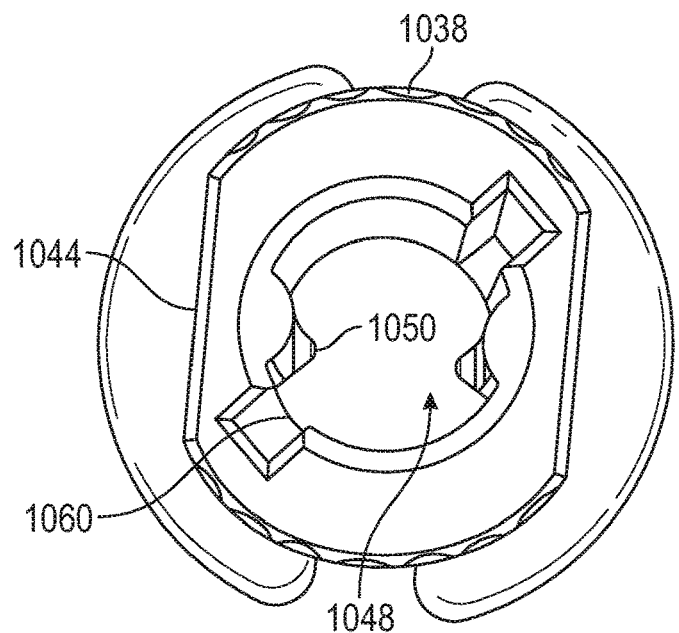
FIG. 48 is a view of the fastener housing from the first end of the fastener housing.

The plunger 1006 may include a shaft 1037 extending from the first end 1032 to a second end 1034. As discussed herein, the first end 1032 can include a recess that can engage with the first end 1027 of the spring 1008. The second end 1034 of the plunger 1006 is sized and shaped to fit within the slot 801 of one of the fasteners 702 (as shown in FIGS. 45 and 46.) Further, the plunger 1006 includes projections 1036 positioned toward the second end 1034. As seen in FIG. 48, the fastener housing 1004 includes a slot 1060. The slot is sized and shaped to receive the projections 1036 of the plunger to rotationally fix the plunger 1006 relative to the fastener housing 1004.

Figure 47:
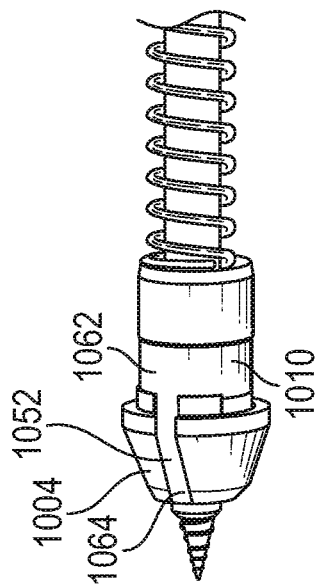
FIG. 47 is a side-view of a portion of the fastener cartridge showing the interaction between the backstop component and the fastener housing.

The fastener cartridge 1000 includes the backstop component 1010 that is configured to interact with the fastener housing 1004. The backstop component 1010 includes two backstop components 1010 each including a mating portion 1062 and a resilient flexible tab 1064. The mating portions 1062 are configured to mate with a backstop mating section 1051 of the fastener housing 1004. As seen in FIG. 47, the mating portions 1062 wrap around the backstop mating section 1051 such that the resilient flexible tab 1064 of each backstop component 1010 extends along a corresponding slot 1052 of the fastener housing 1004.

When the backstop component 1010 is coupled to the fastener housing 1004, the flexible tabs 1064 prevent the fastener 702 in the ready-to-be-driven position from being pushed back into the fastener chamber 1048. Because the flexible tabs 476 prevent the fastener 14 in the ready-to-be-driven position from being pushed back into the fastener chamber 1048, the fasteners 702 in the standby positions and the plunger 1006 are prevented from being pushed toward the shaft 1012 of the fastener cartridge 1000.

The flexible tabs 1064 are in their nominal, at-rest positions when one of the fasteners 702 is in the ready-to-be-driven position, as shown in FIGS. 45 and 47. When the flexible tabs 1064 are in their nominal, at-rest positions, the radially innermost ends of the flexible tabs 1064 are disposed radially inward relative to a radially outermost periphery of the head 802 of the fastener 702 in the ready-to-be-driven position. Therefore, interference between the resiliently flexible tabs 1064 and the head 802 of the fastener 702 in the ready-to-be-driven position prevents the fastener 702 in the ready-to-be-driven position from being pushed back into the fastener chamber 1042.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A fastener cartridge, comprising:
    a main housing extending from a first end to a second end, the main housing defining an opening extending from the first end to the second end and a locking aperture extending from an external surface to the opening;
    a drive clip positioned around the main housing, the drive clip including a base, an elongated leg extending from the base, and a projection extending from the elongated leg;
    a fastener housing including a fastener chamber including a plurality of non-flexible tabs and a backstop component including a plurality of resiliently flexible tabs, wherein the fastener housing is configured to include a plurality of fasteners that are arranged therein such that the longitudinal axes of the fastener chamber and the plurality of fasteners are collinear; and
    a locking sleeve configured to move along the main housing and couple the fastener cartridge to a shaft of a tool.

2. The fastener cartridge of claim 1, wherein the locking sleeve is configured to move between a first position, corresponding to an unlocked position, and a second position, corresponding to a locked position.

3. The fastener cartridge of claim 2, wherein, in the first position, the locking sleeve is engaged with the fastener chamber at a first location along the fastener chamber and the projection of the drive clip is positioned within the locking aperture but not within the opening defined by the main housing.

4. The fastener cartridge of claim 1, wherein, transitioning from the first position to the second position, the locking sleeve is disengaged from the fastener chamber and moved along the main housing toward the first end of the main housing until the locking sleeve is engaged with the fastener chamber at a second location along the fastener chamber, the second location closer to the first end of the main housing as compared to the first location.

5. The fastener cartridge of claim 4, wherein, at the second position, the elongated leg collapses against the main body forcing the projection of the drive clip to extend through the locking aperture and into the opening defined by the main housing.

6. The fastener cartridge of claim 1, further including:
    a plunger disposed within and axially movable within the main housing and the fastener housing; and
    a spring biasing the plunger in a first direction into contact with one of the fasteners and urging the plunger toward an outlet of the fastener chamber at a distal end of the fastener chamber farthest from the spring.

7. The fastener cartridge of claim 6, wherein the plurality of resiliently flexible tabs allow the plunger and fasteners to move axially in the first direction and restrict movement of the fasteners in a second direction opposite the first direction.

8. The fastener cartridge of claim 7, wherein a portion of the fastener chamber is shaped to prevent relative rotation between the fasteners and the fastener chamber and to allow the fasteners to move therein along the longitudinal axes in response to axial movement of the plunger relative to the body.

9. The fastener cartridge of claim 6, wherein the plurality of resiliently flexible tabs are configured to transition from a first at-rest position to a second flexed position by flexing outward away from the longitudinal axes to allow the fasteners to move axially in the first direction.

10. The fastener cartridge of claim 9, wherein, at the first at-rest position, the resiliently flexible tabs are configured to interfere with a head of one of the fasteners to restrict movement of the fasteners in the second direction.

11. A system, comprising:
    a fastener cartridge, including:
        a main housing defining an opening that extends from a first end of the main body to a second end of the main housing;
        a drive clip positioned around the main housing, the drive clip including a projection configured to engage with a shaft of a tool;
        a fastener housing, including:
            a fastener chamber including a plurality of non-flexible tabs; and
            a backstop component including a plurality of resiliently flexible tabs, wherein the fastener housing is configured to include a plurality of fasteners that are arranged therein such that the longitudinal axes of the fastener chamber and the plurality of fasteners are collinear; and
        a locking sleeve configured move along the main housing between a first position, corresponding to an unlocked position, and a second position, corresponding to a locked position, wherein, at the locked position, the projection engages with the shaft to couple the fastener cartridge to the tool.

12. The system of claim 11, wherein the fastener cartridge further includes:
    a plunger disposed within axially movably within the main housing and the fastener housing;
    a spring biasing the plunger in a first direction into contact with one of the fasteners and urging the plunger toward an outlet of the fastener chamber at a distal end of the fastener chamber farthest from the spring.

13. The system of claim 11, wherein each of the plurality of fasteners includes:
    a threaded shaft; and
    a head disposed at an end of the threaded shaft and including a plurality of lobes and a plurality of recesses each disposed between adjacent lobes and each partially defined by one of a deformable lip extending radially outward and a ramped surface.

14. The system of claim 11, wherein the plurality of non-flexible tabs are each configured to engage one of the deformable lip and ramped surface of one of the fasteners to prevent the one of the fasteners from inadvertently passing entirely out of the outlet, the non-flexible tabs configured to deform one of the deformable lip and the ramped surface of the one of the fasteners to release the one of the fasteners from the fastener chamber in response to an applied force by a user.

15. The system of claim 11, wherein the plurality of resiliently flexible tabs are configured to transition from a first at-rest position to a second flexed position by flexing outward away from the longitudinal axes to allow the fasteners to move axially in the first direction, and wherein, at the first at-rest position, the resiliently flexible tabs are configured to interfere with a head of one of the fasteners to restrict movement of the fasteners in the second direction.

16. The system of claim 11, wherein the shaft of the tool includes a groove, and wherein, at the locked position, the projection of the drive clip extends into the groove of the shaft.

17. The system of claim 16, wherein, when the fastener cartridge is coupled to the shaft, the shaft is axially and rotationally fixed with respect to the fastener cartridge.

\* \* \* \* \*

UNITED STATES PATENT AND TRADEMARK OFFICE
CERTIFICATE OF CORRECTION

PATENT NO. : 10,286,532 B2
APPLICATION NO. : 15/274221
DATED : May 14, 2019
INVENTOR(S) : Garcia et al.

Page 1 of 1

It is certified that error appears in the above-identified patent and that said Letters Patent is hereby corrected as shown below:

In the Claims

In Column 34, Line 43, in Claim 11, after "tabs;", delete "and"

In Column 34, Line 49, in Claim 11, after "configured", insert --to--

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*